(12) United States Patent
Kawabe et al.

(10) Patent No.: US 7,026,406 B1
(45) Date of Patent: Apr. 11, 2006

(54) SYNDIOTACTIC STYRENE POLYMERS AND PROCESS FOR THE PRODUCTION THEREOF

(75) Inventors: Masanao Kawabe, Fukuoka (JP); Masahide Murata, Tokyo (JP); Toshio Kase, Tokyo (JP); Hiroyuki Ozaki, Kanagawa (JP); Yoshifumi Fukui, Osaka (JP); The Ban Hoang, Tokyo (JP); Jizhu Jin, Boulder, CO (US); Akira Miyazawa, Ibaraki (JP); Hideaki Hagihara, Ibaraki (JP); Kenji Tsuchihara, Ibaraki (JP); Yasuzo Suzuki, Ibaraki (JP); Michihiko Asai, Ibaraki (JP); Kazuo Soga, deceased, late of Chiba (JP); by Hisae Soga, legal representative, Chiba (JP)

(73) Assignees: National Institute of Advanced Industrial Science and Technology, Tokyo (JP); Japan Chemical Innovation Institute, Tokyo (JP)

( * ) Notice: Subject to any disclaimer, the term of this patent is extended or adjusted under 35 U.S.C. 154(b) by 52 days.

(21) Appl. No.: 10/203,545

(22) PCT Filed: Sep. 4, 2000

(86) PCT No.: PCT/JP00/05996

§ 371 (c)(1),
(2), (4) Date: Oct. 10, 2002

(87) PCT Pub. No.: WO01/58964

PCT Pub. Date: Aug. 16, 2001

(30) Foreign Application Priority Data

Feb. 10, 2000 (JP) .................................. 2000-033701
Feb. 10, 2000 (JP) .................................. 2000-033702
Mar. 31, 2000 (JP) .................................. 2000-099305

(51) Int. Cl.
*C08F 257/02* (2006.01)
*C08F 297/00* (2006.01)

(52) U.S. Cl. ................ 525/241; 525/245; 525/249; 525/333.2; 525/326.1; 525/359.2; 526/241; 526/293; 526/346; 526/347; 526/326

(58) Field of Classification Search .............. 525/241, 525/245, 249, 333.2, 326.1, 359.2, 326, 333.3, 525/361; 526/241, 293, 346, 347, 326, 902

See application file for complete search history.

(56) References Cited

U.S. PATENT DOCUMENTS

| | | | |
|---|---|---|---|
| 4,689,288 A | 8/1987 | Buiguez et al. | 430/270 |
| 5,446,117 A | 8/1995 | Baird et al. | |
| 5,554,695 A * | 9/1996 | Machida et al. | 525/268 |
| 5,616,656 A | 4/1997 | Dever et al. | |
| 5,866,659 A * | 2/1999 | Chung et al. | 525/279 |

FOREIGN PATENT DOCUMENTS

| | | |
|---|---|---|
| EP | 0 210 615 A2 | 2/1987 |
| EP | 0 570 932 | 11/1993 |
| EP | 0 745 619 A1 | 12/1996 |
| JP | 62-104818 | 5/1987 |
| JP | 62-1877081 | 8/1987 |
| JP | 63-241009 | 10/1988 |
| JP | 01-146912 | 6/1989 |
| JP | 01-278503 | 11/1989 |
| JP | 03-075204 | 3/1991 |
| JP | 03-025412 | 9/1991 |
| JP | 04-130114 | 5/1992 |
| JP | 05-017533 | 1/1993 |
| JP | 05-295056 | 11/1993 |
| JP | 05-310834 | 11/1993 |
| JP | 05-320280 | 12/1993 |
| JP | 05-320281 | 12/1993 |
| JP | 06-298862 | 10/1994 |
| JP | 11-158242 | 6/1999 |
| JP | 2000 026529 A1 | 1/2000 |
| WO | WO-01/02447 A2 | 1/2001 |

OTHER PUBLICATIONS

Riccardo, et al., "Synthesis of Syndiotactic Polystyrene: Reaction Mechanisms and Catalysis", Prog. Polym. Sci., vol. 21, No. 1, pp. 47–88, 1996.

Okuda, J., et al., "Syndiospecific polymerization of styrene using methylaluminoxane–activated bis(phenolato) titanium complexes", Macromolecular Chemistry and Physics, vol. 199, No. 4, pp. 543–545, Apr. 1, 1998.

(Continued)

*Primary Examiner*—James J. Seidleck
*Assistant Examiner*—Olga Asinovsky
(74) *Attorney, Agent, or Firm*—Darby & Darby

(57) ABSTRACT

A syndiotactic styrenic polymer having a narrow molecular weight distribution which is a (co)polymer comprising at least one structural unit represented by the following Formula (1):

$$-(CH-CH_2)- \text{ with phenyl group bearing } (R_a)_m \tag{1}$$

wherein $C_1$ of a phenyl group thereof has a tacticity of 30% or more in terms of a racemic pentad determined by $^{13}$C-NMR, and $R_a$ and m are as defined in the specification. The disclosure is also directed to a block copolymer comprising the above polymer as one segment, to a block graft polymer prepared by modifying one block of the above polymer with a nitrogen-containing aromatic polymer, and to a process for preparing a syndiotactic styrenic polymer in which a styrenic monomer is polymerized in the presence of a catalyst comprising a reaction product of a transition metal compound and at least one co-catalyst selected from organic aluminunoxy compounds.

10 Claims, 7 Drawing Sheets

OTHER PUBLICATIONS

Kim, et al., "Synthesis of 4–tert–butyldimethylsilylosxystyrene and its copolymerization with styrene using (η5–indenyl) trichlorotitanium in the presence of methylaluminoxane", Macromolecular Rapid Communications, vol. 20, No. 4, pp. 175–178, Apr. 1999.

Kawabe, et al., "Syndiospecific Living Polymerization of Silyl–Protected Hydroxystyrene Derivatives and Preparation of Syndiotactic Poly(4–hydroxystyrene) with Narrow Molecular Weight Distribution", Macromolecular Chemistry and Physics, vol. 202, No. 16, pp. 3157–3164, Nov. 7, 2001.

Kawabe, et al., "Syndiospecific Living Block Copolymerization of Styrenic Monomers Containing Functional Groups, and Preparation of Syndiotactic Poly{(4–hydroxystyrene)–block– [(4–methylstyrene)–co–(4–hydroxystyrene)]}", Macromolecular Chemistry and Physics, vol. 203, No. 1, pp. 24–30, Jan. 9, 2002.

Macromolecules 1998, 31, 8650–8652, Zhaomin Hou et al., One Step Block–Copolymerization Of Ethylene With Styrene By $C_5Me_5$/ER–Ligated Samarium (II) Complexes (ER=OAr, SAr).

Science and Technology in Catalysis, 1998, 269–277, Norio Tomotsu et al., Recent Development Of Catalysts For Syndiospecific Polymerization of Styrene.

Metalorganic Catalysts For synthesis And Polymerization, W. Kaminsky (Ed.), Apringer–Verlag, Berlin, 1999, pp. 435–445, K. Yokota et al., "Syndiospecific Polymerization of Styrene".

Advances in Polymer Science, vol. 127, pp. 143–187, Springer–Verlag Berlin Heidelberg, 1997, W. Kaminsky et al., "Metallocences for Polymer Synthesis".

Chem. Rev. 2000, 1223–1252, G. W. Coates, "Precise Control of Polyolefin Sterochemistry Using Single–Site Metal Catalysts".

R. Po' et al.: "Synthesis of syndiotactic polystyrene: Reaction mechanisms and catalysis," Prog. Polym: Sci., 1996, vol. 21, 47–88.

J. Okuda et al.: "Syndiospecific polymerization of styrene using methylaluminoxane–activated bis(phenolato)titanium complexes," Macromol. Chem. Phys., 1998, vol. 199, 543–545.

J. Amer. Chem. Soc., 1957, vol. 79, pp. 2026–2027.

Makromol. Chem., 1960, vol. 36, pp. 200–208.

Ishihama, Y., et al.: "Living cationic polymerization of sytrene by the 1–phenylthyl chloride/tin tetracholride initialing system in the presence of tetra–n–butylammonium chloride," Polymer Bulletin, 1990, vol. 24, pp. 201–206.

Higashimura, T. et al.: "Living Cationic Polymerization of Styrene: New Initiating Systems Based on Added Halide Salts and the Nature of the Growing Species," MACROMOLECULES, 1993, vol. 26, pp. 744–751.

Georges, M. K. et al.: "Narrow Molecular Weight Resins by a Free–Radical Polymerization Process," MACROMOLECULES, 1993, vol. 26, pp. 2987–2988.

Georges, M. K. et al.: "Narrow Polydispersity Polystyrene by a Free–Radical Polymerization Process–Rate Enhancement," MACROMOLECULES, 1994, vol. 27, pp. 7228–7229.

Ho, T. et al.: "Synthetic Methods and Reactions; $32^1$. Mild and Effective Cleavage of Esters and Ethers with Phenyltrimethylsilane/Iodine Reagent," SYNTHESIS, 1977, pp. 417–418.

Willard, P. G. et al.: "Boron Trihalide–Methyl Sulfide Complexes as Convenient Reagents For Dealkylation of Aryl Ethers," Tetrahedron Letters, 1980, vol. 21, pp. 3731–3734.

McOmie, J.F.W. et al.: "Demethylation of Aryl Methyl Ethers by Boron Tribromide," TETRAHEDON, 1968, vol. 24, pp. 2289–2292.

Grassi, A. et al.: "Reactivity of Some Substituted Styrenes in the Presence of a Syndiotactic Specific Polymerization Catalyst," MACROMOLECULES, 1989, vol. 22, pp. 104–108.

Barclay, G.C. et al.: "The 'Living' Free Radical Synthesis of Poly(4–hydroxystyrene): Physical Properties and Dissolution Behavior," MACROMOLECULES, 1988, vol. 31, pp. 1024–1031.

Barclay, G.G. et al.: "Narrow Polydispersity Polymers for Microlithography: Synthesis and Properties," Proc. SPIE., 1996, vol. 2724, pp. 249–260.

Higashimura, T. et al.: "Living cationic polymerization of 4–tert–butoxystyrene and synthesis of (poly4–vinylphenol) with narrow molecular weight distribution," Makromol, Chem., Suppl., 1989, vol. 15, pp. 127–136.

Hirai, A. et al.: "Polymerization of Monomers Containing Functional Groups Protected by Trialkylsilyl Groups, 1," Makromol. Chem., Rapid Commun., 1982, vol. 3, pp. 341–946.

Furukawa, J. et al.: "Phosphorus–Containing Polystyrine Derivatives as Flame Resistance," Polymer Journal, 1980. vol. 12, No. 5. pp. 277–285.

Ito, H. et al.: "Living Anionic Polymerzation of Silyl–Protected Hydroxystyrene at Room Temperature," Polym. Mater. Sci. Eng., 1993, vol. 68, pp. 12–13.

Weiss, W.: "Chloromethyl Ethers, Cigarettes, Cough and Cancer," J. Occup. Med., 1976, vol. 18, pp. 194–199.

Pepper, K.W. et al.: "Properties of Ion–exchange Resins in Relation to their Structure. Part VI, Anion–exchange Resins derived from Styrene–Divinyl–benzene Copolymers," J. Chem. Soc., 1953, vol. 18, pp. 4097–4105.

Kurusu et al.: "Synthesis and Reaction of Polymer Containing Nicotinamide Structure," Kogyokagaku Zassi, 1968, vol. 71, No. 6, pp. 934–941 (Translation of pp. 935 and 940).

Kobunshi Jikken Gaku, 1996, vol. 6, pp. 48–55 (Translation of pp. 52 and 53).

Gervaśi, J.A. et al.: "The Preparation of Graft Copolymers of Polystyrene with Poly–2–vinylpyridine." J. Polymer Sci.: Part C, 1968, vol. 24, pp. 207–218.

Selb, J, et al.: "Graft copolymer: 1. Synthesis and characterization of poly(styrene–g–2–vinylpyridine)" POLYMER, 1979, vol. 20, pp. 1259–1267.

Selb, J. et al.: "Graft copolymers: 2. Specific instability of some poly (styrene–g–2–vinyl pyridines) obtained from chloromethylated polystyrene," POLYMER, 1979, vol. 20, pp. 1268–1272.

Selb, J. et al.: "Graft copolymers: 3. Synthesis and Characterization of poly (styrene–g–4 vinylpyridine)," POLYMER, 1979, vol. 20, pp. 1273–1280.

Mori, M. et al.: "Synthesis and Morphology of Polystyrene Macromonomer–4–Vinylpyridine Graft Copolymers," Kobunshi Ronbunshu, 1992, vol. 49, pp. 547–550.

Matsushita, Y. et al.: "Preparation and characterization of ABB graft copolymers," POLYMER, 1996, vol. 37. pp. 321–325.

\* cited by examiner

SYNDIOTACTIC STYRENE POLYMERS AND PROCESS FOR THE PRODUCTION THEREOF

This application is a national phase application under 35 U.S.C. § 371 of International Application No. PCT/JP00/05996, filed Sep. 4, 2000, which was published on Aug. 16, 2001 as International Publication No. WO 01/58964, and claims the benefit of Japanese Patent Application Nos. JP 2000-33701, filed Feb. 10, 2000, JP 2000-33702, filed Feb. 10, 2000, and JP 2000-99305, filed Mar. 31, 2000.

TECHNICAL FIELD

1. Field of the Invention

The present invention relates to styrenic (co)polymers which have a narrow molecular weight distribution and a highly syndiotacticstructure and to a modified (co)polymers thereof and to processes for preparation of the same.

2. Background Art

Styrenic polymers produced by radical polymerization have so far been molded into various shapes by various molding methods and widely used for home electric appliances, business machines, household goods, packaging containers and other industrial materials.

A process for preparation of polystyrene has so far been known for a relatively long time. Proposed are, for example, production processes in which styrenic monomers are subjected to living anionic polymerization in J. Amer. Chem. Soc., 1957, vol. 78, pp. 2026~2027 and Makromol. Chem., 1960, vol. 36, pp. 200~208, production processes in which styrenic monomers are subjected to living cationic polymerization in Polymer Bulletin, 1990, vol. 24, pp. 201~206 and Macromolecules, 1993, vol. 26, pp. 744~751 and production processes in which styrenic monomers are subjected to living radical polymerization in Macromolecules, 1993, vol. 26, p. 2987~2988 and Macromolecules, 1994, vol. 27, p. 7228~7229. However, styrenic polymers obtained by these living anionic polymerization process, living cationic polymerization process and living radical polymerization process have an atactic structure as a steric structure thereof and have the defect that they are inferior in heat resistance and chemical resistance.

Styrenic polymers having a highly syndiotactic structure and styrenic copolymers obtained by copolymerizing these styrenic monomers with other components have been studied as polymers solving the defects of such styrenic polymers having an atactic structure (Japanese Patent Application Laid-Open No. Hei 3-205412, Japanese Patent Publication No. Hei 3-7685, Japanese Patent Publication No. Hei 1-37403 and Japanese Patent Application Laid-Open No. Sho 63-241009). These polymers are excellent in heat resistance, chemical resistance and electric characteristics and expected to be applied in various fields.

On the other hand, it is known that among styrenic polymers, styrenic polymers having polar substituents such as hydroxystyrenic polymers are useful, for example, as materials for a printed circuit board, an offset PS printing plate and a photoresist and functional materials for a flame retardant adhesive, a metal surface treating agent, a resin modifier and a compatibilizer. However, conventional hydroxystyrenic polymers have the problem in that they have unsatisfactory heat resistance due to low stereoregularity and are restricted in industrial applications thereof.

In connection with hydroxystyrenic polymers among styrenic polymers having a syndiotactic structure, a process for preparation of an syndiotactic alkoxy-substituted polystyrene as a precursor thereof by coordination polymerization is disclosed in Japanese Patent Application Laid-Open No. Hei 5-310834. In general, it is known that alkoxy-substituted styrenes are readily converted into phenols [Synthesis, p. 417 (1977), Tetrahedron Lett., vol. 21, p. 3731 (1980) and Tetrahedron, vol. 24, p. 2289 (1968)]. However, only syndiotactic p-methoxystyrenic polymers are disclosed in the above patent, and a deblocking reaction of p-methoxystyrene is very difficult, so that there has been such problem of causing a rise in cost of industrially producing hydroxystyrenic polymers by deblocking.

Also, as disclosed in the comparative examples of the above patent gazette, only atactic polymers were obtained by polymerization using p-t-butoxystyrene, which is an alkoxy-substituted styrene readily susceptible to deblocking reaction. Further, reported as well is polymerization of p-methoxystyrene and m-methoxystyrene using a tetrabenzyltitanium/methylaminoxane base catalyst by coordination polymerization [Macromolecules, vol. 22, p. 104 (1989)]. According to this process, only alkoxystyrenic polymers having an atactic structure were obtained, and it was impossible to synthesize hydroxystyrenic polymers having a highly syndiotactic structure. On the other hand, it is reported that hydroxystyrenic polymers can be synthesized by other polymerization methods, for example, a radical polymerization method [Macromolecules, vol. 31, p. 1024 (1998) and Proc. SPIE., vol. 2724, p. 249 (1996)], a cationic polymerization method [Makromol. Chem. Suppl., vol. 15, p. 127 (1989)] and an anionic polymerization method [Makromol. Chem. Rapid Commun., vol. 3, p. 941 (1982)]. However, all of these synthetic methods afford atactic hydroxystyrenic polymers.

Various processes for polymerization of trialkylsilyloxystyrenes have so far been known, and reported are, for example, a radical polymerization method [Polym. J., vol. 12, p. 277 (1980) and U.S. Pat. No. 4,689,288] and an anionic polymerization method [Makromol. Chem. Rapid Commun., vol. 3, p. 941 (1982)].

However, all of these synthetic methods afford atactic polytrialkylsilyloxystyrenes. Further, trialkylsilyloxystyrenes such as trimethylsilyloxystyrene, triethylsilyloxystyrene and t-butyldimethylsilyloxystyrene are described in Japanese Patent Application Laid-Open No. Hei 6-298862, but nothing are specifically shown.

Further, it is reported in Polym. Mater. Sci. Eng., vol. 68, p. 12 (1993) that t-butyldimethylsilyloxystyrene is anionically polymerized in a methylcyclohexane solvent, whereby a syndiotacticity-rich t-butyldimethylsilyloxystyrenic polymers can be synthesized. However, the polymer obtained by this process had low stereoregularity, and the syndiotacticity thereof was not satisfactory.

It is known that styrenic polymers modified with halogenated methyl group are very useful as functional resins such as anion exchange resins, supports for solid phase synthesis of peptide, negative type resists, electroconductive resins and supports of polymeric reagents and polymeric catalysts, and as intermediates for functional polymers. Such styrenic polymers modified with halogenated methyl group and a process for the preparation of the same are disclosed in 1) J. Occup. Med., 1976, vol. 18, p. 194, 2) J. Chem. Soc., 1953, vol. 18, p. 4097, 3) Kogyo Kagaku Zasshi, 1968, vol. 71, p. 934, 4) Kobunshi Jikken Gaku, 1996, vol. 4, pp. 49~51 and 5) Japanese Patent Application Laid-Open No. Hei 11-158242.

However, styrenic polymers modified with the halogenated methyl group which are obtained by the synthetic methods described above which have so far been disclosed have an atactic structure. Accordingly, styrenic polymers modified with the halogenated methyl group which are produced by the synthetic methods which have so far been disclosed have the defect that they are inferior in heat resistance and chemical resistance due to an atactic structure thereof, and they have had the problem in industrial application such that the application fields thereof are restricted.

On the other hand, disclosed in Japanese Patent Application Laid-Open No. Hei 3-72504 are styrenic polymers having a syndiotactic structure which may have a substituent such as an alkyl group, a halogen, a halogen-substituted alkyl group, an alkoxy group, a carboxyalkyl group, an alkylsilyl group, a sulfonic acid ester group and a dialkoxyphosphyl group. However, monomers having substituents which were used for the styrenic polymers having a syndiotactic structure disclosed in the examples of the foregoing published gazette were only alkyl group-substituted styrenes such as p-methylstyrene, m-methylstyrene and p-tert-butylstyrene and halogen-substituted styrenes such as p-chlorostyrene and m-chlorostyrene. As a matter of fact, when styrene base monomers having a halogenated alkyl group were polymerized according to a technique disclosed in the above patent publication gazette, nothing but polymers having an atactic structure was obtained.

Further, styrenic polymers with a halogenated methyl group in which a polymer chain has a syndiotactic structure of 85% or more of a racemic pentad are disclosed in Japanese Patent Publication No. Hei 7-84503. However, in a process for the preparation of styrenic polymers having a syndiotactic structure by a method disclosed in the above patent gazette, block copolymers can not be obtained at high efficiency due to the fact that it does not have living polymerization characteristics. As a matter of fact, synthetic examples of styrenic polymers block copolymers having a syndiotactic structure were not disclosed in the examples of the above patent gazette. Accordingly, it was not even possible to imagine from the technique disclosed in the above patent gazette obtaining a styrenic block copolymer having a syndiotactic structure and a halogenated alkyl group. In addition thereto, a process for the preparation of syndiotactic p-halo-methyl styrenic polymers which is disclosed in the above patent gazette is a process in which syndiotactic styrenic polymers are reacted with a halomethylating agent in the presence of a solvent and an acid catalyst. Chloromethyl methyl ether having high toxicity is specifically disclosed as the halomethylating agent in the examples of the above patent gazette, and there is a problem in industrially producing it.

Next, syndiotactic styrenic block copolymers are disclosed as a syndiotactic styrenic polymers with a improved property in Japanese Patent Application Laid-open No. Hei 4-130114, Japanese Patent Application Laid-open No. Hei 5-320280 and Japanese Patent Application Laid-Open No. Hei 5-320281. However, the polymers disclosed in the examples of the above patent gazettes not only have the insufficient properties in the industrial applications as functional materials for an adhesive, a resin modifying agent and a compatibilizer, caused by a broad molecular weight distribution of the syndiotactic styrenic polymers segments due to a lack of a living polymerization characteristics, but also have problems on the process for the preparation of the block copolymer in which the polymers produced in this polymerization system have a low content of the block copolymer so that separation and refining should be carried out additionally in order to collect the block copolymer having a high purity, and that this synthetic method is unsatisfactory for industrial application in terms of the cost.

The steric structure of styrenic polymers obtained by a living anionic polymerization method, a living cationic polymerization method and a living radical polymerization method which can be used for the preparation of styrenic block copolymers which have so far been disclosed has an atactic structure. These living polymerization methods can not afford syndiotactic styrenic block copolymers having a high molecular weight and a narrow molecular weight distribution.

On the other hand, it is known that graft copolymers prepared by graft polymerization of styrenic polymers with nitrogen-containing aromatic monomers such as vinylpyridine are useful as functional materials in the various application fields such as adhesives, resin modifying agents, compatibilizer, surfactants, raw materials of mosaic charging membrane for separating an electrolyte, and dispersants of light-emitting pigment for a photoelectric image.

Such styrene•vinylpyridine graft copolymers and processes for the preparation of the same are disclosed in 1) J. Polymer Sci., Part C, 1968, vol. 24, pp. 207~218, 2) Polymer, 1979, vol. 20, pp. 1259~1267, 3) Polymer, 1979, vol. 20, pp. 1268~1272, 4) Polymer, 1979, vol. 20, pp. 1273~1280, 5) Kobunshi Ronbunshu, 1992, vol. 49, pp. 547~550 and 6) Polymer, 1996, vol. 37, pp. 321~325.

However, the steric structure of styrenic polymer segments in the styrene•vinylpyridine graft copolymers which have so far been disclosed is an atactic structure. Accordingly, the styrene•vinylpyridine graft copolymers produced by the techniques which have so far been disclosed have the defect that they are inferior in heat resistance and chemical resistance since the styrenic polymer segments have an atactic structure, and there has been the problem in industrial application such that the uses thereof are restricted.

Further, disclosed in Japanese Patent Application Laid-Open No. Hei 5-17533 is a technique for copolymerizing a styrenic monomer with a styrenic monomer containing an unsaturated hydrocarbon group using a transition metal compound to synthesize a syndiotactic prepolymer with a carbon-carbon unsaturated bond and conduct graft polymerization of the prepolymer with an ethylenically unsaturated monomer. However, the graft polymer produced by the preparative method disclosed in the above patent has the defect of reduced properties on heat resistance and chemical resistance which are the characteristics of styrenic polymers having a syndiotactic structure since a grafted polymer is bonded randomly on the syndiotactic styrenic polymer backbone. Further, the synthetic method disclosed in the above published patent gazette has the defects that the syndiotactic styrenic polymer segments have a broad molecular weight distribution due to a lack of a living polymerization characteristics, so that when it is used as a functional material for an adhesive, a resin modifier and a compatibilizers, the insufficient properties thereof are exhibited in the industrial application thereof. A block•graft copolymer comprising a styrenic polymer segment with a highly syndiotactic structure and a syndiotactic styrenic polymer segment with a nitrogen-containing aromatic polymer graft and a process for the preparation of the same were hard to be suggested from the synthetic methods which have so far been disclosed.

An objective of this invention is to provide syndiotactic styrenic (co)polymers, syndiotactic styrenic block (co) polymers and modified products thereof and block•graft copolymers comprising a syndiotactic styrenic polymer segment and a syndiotactic styrenic polymer segment with a nitrogen-containing aromatic polymer graft which are useful as raw materials for various high performance resins and functional resins because of their excellent heat resistance and molding processability originating from their high syndiotacticity, high molecular weight and narrow molecular weight distribution. Another objective of this invention is to provide processes for the preparation of the same.

DISCLOSURE OF THE INVENTION

Intensive investigations repeated by the present inventors in order to solve the problems described above have resulted in finding that styrenic (co)polymers having a narrow molecular weight distribution and a highly syndiotactic structure are obtained by polymerization of at least one styrenic monomer at a temperature of 20° C. or lower in the presence of a catalyst comprising a reaction product of a specific transition metal compound with at least one promoter and that useful modified products in which they are used as precursors are obtained, and thus the present invention has come to be completed.

That is, the present invention comprises:

(1) a syndiotactic styrenic polymer which is a (co)polymer comprising at least one structural unit represented by the following Formula (1):

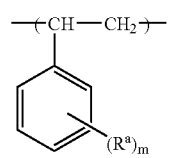

(1)

(wherein $R^a$ represents a hydrogen atom, a halogen atom, a hydrocarbon group having 1 to 30 carbon atoms or a substituent containing at least one atom selected from the group consisting of an oxygen atom, a nitrogen atom, a sulfur atom, a phosphorus atom, a selenium atom, a silicon atom, a tin atom and a germanium atom; and m represents an integer of 0 to 5, provided that when m is plural, respective $R^a$'s may be the same or different), wherein $C_1$ carbon of a phenyl group thereof has a tacticity of 30% or more in terms of a racemic pentad determined by $^{13}$C-NMR; the number average molecular weight (Mn) satisfies the following equation (2); and a relation between the number average molecular weight (Mn) and the weight average molecular weight (MW) satisfies the following equation (3):

$$5000 \leq Mn \leq 10000000 \quad (2)$$

$$Mw/Mn \leq 1.5 \quad (3)$$

(2) a process for preparation of a syndiotactic styrenic polymers in which at least one monomer selected from the group consisting of styrenic monomers represented by the following Formula (6)

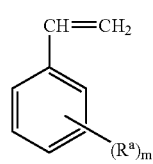

(6)

(wherein $R^a$ represents a hydrogen atom, a halogen atom, a hydrocarbon group having 1 to 30 carbon atoms or a substituent containing at least one atom selected from the group consisting of an oxygen atom, a nitrogen atom, a sulfur atom, a phosphorus atom, a selenium atom, a silicon atom, a tin atom and a germanium atom; and m represents an integer of 0 to 5, provided that when m is plural, respective $R^a$'s may be the same or different) is polymerized at a temperature of 20° C. or lower in the presence of a catalyst comprising principally a reaction product of a catalyst component (A) with a co-catalyst (B):

(A) at least one transition metal compound selected from the group consisting of compounds represented by the following Formulas (4) or (5):

$$MR^1_x R^2_y R^3_z X^1_{4-(x+y+z)} \quad (4)$$

$$MR^1_u R^2_v X_{13-(u+v)} \quad (5)$$

(wherein $R^1$, $R^2$ and $R^3$ each represent a hydrogen atom, an alkyl group having 1 to 20 carbon atoms, an aryl group, an alkylaryl group, an arylalkyl group and an aryloxy group each of which has 6 to 20 carbon atoms, an acyloxy group having 1 to 20 carbon atoms, an alkoxy group having 1 to 20 carbon atoms, a thioalkoxy group having 1 to 20 carbon atoms, a thioaryloxy group having 6 to 20 carbon atoms, an amino group, a cyclopentadienyl group, a substituted cyclopentadienyl group, an indenyl group, a substituted indenyl group, a fluorenyl group or a substituted fluorenyl group; M represents a transition metal selected from the group consisting of titanium (Ti), zirconium (Zr), hafnium (Hf) and vanadium (V); $X^1$ represents a halogen atom; these $R^1$, $R^2$ and $R^3$ may be the same or different; x, y and z each represent an integer of 0 to 4; and u and v each represent an integer of 0 to 3) and (B) at least one co-catalyst selected from the following (a) to (d):

(a) an organic aluminumoxy compound, (b) an ionic compound which can be reacted with the transition metal compound described above to form a cationic transition metal compound, (c) a Lewis acid compound which can be reacted with the transition metal compound described above to form a cationic transition metal compound, and (d) an organic metal compound of a first, second and thirteenth group elemental metal in the periodic table, (3) a syndiotactic trialkylsilyloxystyrenic polymer comprising a structural unit represented by the following Formula (7) and having a number average molecular weight of 600 or more:

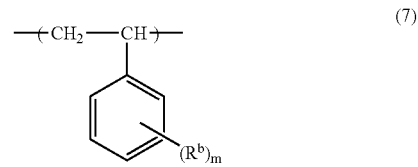

(7)

(wherein $R^b$ represents a trialkylsilyloxy group having 3 to 30 carbon atoms; n represents an integer of 1 to 3; and when n is plural, $R^b$'s may be the same or different) and in which a tacticity thereof is 30% or more in terms of a racemic pentad determined by $^{13}$C-NMR, (4) a process for preparation of the polymer as described in the above item (3) in which a trialkylsilyloxystyrene base monomer represented by the following Formula (8):

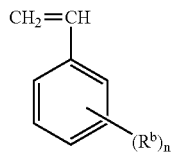
(8)

(wherein $R^b$ represents a trialkylsilyloxy group having 3 to 30 carbon atoms; n represents an integer of 1 to 3, and when n is plural, respective $R^b$ may be the same or different) is polymerized in the presence of the catalyst as described in the above item (2), (5) a syndiotactic hydroxystyrenic polymer having a structural unit represented by the following Formula (9) and a number average molecular weight of 600 or more:

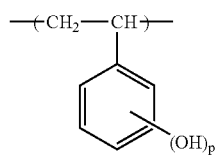
(9)

(wherein p represents an integer of 1 to 3) and in which a tacticity thereof is 30% or more in terms of a racemic pentad determined by $^{13}$C-NMR, (6) a process for preparation of a hydroxystyrene polymer, comprising the steps of:
polymerizing a styrenic monomer represented by the following Formula (10):

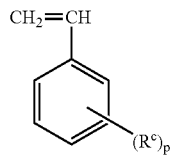
(10)

(wherein $R^c$ represents a trialkylsilyloxy group having 3 to 30 carbon atoms, an alkoxy group having 4 to 31 carbon atoms or a trialkylgermaniumoxy group having 3 to 30 carbon atoms; p represents an integer of 1 to 3, and when p is plural, $R^c$'s may be the same or different) in the presence of the catalyst as described in the above item (2) to thereby produce a styrenic polymer comprising at least one structural unit having a highly syndiotactic structure represented by the following Formula (11):

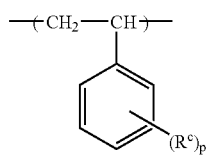
(11)

($R^c$ represents a trialkylsilyloxy group having 3 to 30 carbon atoms, an alkoxy group having 4 to 31 carbon atoms or a trialkylgermaniumoxy group having 3 to 30 carbon atoms; p represents an integer of 1 to 3, and when p is plural, $R^c$'s may be the same or different) and then bringing this into contact with an acid or a base in the presence of an organic solvent to subject it to deblocking reaction, (7) a syndiotactic styrenic block copolymer having a structure where a polymer segment (I) which comprises at least one structural unit represented by the following Formula (12):

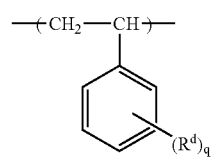
(12)

(wherein $R^d$ represents methyl, and q represents an integer of 1 to 5) and in which $C_1$ carbon of a phenyl group thereof has a tacticity of 30% or more in terms of a racemic pentad determined by $^{13}$C-NMR is connected in series with a polymer segment (II) which comprises at least one structural unit represented by the following Formula (13):

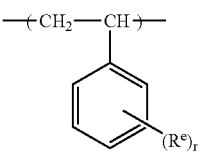
(13)

(wherein $R^e$ represents a hydrogen atom, a hydrocarbon group having 1 to 30 carbon atoms or a substituent containing at least one atom selected from the group consisting of an oxygen atom, a nitrogen atom, a sulfur atom, a phosphorus atom, a selenium atom, a silicon atom, a tin atom and a germanium atom; and r represents an integer of 0 to 5, provided that when r is plural, respective $R^e$ may be the same or different), and in which $C_1$ carbon of a phenyl group thereof has a tacticity of 30% or more in terms of a racemic pentad determined by $^{13}$C-NMR; the number average molecular weight (Mn) satisfies the following equation (14); and a relation between the number average molecular weight (Mn) and the weight average molecular weight (Mw) satisfies the following equation (15):

$$1200 \leq Mn \leq 20000000 \quad (14)$$

$$Mw/Mn \leq 2.5 \quad (15)$$

(8) preferably, a number average molecular weight (Mn) of the block polymer segment (I) in these syndiotactic styrenic polymers falls in a range of the following equation (16), and a relation between the number average molecular weight (Mn) and the weight average molecular weight (Mw) satisfies the following equation (17):

$$1000 \leq Mn \leq 10000000 \quad (16)$$

$$Mw/Mn \leq 2.5 \quad (17)$$

(9) a process for preparation of the syndiotactic styrenic block copolymer as described in the above item (7), comprising the steps of:
(i) bringing at least one transition metal component which is the component (A) in advance into contact with at least one co-catalyst which is the component (B) at a temperature of −50 to 50° C. for 5 seconds to 10 hours to prepare a catalyst as described in the above item (2) and subsequently polymerizing at least one styrenic monomer represented by the following Formula (18) or at least one styrenic monomer represented by the following Formula (19) at a temperature of 20° C. or lower in the presence of the catalyst to obtain a syndiotactic styrenic polymer:

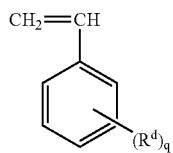

(18)

(wherein $R^d$ represents methyl, and q represents an integer of 1 to 5)

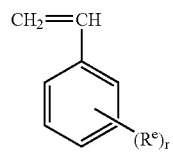

(19)

(wherein $R^e$ represents a hydrogen atom, a hydrocarbon group having 1 to 30 carbon atoms or a substituent containing at least one atom selected from the group consisting of an oxygen atom, a nitrogen atom, a sulfur atom, a phosphorus atom, a selenium atom, a silicon atom, a tin atom and a germanium atom; and r represents an integer of 0 to 5, provided that when r is plural, respective $R^e$ may be the same or different) and then (ii) polymerizing, in the presence of the living syndiotactic styrenic polymers obtained in the step (i) described above, at least one styrenic monomer represented by either Formula (18) or Formula (19) which is different from the styrenic monomer polymerized in the step (i) described above,

(10) a syndiotactic styrenic block copolymer comprising 0.1 mole % or more of at least one structural unit represented by the following Formula (20):

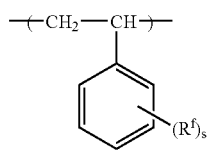

(20)

(wherein $R^f$ represents a halogenated methyl group having a halogen atom selected from the group consisting of fluorine, chlorine, bromine and iodine, and s represents an integer of 1 to 5),

(11) a halogenated methyl-modified syndiotactic styrenic block polymer comprising structural units represented by the following Formula (12) and the following Formula (20):

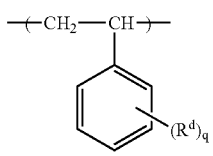

(12)

(wherein $R^d$ represents methyl, and q represents an integer of 1 to 5)

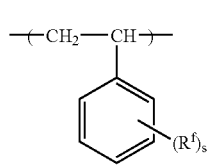

(20)

(wherein $R^f$ represents a halogenated methyl group having a halogen atom selected from the group consisting of fluorine, chlorine, bromine and iodine, and s represents an integer of 1 to 5), wherein one or more structural units represented by Formula (12) and Formula (20) have a content satisfying the following equations (21) and (22), and $C_1$ carbon of phenyl groups in the polymer segments has a tacticity of 30% or more in terms of a racemic pentad determined by $^{13}$C-NMR:

2<structural unit (Formula (12))+structural unit (Formula (20))<100     (21)

0.1≦structural unit (Formula (20))<100     (22)

(12) a process for preparation of the syndiotactic styrenic block copolymer as described in the above item (11), comprising reacting a syndiotactic styrenic polymer comprising a structural unit represented by the following Formula (12):

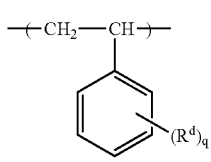

(12)

(wherein $R^d$ represents methyl, and q represents an integer of 1 to 5) with a halogenating agent at a temperature of −20 to 200° C. in the presence of a catalyst and a solvent to convert a part or the whole part of the methyl groups into halogenated methyl groups or reacting the syndiotactic styrenic block copolymer as described in the above item (7) with a halogenating agent at a temperature of −20 to 200° C. in the presence of a catalyst and a solvent to convert a part or the whole part of the methyl groups into halogenated methyl groups,

(13) a syndiotactic styrenic block•graft copolymer in which at least one structural unit per molecule of the polymer out of the structural units represented by Formula (20) contained in the syndiotactic styrenic base polymer as described in any of the item (10) or (11) described above is converted into a structural unit represented by the following Formula (23):

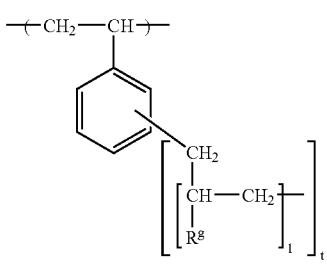

(23)

(wherein $R^g$ represents at least one nitrogen-containing aromatic residue selected from the group consisting of pyridine, substituted pyridine, pyrimidine, substituted pyrimidine, pyrazine, substituted pyrazine, triazine, substituted triazine, quinoline, substituted quinoline, isoquinoline, substituted isoquinoline, acridine, substituted acridine, phthalazine, substituted phthalazine, quinoxaline, substituted quinoxaline, phenanthroline and substituted phenanthroline; l represents a polymerization degree of 3 or more of the graft polymer; and t represents an integer of 0 to 5), wherein a relation between the number average molecular weight (Mn) and the weight average molecular weight (Mw) of the graft chain satisfies the following equation (24):

$$Mw/Mn \leq 2.0 \qquad (24)$$

(14) a process for preparation of this syndiotactic styrenic block•graft copolymer, comprising bringing the halogenated methyl-modified syndiotactic styrenic polymer as described in any of items (10) and (11) described above into contact with a nitrogen-containing aromatic living polymer obtained by bringing an anionic polymerization initiator in advance into contact with a nitrogen-containing aromatic monomer represented by the following Formula (25) at −100 to 100° C.:

(25)

(wherein $R^g$ represents at least one nitrogen-containing aromatic residue selected from the group consisting of pyridine, substituted pyridine, pyrimidine, substituted pyrimidine, pyrazine, substituted pyrazine, triazine, substituted triazine, quinoline, substituted quinoline, isoquinoline, substituted isoquinoline, acridine, substituted acridine, phthalazine, substituted phthalazine, quinoxaline, substituted quinoxaline, phenanthroline and substituted phenanthroline). (15) a trialkylsilyloxystyrenic monomer comprising a structure represented by the following Formula (26):

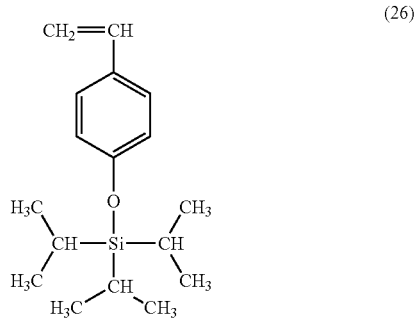

(26)

BEST MODE FOR CARRYING OUT THE INVENTION

Figure 1A:
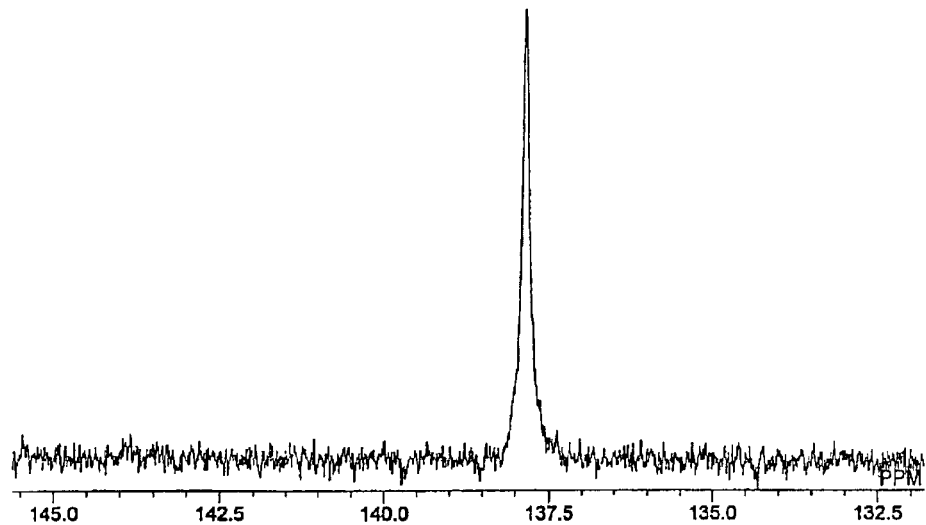
FIG. 1 is a $^{13}$C-NMR spectrum of a polymer obtained in Example 9.

The embodiments of the present invention shall be explained below in details.

In the present invention, the syndiotactic styrenic polymer described above is a polymer or a copolymer having one of the structural units (repetitive units) described above represented by Formula (1) or an optional combination of different two or more kinds thereof. $R^a$ here in the structural unit represented by Formula (1) represents a hydrogen atom, a halogen atom, a hydrocarbon group having 1 to 30 carbon atoms or a substituent containing at least one selected from the group consisting of an oxygen atom, a nitrogen atom, a sulfur atom, a phosphorus atom, a selenium atom, a silicon atom, a tin atom and a germanium atom.

In this case, fluorine, chlorine, bromine and iodine can be given as the halogen atom. Further, the specific examples of the hydrocarbon group having 1 to 30 carbon atoms include an alkyl group having 1 to 30 carbon atoms such as methyl, ethyl, isopropyl and tertiary butyl, an aryl group having 6 to 30 carbon atoms which has a substituent containing a hydrogen atom, a halogen atom, a carbon atom, an oxygen atom, a nitrogen atom, a sulfur atom, a phosphorus atom, a selenium atom, a silicon atom, a germanium atom or a tin atom on a benzene ring and a halogen-substituted alkyl group having 1 to 20 carbon atoms such as a chloroethyl group, bromomethyl group and a bromoethyl group.

The aryl group having 6 to 30 carbon atoms which has a substituent containing a hydrogen atom, a halogen atom, a carbon atom, an oxygen atom, a nitrogen atom, a sulfur atom, a phosphorus atom, a selenium atom, a silicon atom, a germanium atom or a tin atom on a benzene ring includes, for example, a benzene ring, a naphthalene ring, a phenanthrene ring, an anthracene ring, an indene ring, an azulene ring, a heptalene ring, a biphenylene ring, an as-indacene ring, an s-indacene ring, an acenaphthylene ring, a phenalene ring, a fluoranthene ring, an acephenanthrene ring, an aceanthrylene ring, a triphenylene ring, a naphthacene ring, a pleiadene ring, a picene ring, a perylene ring, a pentaphene ring, a pentacene ring, a rubicene ring, a corocene ring, a pyranthrene ring, an ovalene ring and those aryl groups which are substituted on optional positions with alkyl substituents (methyl, ethyl, isopropyl, tertiary butyl and the like), halogen-substituted alkyl groups (chloroethyl, bromoethyl and the like), substituents containing an oxygen atom (methoxy, ethoxy, isopropoxy, methoxycarbonyl, acyloxy and the like), substituents containing a silicon atom (trimethylsilyl and the like), substituents containing a germanium atom (trimethylgermyl and the like), substituents containing a tin atom (trimethylstannyl, tributylstannyl, triphenylstannyl and the like), substituents containing a nitrogen atom (dimethylamino, diazo, nitro, cyano and the like), substituents containing a sulfur atom (sulfonic acid, methyl sulfonate, phenylthio, methylthio, mercapto and the like), substituents containing a selenium atom (methylseleno, phenylseleno, methylselenoxyl, phenylselenoxyl and the like) and substituents containing a phosphorus atom (methyl phosphate, phosphite, dimethylphosphino, diphenylphosphino, methylphosphinyl, phenylphosphinyl and the like).

The substituents containing an oxygen atom include methoxy, ethoxy, isopropoxy, methoxycarbonyl and acyloxy.

The substituents containing a silicon atom include trimethylsilyl.

The substituents containing a germanium atom include trimethylgermyl.

The substituents containing a tin atom include trimethylstannyl, tributylstannyl and triphenylstannyl.

The substituents containing a nitrogen atom include dimethylamino, diazo, nitro and cyano.

The substituents containing a sulfur atom include sulfonic acid, methyl sulfonate, phenylthio, methylthio and mercapto.

The substituents containing a selenium atom include methylseleno, phenylseleno, methylselenoxyl and phenylselenoxyl.

The substituents containing a phosphorus atom include methyl phosphate, phosphite, dimethylphosphino, diphenylphosphino, methylphosphinyl and phenylphosphinyl.

In the structural unit represented by Formula (1), m is an integer of 0 to 5, and when m is plural, m groups of $R^a$ each may be the same or different.

The syndiotactic styrenic polymers of the present invention have such structural unit (repetitive unit) as described above. Further, in stereoregularity thereof, it has principally a syndiotactic structure, that is, a steric structure in which a phenyl group having a substituent or having no substituent, which is a side chain relative to a principal chain formed from a carbon-carbon bond is positioned one after the other in an opposite direction, and a tacticity thereof is determined by a nuclear magnetic resonance method (NMR method). To be specific, it is determined by analysis of a signal of $C_1$ carbon on an aromatic ring and a methine•methylene carbon signal determined by a $^{13}$C-NMR method (nuclear magnetic resonance spectrum with a carbon isotope) or a proton signal in $^1$H-NMR.

Tacticity determined by NMR can be shown by an existence proportion of continuous plural constitutional units (that is, an existence proportion of continuous constitutional units in a relative conformational relation), for example, diad in the case of two units, triad in the case of tree units and pentad in the case of five units. The structural unit having principally a syndiotactic structure according to the present invention shows usually, though a degree of the syndiotacticity is a little varied depending on the kind of the substituent and a content ratio of the respective repetitive units, a structural unit having a syndiotacticity of 75% or more, preferably 85% or more in terms of a racemic diad or 30% or more, preferably 50% or more in terms of a racemic pentad in a chain of a styrenic repeating unit.

In the styrenic polymers of the present invention having a syndiotactic structure, the number average molecular weight (Mn) and the weight average molecular weight (Mw) have to satisfy the following equations:

$$5000 \leq Mn \leq 10000000 \quad (2)$$

$$Mw/Mn \leq 1.5 \quad (3)$$

In the styrenic polymer having a syndiotactic structure obtained in the present invention, the number average molecular weight (Mn) is preferably 5,000 to 10,000,000, more preferably 10,000 to 5,000,000, further preferably 15,000 to 2,000,000 and particularly preferably 15,000 to 800,000. If the molecular weight is too small, the physical properties as a polymer become so unsatisfactory that the mechanical strength is reduced. On the other hand, if the molecular weight is too large, caused is the problem that molding becomes difficult or it becomes difficult to synthesize the end functionalized polymer or synthesize the block copolymer.

A molecular weight distribution (Mw/Mn) which is a ratio of a weight average molecular weight (Mw) to a number average molecular weight (Mn) in the styrenic polymer having a syndiotactic structure of the present invention is essentially 1.5 or less, preferably 1.45 or less. If the molecular weight distribution is too broad, caused is the problem that the physical properties such as abrasion resistance are reduced or it becomes difficult to synthesize the end functionalized polymer or synthesize the block copolymer, and therefore it is not preferred.

Next, the hydroxystyrenic polymers among the syndiotactic styrenic polymers described above having the structural unit represented by Formula (1) are useful, and the present invention includes the above polymer and the process for the preparation of the same.

The hydroxystyrenic polymers of the present invention have a syndiotacticity of a high degree in a stereoregularity thereof, and it is a polymer having usually a structural unit represented by Formula (9):

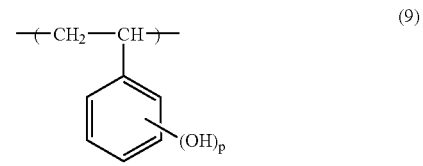

(wherein p represents an integer of 1 to 3) and a number average molecular weight of 600 or more. It has preferably a syndiotactic structure in which a tacticity thereof is 30% or more in terms of a racemic pentad determined by $^{13}$C-NMR.

The syndiotactic hydroxystyrenic polymer according to the present invention means a polymer having a syndiotacticity of preferably 75% or more, more preferably 85% or more in terms of a racemic diad or preferably 30% or more, more preferably 50% or more, particularly preferably 70% or more and most preferably 85% or more in terms of a racemic pentad in a chain of a repetitive unit of hydroxystyrenes. However, a degree of the syndiotacticity is a little varied depending on the kind of the substituent.

Further, the hydroxystyrenic polymer of the present invention desirably has a molecular weight in a range of 600 or more, preferably 1,000 to 2,000,000, more preferably 2,000 to 1,500,000 and particularly preferably 5,000 to 1,000,000 in terms of a number average molecular weight. If the molecular weight is too small, the physical properties as a polymer become so unsatisfactory that the mechanical strength is reduced. On the other hand, if the molecular weight is too large, caused is the problem that molding becomes difficult.

The molecular weight distribution shall not specifically be restricted, and the molecular weight distribution (Mw/Mn) which is a ratio of a weight average molecular weight (Mw) to a number average molecular weight (Mn) in the syndiotactic hydroxystyrenic polymers of the present invention falls preferably in a range of 15 or less, more preferably 10 or less, further preferably 3.0 or less, particularly preferably 2.0 or less and most preferably 1.5 or less. If the molecular weight distribution is too broad, caused is the problem that the physical properties are reduced, and therefore it is not preferred.

The hydroxystyrenic polymers of the present invention are produced by bringing the polymer having a specific substituent among the polymers having the structural unit represented by Formula (1) described above into contact with an acid or a base to remove a protective group by deblocking reaction to thereby form a hydroxy group. The polymer having a specific substituent which is a precursor thereof is a polymer comprising at least one structural unit represented by the following Formula (11):

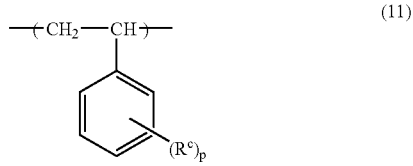

($R^c$ represents a trialkylsilyloxy group having 3 to 30 carbon atoms, an alkoxy group having 4 to 31 carbon atoms or a trialkylgermaniumoxy group having 3 to 30 carbon atoms; p represents an integer of 1 to 3, and when p is plural, $R^c$'s may be the same or different). Especially, $R^c$ is preferably a trialkylsilyloxy group.

The trialkylsilyloxystyrenic polymers of the present invention are preferably a polymer which comprises a structural unit represented by the following Formula (7):

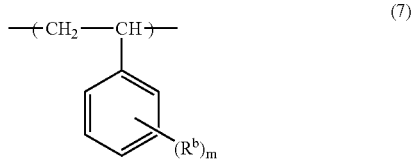

(wherein $R^b$ represents a trialkylsilyloxy group having 3 to 30 carbon atoms; n represents an integer of 1 to 3; and when n is plural, $R^b$'s may be the same or different) and which has a number average molecular weight of 600 or more, and it has preferably a syndiotactic structure in which a tacticity thereof is 30% or more in terms of a racemic pentad determined by $^{13}$C-NMR.

The trialkylsilyloxystyrenic polymer having a syndiotacticity of a high degree according to the present invention means a polymer having a syndiotacticity of preferably 75% or more, more preferably 85% or more and most preferably 90% or more in terms of a racemic diad or preferably 30% or more, more preferably 50% or more, particularly preferably 70% or more and most preferably 80% or more in terms of a racemic pentad in a chain of a repeating unit of trialkylsilyloxystyrenes as shown in Formula (7) described above. However, a degree of the syndiotacticity is a little varied depending on the kind of the substituent.

Further, the trialkylsilyloxystyrenic polymers of the present invention desirably have a molecular weight in a range of 600 or more, preferably 1,000 to 2,000,000, more preferably 2,000 to 1,500,000 and particularly preferably 5,000 to 1,000,000 in terms of a number average molecular weight. If the molecular weight is too small, the physical properties as a polymer become so unsatisfactory that the mechanical strength is reduced. On the other hand, if the molecular weight is too large, caused is the problem that molding becomes difficult.

The molecular weight distribution shall not specifically be restricted, and the molecular weight distribution (Mw/Mn) which is a ratio of a weight average molecular weight (Mw) to a number average molecular weight (Mn) in the syndiotactic trialkylsilyloxystyrenic polymers falls preferably in a range of 15 or less, more preferably 10 or less, further preferably 3.0 or less, particularly preferably 2.0 or less and most preferably 1.5 or less. If the molecular weight distribution is too broad, caused is the problem that the physical properties are reduced, and therefore it is not preferred.

The weight average molecular weight (Mw), the number average molecular weight (Mn) and the molecular weight distribution (Mw/Mn) in the syndiotactic trialkylsilyloxystyrenic polymer according to the present invention mean molecular weights and a molecular weight distribution obtained by measuring by means of gel permeation chromatography using an RI detector which is calibrated with monodisperse standard polystyrenes.

Next, the syndiotactic styrenic block copolymer of the present invention can advantageously be used for obtaining a modified polymer and a graft polymer.

The syndiotactic styrenic block copolymer of the present invention comprises the polymer segment (I) comprising at least one structural unit (repetitive unit) represented by Formula (12) described above and the polymer segment (II) comprising at least one structural unit (repetitive unit) represented by Formula (13) described above:

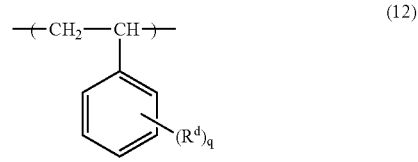

(wherein $R^d$ represents a methyl group, and q represents an integer of 1 to 5)

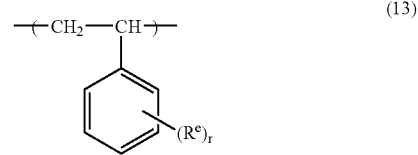

(wherein $R^e$ represents a hydrogen atom, a hydrocarbon group having 1 to 30 carbon atoms or a substituent containing at least one atom selected from the group consisting of an oxygen atom, a nitrogen atom, a sulfur atom, a phosphorus atom, a selenium atom, a silicon atom, a tin atom and a germanium atom; and r represents an integer of 0 to 5, provided that when r is plural, respective $R^e$ may be the same or different).

A syndiotacticity of the syndiotactic styrenic block copolymer of the present invention shows a syndiotacticity of 75% or more, more preferably 85% or more and most preferably 90% or more in terms of a racemic diad or 30% or more, preferably 50% or more, more preferably 70% or more and particularly preferably 80% or more in terms of a racemic pentad in the polymer segments (I) and (II) each. However, a degree of the syndiotacticity is a little varied depending on the kind of the substituent.

Further, the polymer segment (I) represented by Formula (12) described above in the syndiotactic styrenic block copolymer of the present invention has a molecular weight falling in a range of preferably 1,000 to 10,000,000, more preferably 2,000 to 5,000,000 and particularly preferably 5,000 to 1,000,000 in terms of a number average molecular weight. If the molecular weight is too small, the physical properties as a polymer become so unsatisfactory that the mechanical strength is reduced. On the other hand, if the molecular weight is too large, caused is the problem that molding becomes difficult. With respect to the molecular weight distribution, the molecular weight distribution (Mw/Mn) which is a ratio of a weight average molecular weight (Mw) to a number average molecular weight (Mn) in the polymer segment (I) represented by Formula (12) described above is preferably in a range of 2.5 or less, more preferably 2.0 or less and most preferably 1.5 or less. If the molecular weight distribution is too broad, caused is the problem that the physical properties are reduced, and therefore it is not preferred.

On the other hand, the syndiotactic styrenic block copolymer of the present invention desirably has a molecular weight in a range of preferably 1,200 to 20,000,000, more preferably 3,000 to 10,000,000 and particularly preferably 8,000 to 2,000,000 in terms of a number average molecular weight. If the molecular weight is too small, the physical properties as a polymer become so unsatisfactory that the mechanical strength is reduced. On the other hand, if the molecular weight is too large, caused is the problem that molding becomes difficult. With respect to the molecular weight distribution, the molecular weight distribution (Mw/Mn) which is a ratio of a weight average molecular weight (Mw) to a number average molecular weight (Mn) in the polymer segment (I) represented by Formula (12) described above is preferably in a range of 2.5 or less, more preferably 2.0 or less and most preferably 1.5 or less. If the molecular weight distribution is too broad, caused is the problem that the physical properties are reduced, and therefore it is not preferred.

The syndiotactic styrenic polymer and copolymer of the present invention are not only the polymers comprised of one kind of structural unit, but also the polymers comprised of two or more kinds of structural units, and therefore they include homopolymers, two-component copolymers and multi-component copolymers such as terpolymer and quadripolymer.

In the syndiotactic styrenic (co)polymer of the present invention, the structural units bonded thereto are of a syndiotactic structure each other (cosyndiotactic structure) not only in one kind of structural unit but also in one two or more kinds of the structural units. The copolymers constituted by these structural units are of various embodiments effected by block copolymerization, random copolymerization and alternate copolymerization.

The syndiotactic styrenic (co)polymer described above according to the present invention may be a mixture with a styrenic polymer having an isotactic or atactic structure or a polymer in which a styrenic polymer having an atactic structure is incorporated into a polymer chain as long as the syndiotacticity falls in the range described above.

The specific examples of the monomer represented by Formula (6) or (19) providing the respective structural units in the syndiotactic styrenic (co)polymer of the present invention include styrene, alkylstyrenes such as p-methylstyrene, m-methylstyrene and p-tertiary butylstyrene; halogenated styrenes such as p-chlorostyrene, p-bromostyrene and p-fluorostyrene: arylstyrenes such as vinylbiphenyls such as 4-vinylbiphenyl; vinylphenylnaphthalenes such as 1-(4-vinylphenyl)naphthalene and 2-(4-vinylphenyl)naphthalene; vinylanthracenes such as 1-(4-vinylphenyl)anthracene and 2-(4-vinylphenyl)anthracene; vinylphenylphenanthrenes such as 1-(4-vinylphenyl)phenanthrene and 2-(4-vinylphenyl)phenanthrene; vinylphenylpyrenes such as 1-(4-vinylphenyl)pyrene and 2-(4-vinylphenyl)pyrene; vinylalkylbiphenyls such as 4-vinyl-4'-methylbiphenyl and 4-vinyl-3'-methylbiphenyl; halogenated vinylbiphenyls such as 4-vinyl-4'-chlorobiphenyl, 4-vinyl-3'-chlorobiphenyl, 4-vinyl-4'-bromobiphenyl and 4-vinyl-3'-bromobiphenyl; alkoxybiphenyls such as 4-vinyl-4'-methoxybiphenyl and 4-vinyl-3'-methoxybiphenyl; alkoxycarbonylvinylbiphenyls such as 4-vinyl-4'-methoxycarbonylbiphenyl; alkoxyalkylvinylbiphenyls such as 4-vinyl-4'-methoxymethylbiphenyl; trialkylsilylvinylbiphenyls such as 4-vinyl-4'-trimethylsilylbiphenyl; trialkylstannylvinylbiphenyls such as 4-vinyl-4'-methylstannylbiphenyl; trialkylsilylmethylvinylbiphenyls such as 4-vinyl-4'-trimethylsilylmethylbiphenyl; trialkylstannylmethylvinylbiphenyls such as 4-vinyl-4'-trimethylstannylmethylbiphenyl: halogen-substituted alkylstyrenes such as p-chloroethylstyrene; alkoxystyrenes such as p-methoxystyrene; alkoxycarbonylstyrenes such as p-methoxycarbonylstyrene; acyloxystyrenes such as acetyloxystyrene and benzoyloxystyrene; alkyl ether styrenes such as p-vinylbenzyl propyl ether; alkylsilylstyrenes such as p-trimethylsilylstyrene; alkylstannylstyrenes such as p-trimethylstannylstyrene; ethyl vinylbenzenesulfonate, vinylbenzyl dimethoxy phosphite and vinylstyrenes such as p-vinylstyrene.

The specific examples of the monomer represented by Formula (10) providing the structural unit represented by Formula (11) include p-triisopropylsilyloxystyrene, m-triisopropylsilyloxystyrene, p-tri-n-propylsilyloxystyrene, m-tri-n-propylsilyloxystyrene, p-t-butyldimethylsilyloxystyrene, m-t-butyldimethylsilyloxystyrene, p-isopropyldimethylsilyloxystyrene, m-isopropyldimethylsilyloxystyrene, p-triethylsilyloxystyrene, m-triethylsilyloxystyrene, p-trimethylsilyloxystyrene and m-trimethylsilyloxystyrene each of which can be given as the example of the monomer represented by Formula (8), and in addition thereto, p-triisopropylmethyloxystyrene, m-triisopropylmethyloxystyrene, p-tri-n-propylmethyloxystyrene, m-tri-n-propylmethyloxystyrene, p-t-butyldimethylmethyloxystyrene, m-t-butyldimethylmethyloxystyrene, p-isopropyldimethylmethyloxystyrene, m-isopropyldimethylmethyloxystyrene, p-triphenylmethyloxystyrene, p-triethylmethyloxystyrene, m-triethylmethyloxystyrene, p-t-butoxystyrene, m-t-butoxystyrene, p-triisopropylgermaniumoxystyrene, m-triisopropylgermaniumoxystyrene, p-tri-n-propylgermaniumoxystyrene, m-tri-n-propylgermaniumoxystyrene, p-t-butyldimethylgermaniumoxystyrene, m-t-butyldimethylgermaniumoxystyrene, p-isopropyldimethylgermaniumoxystyrene, m-isopropyldimethylgermaniumoxystyrene, p-triethylgermaniumoxystyrene, m-triethylgermaniumoxystyrene, p-trimethylgermaniumoxystyrene and m-trimethylgermaniumoxystyrene.

Among them, the particularly suited monomers are the monomers in which $R^c$ in Formula (10) has 5 or more carbon atoms from the viewpoint of narrowing the molecular weight distribution.

In particular, the most suited monomers among the monomers represented by Formula (8) are p-t-butyldimethylsilyloxystyrene and p-triisopropylsilyloxystyrene represented by the following Formula (26), and, the p-triisopropylsilyloxystyrene mono mer is included as well in one aspect of the present invention:

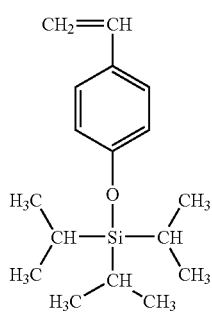
(26)

Publicly known methods disclosed in Eur. Polym. J., vol. 11, p. 653 (1975), Makromol. Chem. Rapid Commun., vol. 3, p. 941 (1982), Macromolecules, vol. 26, p. 4995 (1983), Japanese Patent Application Laid-Open No. Sho 59-53506 and Japanese Patent Application Laid-Open No. Hei 4-356505 can suitably be used as a production process for the monomer represented by Formula (10) used in the present invention and a refining method for the same.

Only one kind of the monomers represented by the respective formulas described above may be used for the respective segments in the respective syndiotactic styrenic polymers and block copolymers or two or more kinds thereof may be used in combination.

In this case, the polymers which are the precursors of the hydroxystyrenic polymers and the trialkylsilyloxystyrenic polymers are prepared by polymerizing the monomers represented by Formula (8) and Formula (10), and may be copolymerized with the monomer represented by Formula (6) which is different from them, as long as the effects of the present invention are not damaged. A using amount thereof is varied depending on uses of the polymers and can not univocally be set up, and it is preferably 45 mole % or less, particularly preferably 0.14 to 30 mole % based on the whole monomers.

Further, in the present invention, the styrenic polymers described above may be copolymerized, if necessary, with other monomers copolymerizable with the styrenic monomers.

In this case, the other monomers copolymerizable with the styrenic monomers include olefins such as ethylene, propylene and 1-butene, cyclic olefins such as cyclopentene and 2-norbornene, conjugate dienes such as 1,3-butadiene, 2-methyl-1,3-butadiene, 2,3-dimethyl-1,3-butadiene, 2-chloro-1,3-butadiene, 1,3-pentadiene and 1,3-hexadiene, non-conjugate dienes such as 1,5-hexadiene, 1,6-heptadiene, 1,7-octadiene, dicyclopentadiene and 5-ethylidene-2-norbornene and (meth)acrylic acid esters such as methyl methacrylate and methyl acrylate.

A using amount thereof is varied depending on uses of the polymers of the present invention and can not univocally be set up, and it is preferably 45 mole % or less, particularly preferably 0.1 to 30 mole % based on the whole monomers.

The highly syndiotactic styrenic polymer according to the present invention can very efficiently be produced by using a catalyst shown below. That is, in the process of the present invention, used as the catalyst components are at least one transition metal compound selected from the following compounds of the component (A) represented by the following Formulas (4) and (5) and at least one co-catalyst selected from the following (a) to (d) of the component (B), and the reaction product thereof is used as a principal catalyst.

Various compounds can be used as the transition metal of the component (A), and usually it is preferably at least one compound selected from the group consisting of the transition metal compounds represented by Formulas (4) and (5):

$$MR^1_x R^2_y R^3_z X^1_{4-(x+y+z)} \quad (4)$$

$$MR^1_u R^2_v X^1_{3-(u+v)} \quad (5)$$

$R^1$, $R^2$ and $R^3$ in these Formulas (4) and (5) each represent a hydrogen atom, an alkyl group having 1 to 20 carbon atoms (to be specific, methyl, ethyl, propyl, butyl, amyl, isoamyl, isobutyl, octyl and 2-ethylhexyl), an aryl group, an alkylaryl group, an arylalkyl group (to be specific, phenyl, tolyl, xylyl and benzyl) and an aryloxy group (to be specific, phenoxy) each of which has 6 to 20 carbon atoms, an acyloxy group having 1 to 20 carbon atoms (to be specific, heptadecylcarbonyloxy), an alkoxy group having 1 to 20 carbon atoms (to be specific, methoxy, ethoxy, propoxy, butoxy, amyloxy, hexyloxy and 2-ethylhexyloxy), a thioalkoxy group having 1 to 20 carbon atoms (to be specific, thiomethoxy), a thioaryloxy group having 6 to 20 carbon atoms (to be specific, thiophenoxy), an amino group, a cyclopentadienyl group, a substituted cyclopentadienyl group (to be specific, methylcyclopentadienyl, 1,2-dimethylcyclopentadienyl and pentamethylcyclopentadienyl), an indenyl group, a substituted indenyl group, a fluorenyl group or a substituted fluorenyl group.

M represents a transition metal selected from the group consisting of titanium (Ti), zirconium (Zr), hafnium (Hf) and vanadium (V); $X^1$ represents a halogen atom (to be specific, chlorine, bromine, iodine and fluorine); these $R^1$, $R^2$ and $R^3$ may be the same or different; x, y and z each represent an integer of 0 to 4, and u and v each represent an integer of 0 to 3.

Among these the transition metal compounds, the most suitably used compound is the titanium compound in terms of polymerization activity. Further, the suited titanium compound includes a mono(cyclopentadienyl)titanium compound, a mono(indenyl)titanium compound and a mono (fluorenyl)titanium compound each represented by Formula (27):

$$TiR^4XYZ \quad (27)$$

(wherein $R^4$ represents a cyclopentadienyl group, a substituted cyclopentadienyl group, an indenyl group, a substituted indenyl group or a fluorenyl group; X, Y and Z represent independently of each other a hydrogen atom, an alkyl group having 1 to 12 carbon atoms, an alkoxy group having 1 to 12 carbon atoms, a thioalkoxy group having 1 to 20 carbon atoms, an aryl group having 6 to 20 carbon atoms, an aryloxy group having 6 to 20 carbon atoms, a thioaryloxy group having 6 to 20 carbon atoms, an arylalkyl group having 6 to 20 carbon atoms or a halogen atom).

The substituted cyclopentadienyl group represented by $R^4$ in this formula includes, for example, a cyclopentadienyl group substituted with at least one alkyl group having 1 to 6 carbon atoms, to be specific, methylcyclopentadienyl, 1,3-dimethylcyclopentadienyl, 1,2,4-trimethylcyclopentadienyl, 1,2,3,4-tetramethylcyclopentadienyl, trimethylsilylcyclopentadienyl, 1,3-di(trimethylsilyl)cyclopentadienyl, tertiary butylcyclopentadienyl, 1,3-di(tertiary butyl)cyclopentadienyl and pentamethylcyclopentadienyl.

Further, X, Y and Z represent independently of each other a hydrogen atom, an alkyl group having 1 to 12 carbon atoms (to be specific, methyl, ethyl, propyl, n-butyl, isobutyl, amyl, isoamyl, octyl and 2-ethylhexyl), an alkoxy group having 1 to 12 carbon atoms (to be specific, methoxy, ethoxy, propoxy, butoxy, amyloxy, hexyloxy, octyloxy and 2-ethylhexyloxy), a thioalkoxy group having 1 to 12 carbon atoms (to be specific, thiomethoxy), an aryl group having 6 to 20 carbon atoms (to be specific, phenyl and naphthyl), an aryloxy group having 6 to 20 carbon atoms (to be specific, phenoxy), a thioaryloxy group having 6 to 20 carbon atoms (to be specific, thiophenoxy), an arylalkyl group having 6 to 20 carbon atoms (to be specific, benzyl) or a halogen atom (to be specific, chlorine, bromine, iodine and fluorine).

The specific examples of such titanium compound represented by Formula (27) include cyclopentadienyltrimethyltitanium, cyclopentadienyltriethyltitanium, cyclopentadienyltripropyltitanium, cyclopentadienyltributyltitanium, methylcyclopentadienyltrimethyltitanium, 1,2-dimethylcyclopentadienyltrimethyltitanium, 1,2,4-trimethylcyclopentadienyltrimethyltitanium, 1,2,3,4-tetramethylcyclopentadienyltrimethyltitanium, pentamethylcyclopentadienyltrimethyltitanium, pentamethylcyclopentadienyltriethyltitanium, pentamethylcyclopentadienyltripropyltitanium, pentamethylcyclopentadienyltributyltitanium, cyclopentadienylmethyltitanium dichloride, cyclopentadienylethyltitanium dichloride, pentamethylcyclopentadienylmethyltitanium dichloride, pentamethylcyclopentadienylethyltitanium dichloride, cyclopentadienyldimethyltitanium monochloride, cyclopentadienyldiethyltitanium monochloride, cyclopentadienyltitanium trimethoxide, cyclopentadienyltitanium triethoxide, cyclopentadienyltitanium tripropoxide, cyclopentadienyltitanium triphenoxide, pentamethylcyclopentadienyltitanium trimethoxide, pentamethylcyclopentadienyltitanium triethoxide, pentamethylcyclopentadienyltitanium tripropoxide, pentamethylcyclopentadienyltitanium tributoxide, pentamethylcyclopentadienyltitanium triphenoxide, cyclopentadienyltitanium trichloride, pentamethylcyclopentadienyltitanium trichloride, cyclopentadienylmethoytitanium dichloride, cyclopentadienyldimethoxytitanium chloride, pentamethylcyclopentadienylmethoxytitanium dichloride, cyclopentadienyltribenzyltitanium, pentamethylcyclopentadienylmethyldiethoxytitanium, indenyltitanium trichloride, indenyltitanium trimethoxide, indenyltitanium triethoxide, indenyltrimethyltitanium, indenyltribenzyltitanium, pentamethylcyclopentadienyltitanium trithiomethoxide and pentamethylcyclopentadienyltitanium trithiophenoxide.

Further, a condensed titanium compound represented by Formula (28) may be used as the titanium compound:

(28)

(wherein $R^5$ and $R^6$ each represent a halogen atom, an alkoxy group or an acyloxy group each of which has 1 to 20 carbon atoms, and k represents an integer of 2 to 20).

The trivalent titanium compound represented by Formula (28) described above includes typically titanium trihalides such as titanium trichloride and cyclopentadienyltitanium compounds such as cyclopentadienyltitanium dichloride. In addition thereto, it includes compounds obtained by reducing tetravalent titanium compounds. These trivalent titanium compounds may be used in the form of complexes formed with esters and ethers.

The zirconium compound as the transition metal compound includes tetrabenzylzirconium, zirconium tetraethoxide and zirconium tetrabutoxide; the hafnium compound includes tetrabenzylhafnium, hafnium tetraethoxide and hafnium tetrabutoxide; and the vanadium. compound includes vanadyl bisacetylacetonate, vanadyl triacetylacetonate, triethoxyvanadyl and tripropoxyvanadyl. Among these transition metal compounds, the titanium compounds are particularly suited.

The titanium compounds and the like described above may be used in the form of complexes formed with esters and ethers.

In addition thereto, the transition metal compound which is the component (A) includes transition metal compounds having two ligands having conjugated π electrons, for example, at least one compound selected from the group consisting of transition metal compounds represented by Formula (29):

(29)

(wherein $M^1$ represents titanium, zirconium or hafnium; $R^7$ and $R^8$ each represent a cyclopentadienyl group, a substituted cyclopentadienyl group, an indenyl group, a substituted indenyl group, a fluorenyl group or a substituted fluorenyl group; $R^9$ and $R^{10}$ each represent a hydrogen atom, a halogen atom, a hydrocarbon group having 1 to 20 carbon atoms, an alkoxy group having 1 to 20 carbon atoms, an aryloxy group having 6 to 20 carbon atoms, an amino group or a thioalkoxy group having 1 to 20 carbon atoms, provided that $R^7$ and $R^8$ may be cross-linked with a hydrocarbon group having 1 to 5 carbon atoms, an alkylsilyl group having 1 to 20 carbon atoms and 1 to 5 silicon atoms or a germanium-containing hydrocarbon group having 1 to 20 carbon atoms and 1 to 5 germanium atoms).

$R^7$ and $R^8$ in this Formula (29) represent a cyclopentadienyl group, a substituted cyclopentadienyl group (to be specific, methylcyclopentadienyl, 1,3-dimethylcyclopentadienyl, 1,2,4-trimethylcyclopentadienyl, 1,2,3,4-tetramethylcyclopentadienyl, pentamethylcyclopentadienyl, trimethylsilylcyclopentadienyl, 1,3-di(trimethylsilyl)cyclopentadienyl, 1,2,4-tri(i(trimethylsilyl)cyclopentadienyl, tertiary butylcyclopentadienyl, 1,3-di(tertiary butyl)cyclopentadienyl and 1,2,4-tri(tertiary butyl)cyclopentadienyl), an indenyl group, a substituted indenyl group (to be specific, methylindenyl, dimethylindenyl and trimethylindenyl), a fluorenyl group or a substituted fluorenyl group (for example, methylfluorenyl). $R^7$ and $R^8$ may be the same or different. Further, $R^7$ and $R^8$ may be of a structure in which $R^7$ and $R^8$ are cross-linked with an alkylidene group having 1 to 5 carbon atoms (to be specific, methine, ethylidene, propylidene and dimethylcarbyl) or an alkylsilyl group having 1 to 20 carbon atoms and 1 to 5 silicon atoms (to be specific, dimethylsilyl, diethylsilyl and dibenzylsilyl).

On the other hand, $R^9$ and $R^{10}$ are as described above, and to be more specific, they represent independently of each other a hydrogen atom, a halogen atom, an alkyl group having 1 to 20 carbon atoms (to be specific, methyl, ethyl, propyl, n-butyl, isobutyl, amyl, isoamyl, octyl and 2-ethylhexyl), an aryl group having 6 to 20 carbon atoms (to be specific, phenyl and naphthyl), an arylalkyl group having 7 to 20 carbon atoms (to be specific, benzyl), an alkoxy group having 1 to 20 carbon atoms (to be specific, methoxy, ethoxy, propoxy, butoxy, amyloxy, hexyloxy, octyloxy and 2-ethylhexyloxy), an aryloxy group having 6 to 20 carbon atoms (to be specific, phenoxy), an amino group and a thioalkoxy group having 1 to 20 carbon atoms.

The specific examples of such transition metal compound represented by Formula (29) include biscyclopentadienyltitanium dimethyl, bis(methylcyclopentadienyl)titanium dimethyl, bis(tertiary butylcyclopentadienyl)titanium dimethyl, bis(trimethylsilylcyclopentadienyl)titanium dimethyl, bisindenyltitanium dimethyl, methylenebiscyclopentadienyltitanium dimethyl, methylenebisindenyltitanium dimethyl, ethylidenebisindenyltitanium dimethyl and dimethylsilylbisindenyltitanium dimethyl.

Also, the zirconium compound includes ethylidenebiscyclopentadienylzirconium dimethoxide and dimethylsilylbiscyclopentadienylzirconium dimethoxide. Further, the hafnium compound includes ethylidenebisyclopentadienylhafnium dimethoxide and dimethylsilylbiscyclopentadienylhafnium dimethoxide. Among them, the titanium compounds are particularly preferred. Further, in addition to these combinations, they may be bidentate coordiantion type complexes such as 2,2'-thiobis(4-methyl-6-t-butylphenyl) titanium diisopropoxide and 2,2'-thiobis(4-methyl-6-t-butylphenyl)titanium dimethoxide. Among these transition metal compounds, the transition metal compounds having one π ligand represented by Formula (27) are particularly suitably used.

In the catalyst for polymerization used in the present invention, the transition metal compounds of the component (A) described above may be used alone or in combination of two or more kinds thereof.

The catalyst in the present invention comprises principally the reaction product of the transition metal compound which is the component (A) described above and the component (B) which is a co-catalyst, and at least one selected from the following (a) to (d) is used as the component (B) which is a co-catalyst:
(a) an organic aluminumoxy compound,
(b) an ionic compound which can be reacted with the transition metal compound described above to form a cationic transition metal compound,
(c) a Lewis acid compound which can be reacted with the transition metal compound described above to form a cationic transition metal compound, and
(d) an organic metal compound of a first, second and thirteenth group elemental metal in the periodic table.

First, the organic aluminumoxy compound of (a) is preferably a linear or cyclic polymer represented by the following Formula (30), and it is so-called aluminoxane:

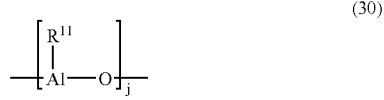

(30)

(wherein $R^{11}$ is a hydrocarbon group having 1 to 10 carbon atoms, and $R^{11}$ may be substituted with a halogen atom and/or a $R^{12}O$ group).

The specific examples of $R^{11}$ or $R^{12}$ include an alkyl group such as methyl, ethyl, propyl and isobutyl, and among them, methyl is preferred. The term j represents a degree of polymerization, and it desirably is in a range of preferably 5 or more, more preferably 10 to 100 and most preferably 10 to 50. If the degree of polymerization j is less than 5, the polymerization activity is reduced, and therefore it is not preferred. If it is larger than 100, caused are the problems that the polymerization activity is reduced and that deashing treatment becomes difficult, and therefore it is not preferred.

The ionic compound of (b) which can be reacted with the transition metal compound represented by Formula (4) and/or Formula (5) described above to form a cationic transition metal compound includes non-coordinate anion and cation.

The non-coordinate anion includes, for example, tetra (phenyl)borate, tetra(fluorophenyl)borate, tetrakis (difluorophenyl)borate, tetrakis(trifluorophenyl)borate, tetrakis(tetrafluorophenyl)borate, tetrakis (pentafluorophenyl)borate, tetrakis (tetrafluoromethylphenyl)borate, tetra(tolyl) borate, tetra (xylyl)borate, triphenylpentafluorophenyl borate and tris (pentafluorophenyl)phenyl borate.

Among these non-coordinate anions, tetrakis (pentafluorophenyl)borate is particularly preferred. The specific examples thereof include, for example, triphenylcarbeniumtetrakis(pentafluorophenyl) borate, 4,4', 4"-tri(methoxyphenyl)carbeniumtetrakis (pentafluorophenyl) borate, tri(tolyl)carbeniumtetrakis (pentafluorophenyl) borate, 4,4',4"-tri(chlorophenyl) carbeniumtetrakis(pentafluorophenyl) borate, triphenylsilyltetrakis(pentafluorophenyl)borate, trimethoxysilyltetrakis(pentafluorophenyl)borate, tri (thioisopropyl)silyltetrakis(pentafluorophenyl)borate, trimethylsilyltetrakis(pentafluorophenyl)borate, 4,4',4"-tri (methoxyphenyl)silyltetrakis(pentafluorophenyl)borate, tri (tolyl)silyltetrakis(pentafluorophenyl)borate and 4,4',4"-tri (chlorophenyl)silyltetrakis(pentafluorophenyl) borate.

The cation includes a) carbonium cation, b) oxonium cation, c) ammonium cation, d) phosphonium cation and e) ferrocenium cation having transition metal.

The specific examples of a) the carbonium cation include tri-substituted carbonium cation such as triphenylcarbonium cation and tri-substituted phenylcarbonium cation. The specific examples of the tri-substituted phenylcarbonium cation include tri(methylphenyl)carbonium cation and tri (dimethylphenyl)carbonium cation.

The specific examples of b) the oxonium cation include hydroxonium cation $OH^{3+}$, alkyloxonium cation such as methyloxonium cation $CH_3OH^{2+}$, dialkyloxonium cation such as dimethyloxonium cation $(CH_3)_2OH^+$ and trialkyloxonium cation such as trimethyloxonium cation $(CH_3)_3O^+$ and triethyloxonium cation $(C_2H_5)_3O^+$.

The specific examples of c) the ammonium cation include trialkylammonium cation such as trimethylammonium cation, triethylammonium cation, tripropylammonium cation and tributylammonium cation, N,N-dialkylanilinium cation such as N,N-diethylanilinium cation and N,N-2,4,6-pentamethylanilinium cation and dialkylammonium cation such as di(isopropyl)ammonium cation and dicyclohexylammonium cation.

The specific examples of d) the phosphonium cation include triarylphosphonium cation such as triphenylphosphonium cation, tri(methylphenyl)phosphonium cation and tri(dimethylphenyl)phosphonium cation.

In these ionic compounds of (b), capable of being used is a combination of the compounds each optionally selected from the non-coordinate anions and the cations which have been given above as the examples thereof. Among the compounds described above, capable of being more preferably used are the ionic compounds such as triphenylcarboniumtetra(pentafluorophenyl)borate, N,N-dimethylaniliniumtetra(pentafluorophenyl)borate and 1,1'-dimethylferroceniumtetra(pentafluorophenyl)borate.

The specific examples of the Lewis acid compound of (c) which can be reacted with the transition metal compounds represented by Formula (4) and/or Formula (5) described above to form a cationic transition metal compound include tris(pentafluorophenyl)boron, tris(monofluorophenyl)boron, tris(difluorophenyl)boron and triphenylboron.

The organic metal compound (d) of a first, second and thirteenth group elemental metal in the periodic table includes not only organic metal compounds in a narrow sense but also organic metal halogen compounds and organic metal hydride compounds of a first, second and thirteenth group elemental metal in the periodic table.

first group elemental metal in the periodic table includes Li and Na, second group elemental metal in the periodic table includes Mg and Be; and thirteenth group elemental metal in the periodic table includes Al and B.

Among them, the preferred elemental metals are Li, Mg and Al, and Al is particularly preferred.

The organic metal compound of (d) includes, for example, methyllithium, butyllithium, phenyllithium, dibutylmagnesium, trimethylaluminum, triethylaluminum, triisobutylaluminum, trihexylaluminum and trioctylaluminum, and trialkylaluminum are preferred.

The organic metal halogen compound of (d) includes, for example, ethylmagnesium chloride, butylmagnesium chloride, dimethylaluminum chloride, diethylaluminum chloride, sesquiethylalminum chloride and ethylalminum dichloride.

The organic metal hydride compound of (d) includes, for example, diethylaluminum hydride and sesquiethylalminum hydride.

In the present invention, the compounds (a) to (d) may be used as the co-catalyst alone or in combination. The preferred co-catalyst is (a) alone, (c) alone and combinations of (a) with (d), (b) with (d) and (c) with (d). The combinations of (b) with (d) and (c) with (d) are particularly preferred for the purpose of obtaining the polymer having a narrow molecular weight distribution.

The catalyst for producing the syndiotactic styrene base (co)polymer used in the present invention comprises the reaction product of the component (A) and the component (B) described above as the principal component. In addition thereto, other catalyst components may be added as long as the effects of the present invention are not damaged. A blending proportion of the components (A) and (B) contained in the catalyst of the present invention is varied depending on the kind of the compounds and various polymerization conditions, and can not univocally be determined, and usually a mole ratio of the respective compound (a), (b), (c) or (d) of the component (B) which is independently of each other determined to the component (A) is preferably in the following range.

(a) A mole ratio of aluminum contained in the organic aluminumoxy compound to the transition metal compound (A) is usually 1 to 1,000,000, preferably 10 to 50,000 and more preferably 130 to 5,000.

(b) A mole ratio of the ionic compound to the transition metal compound (A) is usually 0.01 to 100, preferably 0.1 to 10.

(C) A mole ratio of the Lewis acid compound to the transition metal compound (A) is usually 0.01 to 100, preferably 0.1 to 10. When the Lewis acid compound is used as the co-catalyst component, the organic metal compound of a first, second and thirteenth group elemental metal in the periodic table is preferably used in combination.

(d) When the organic metal compound is used, a mole ratio of the organic metal compound (d) to the transition metal compound (A) is usually 0.1 to 10,000, preferably 1 to 1000. If it deviates from the range described above, the polymerization activity is reduced, and therefore it is not preferred.

In the present invention, a metal hydride compound may further be used in combination with the organic metal compound, the organic metal halide compound and the organic metal hydride compound described above each of which is the organic metal compound of a first, second and thirteenth group elemental metal in the periodic table to polymerize the styrenic monomer.

The metal hydride compound includes, for example, NaH, LiH, $CaH_2$, $LiAlH_4$ and $NaBH_4$. The organic metal compound, the organic metal halide compound and the organic metal hydride compound containing an elemental metal of a first, second and thirteenth group elemental metal in the periodic table as a principal elemental metal, include those described above.

In the present invention, capable of being used is a catalyst prepared by carrying the transition metal compound represented by Formula (4) and/or Formula (5) alone or in combination thereof with at least one promoter selected from the compounds (a) to (d) described above on a carrier. The carrier includes an inorganic compound or an organic high molecular compound. Inorganic oxides, inorganic chlorides and inorganic hydroxides are preferred as the inorganic compound, and a small amount of carbonates and sulfates may be contained therein. Preferred are inorganic oxides such as silica, alumina, magnesia, titania, zirconia and calcia and inorganic chlorides such as magnesium chloride. These inorganic compound are preferably in the form of porous fine particles having an average particle diameter of 5 to 150 μm and a specific surface area of 2 to 800 $m^2/g$, and they can be used after subjecting to heat treatment at 100 to 800° C.

The organic high molecular compound is preferably a compound having an aromatic ring, a substituted aromatic ring or a functional group such as a hydroxy group, a carboxyl group, an ester group and a halogen atom on a side chain. Capable of being given as the specific examples of the organic high molecular compound are α-olefin homopolymers and α-olefin copolymers having functional groups obtained by chemically modifying polymers having a unit such as ethylene, propylene and butene, polymers having a unit such as acrylic acid, methacrylic acid, vinyl chloride, vinyl alcohol, styrene and divinylbenzene and chemically modified products thereof. These organic high molecular compounds are used in the form of spherical particles having an average particle diameter of 5 to 250 μm. Carrying the transition metal compound and the co-catalyst on a carrier makes it possible to prevent contamination caused by sticking of the catalyst on a polymerization vessel.

The syndiotactic styrenic polymers of the present invention can be obtained by the following production process using the styrenic monomer, the transition metal compound and the co-catalyst described above.

In the present invention, a method for polymerizing a styrenic monomer or a styrenic monomer and a monomer copolymerizable therewith shall not specifically be restricted and, for example, the transition metal compound of the component (A) described above and at least one co-catalyst selected from the compounds (a) to (d) described above are used to polymerize at least one styrenic monomer. To be specific, the following methods (I) to (VII) can be applied.

In the following explanation, the component (A) shows the transition metal compound, and the component (B) shows the co-catalyst.

(I) The component (A) and the component (B) are brought in advance into contact and then further brought into contact with a monomer component such as a styrenic monomer to carry out polymerization.
(II) The component (A), the component (B) and a small amount of a styrenic monomer component are brought in advance into contact and then further brought into contact with a monomer component such as the styrenic monomer to carry out polymerization.
(III) The component (A) and the component (B) are mixed and brought into contact with a support to form a supported catalyst, followed by separating it, and a monomer component such as a styrenic monomer is brought into contact with the supported catalyst and polymerized.
(IV) The component (A) and a support are brought into contact and then further brought into contact with the component (B) to form a supported catalyst, followed by separating it, and a monomer component such as a styrenic monomer is brought into contact with the supported catalyst and polymerized.
(V) The component (B) and a support are brought into contact and then further brought into contact with the component (A) to form a supported catalyst, followed by separating it, and a monomer component such as a styrenic monomer is brought into contact with the supported catalyst and polymerized.
(VI) The component (A) is mixed with a monomer component such as a styrenic monomer, and then the component (B) is brought into contact therewith to carry out polymerization.
(VII) The component (B) is mixed with a monomer component such as a styrenic monomer, and then the component (A) is brought into contact therewith to carry out polymerization.

Among the methods (I) to (VII), the methods (I) and (II) are preferred from such a viewpoint that the initiator efficiency and the polymerization activity are elevated and that a molecular weight distribution of the resulting polymer can further be narrowed.

In the production of the syndiotactic styrenic block copolymer of the present invention, step (i); at least one styrenic monomer represented by Formula (18) described above or at least one styrenic monomer represented by Formula (19) is polymerized in the presence of the catalyst prepared by bringing the transition metal compound of the component (A) described above into contact with the component (B) which is at least one co-catalyst selected from the compounds (a) to (d) described above, step (ii); and at least one styrenic monomer represented by either Formula (18) or Formula (19), which is different from the styrenic monomer polymerized in the step (i) described above is polymerized in the presence of the living syndiotactic styrenic polymers obtained in the step (i). To be specific, the polymerization can be carried out by the following methods (I) to (VII).

A monomer component-1 represents at least one styrenic monomer used in the step (i) selected from either one group of the styrenic monomer group represented by Formula (18) or the styrenic monomer group represented by Formula (19) described above, and a monomer component-2 represents at least one styrenic monomer represented by Formula (18) or Formula (19) described above used in the step (ii), which is different from the styrenic monomer used in the step (i).
(I) The component (A) and the component (B) are brought in advance into contact and then further brought into contact with the monomer component-1 to carry out polymerization, and then the monomer component-2 is added thereto to conduct polymerization.
(II) The component (A), the component (B) and a small amount of the monomer component-1 are brought in advance into contact and then further brought into contact with a needed amount of the monomer component-1 to carry out polymerization, and then the monomer component-2 is added thereto to conduct polymerization.
(III) The component (A) and the component (B) are mixed and brought into contact with a support to form a supported catalyst, followed by separating it, and the monomer component-1 is brought into contact with the carried catalyst and polymerized. Then, the monomer component-2 is added thereto to carry out polymerization.
(IV) The component (A) is brought into contact with a support and then further brought into contact with the component (B) to form a supported catalyst, followed by separating it, and the monomer component-1 is brought into contact with the supported catalyst and polymerized. Then, the monomer component-2 is added thereto to conduct polymerization.
(V) The component (B) is brought into contact with a support and then further brought into contact with the component (A) to form a supported catalyst, followed by separating it, and the monomer component-1 is brought into contact with the supported catalyst and polymerized. Then, the monomer component-2 is added thereto to conduct polymerization.
(VI) The component (A) is mixed with the monomer component-1, and then the component (B) is brought into contact therewith to conduct polymerization. Then, the monomer component-2 is added thereto to conduct polymerization.
(VII) The component (B) is mixed with the monomer component-1, and then the component (A) is brought into contact therewith to conduct polymerization. Then, the monomer component-2 is added thereto to conduct polymerization.

Among the methods (I) to (VII), the methods (I) and (II) are preferred from such a viewpoint that the initiator efficiency and the polymerization activity are elevated and that a molecular weight distribution of the resulting polymer can further be narrowed.

In the present invention, the components (A) and (B) each can be used in the form of either a solution or a slurry, but the solution form is preferred in order to obtain the higher polymerization activity. A solvent used for preparing the solution or the slurry is a hydrocarbon solvent such as butane, pentane, hexane, heptane, octane, cyclohexane, mineral oil, benzene, toluene and xylene or a halogenated hydrocarbon solvent such as chloroform, methylene chloride, dichloroethane and chlorobenzene. The preferred solvent is an aromatic hydrocarbon such as toluene and benzene. Two or more kinds of the solvents may be used in a mixture.

In the present invention, the styrenic monomer described above is polymerized in the presence of the catalyst described above, and the polymerization is usually carried out by a solution polymerization method and a slurry polymerization method in an inert solvent and a bulk polymerization method using a monomer as a diluent. Among these methods, the solution polymerization method and the bulk polymerization method are preferred. In this polymerization reaction, the polymerization temperature desirably is usually in a range of −100 to 250° C., preferably −50 to 120° C. and particularly preferably −30 to 70° C.

However, in the case of the polymer having the structural unit represented by Formula (1) described above, the polymerization is carried out at a temperature of usually −50 to 20° C., preferably −40 to 0° C., more preferably −35 to −5° C. and most preferably −35 to −20° C.

If the polymerization temperature is lower than −50° C., the syndiotacticity is lowered, and therefore it is not preferred. On the other hand, if the polymerization temperature is higher than 20° C., the molecular weight distribution (Mw/Mn) is broadened, and therefore it is also not preferred.

In the polymerization reaction according to the present invention, the typical polymerization time is 30 seconds to 36 hours, preferably one minute to 20 hours and more preferably 5 minutes to 10 hours. The optimum time required for forming the desired polymer is varied depending on the temperature, the solvent and the other polymerization conditions used.

The polymerization can be carried out at a lower pressure than atmospheric pressure and a higher pressure than atmospheric pressure. The polymerization is conducted as well at a pressure reduced until the component having the lowest boiling point in the polymerization mixture is vaporized. However, a pressure in the vicinity of atmospheric pressure is preferably used.

The inert solvent used in the polymerization includes aliphatic, alicyclic, aromatic and halogenated aromatic hydrocarbons and mixtures thereof. The inert solvents preferred for the polymerization are $C_4$ to $C_{26}$ alkanes, particularly branched alkanes, toluene, ethylbenzene and mixtures thereof. The solvent is used in an amount suited for providing a monomer concentration of 0.5 to 100% by weight.

Further, polar compounds including ethers such as anisole, diphenyl ether, ethyl ether, diglyme, tetrahydrofuran and dioxane and amines such as triethylamine and tetramethylethylenediamine may be added in a small amount to conduct the polymerization reaction as long as the effects of the present invention are not damaged.

A chain transfer agent can be added as well in order to control a molecular weight of the polymer as long as the effects of the present invention are not damaged. Allenes such as 1,2-butadiene, cyclic dienes such as cyclooctadiene and hydrogen are preferably used as the chain transfer agent.

The polymerization reaction is terminated usually by adding a polymerization terminator to the polymerization system when the prescribed conversion rate is reached. Used as the polymerization terminator are, for example, alcohols such as methanol, ethanol, propanol, butanol and isobutanol, and they may contain acid such as hydrochloric acid. A method for recovering the polymer after terminating the polymerization reaction shall not specifically be restricted, and a steam stripping method and deposition with a poor solvent can be used.

Next, a method for obtaining the hydroxystyrenic polymers represented by Formula (9) described above shall be explained.

In the present invention, the styrenic polymers represented by Formula (11) described above which is produced by the production process described above is brought into contact with an acid or a base in the presence of an organic solvent to carry out deblocking reaction, whereby a hydroxyl group is formed.

The styrenic polymer represented by Formula (11) described above can be used after it is isolated and refined by a conventional method such as a method in which it is deposited using a suitable solvent, for example, such as methanol from the polymerization liquid obtained by the coordination polymerization described above, washed and dried or a method in which a solvent is removed and drying operation such as steam stripping drying or heating drying is employed, or it can be used for the deblocking reaction as it is without carrying out the isolating operation.

The acid used in the present invention includes, for example, hydrogen halides such as hydrogen chloride and hydrogen bromide, mineral acids such as hydrochloric acid, hydrobromic acid, nitric acid, sulfuric acid and phosphoric acid, carboxylic acids such as trichloroacetic acid, trifluoroacetic acid, oxalic acid, acetic acid and malonic acid and organic sulfonic acids such as p-toluenesulfonic acid and trifluoromethylsulfuric acid. Among them, preferred is hydrogen chloride, hydrochloric acid, sulfuric acid, trifluoroacetic acid, p-toluenesulfonic acid or trifluoromethylsulfuric acid.

Further, the base used in the present invention includes, for example, ammonium salts such as tetrabutylammonium fluoride, tetrabutylammonium chloride, tetrabutylammonium bromide, tetrabutylammonium iodide, tetrabutylammonium p-toluenesulfonate, tetrapropylammonium fluoride, tetrapropylammonium chloride, tetrapropylammonium bromide, tetrapropylammonium iodide and tetrapropylammonium p-toluenesulfonate or alkali hydroxides such as sodium hydroxide and potassium hydroxide.

A using amount of the acid or the base is 0.00001 time mole or more based on mole number of the repetitive unit in the styrenic polymers represented by Formula (11) described above, and carboxylic acids such as acetic acid and the like can be used as an organic solvent as well. The using amount falls in a range of preferably 0.00001 to 1000 time mole, more preferably 0.0001 to 100 time mole.

Any solvents can be used as the organic solvent as long as at least either of the styrenic polymers represented by Formula (11) described above and the hydroxystyrenic polymers produced therefrom is dissolved therein, and usually it includes aliphatic or alicyclic hydrocarbons such as n-hexane, n-pentane, n-heptane and cyclohexane; aromatic hydrocarbons such as benzene, toluene, ethylbenzene and cumene; aliphatic or aromatic halogenated compounds such as dichlorometane, chloroform, chlorobenzene and dichlorobenzene; alcohols such as methanol, ethanol, n-propanol, iso-propanol, n-butanol, tert-butanol, amyl alcohol, cyclohexanol and ethylene glycol; ethers such as diethyl ether, diphenyl ether, tetrahydrofuran, 1,4-dioxane, ethylene glycol dimethyl ether and ethylene glycol diethyl ether; ketones such as acetone, ethyl methyl ketone, 2-pentanone, 2-heptanone and acetophenone; nitriles such as acetonitrile and propionitrile; and esters such as ethyl acetate, ethyl propionate and ethyl lactate.

Or, it includes carboxylic acids such as acetic acid and the like used for the deblocking reaction.

These organic solvents may be used alone or in a mixture of two or more kinds thereof. A using amount of these solvents is varied depending on the kind of the solvent used and is usually in a range such that the styrenic polymers represented by Formula (11) described above or the hydroxystyrenic polymers produced therefrom are dissolved at a concentration of 0.005 to 50% by weight, preferably 0.01 to 30% by weight particularly preferably 0.1 to 25% by weight.

A method for carrying out the deblocking reaction in the process of the present invention shall not specifically be restricted and may be any method as long as it is a method in which the styrenic polymer represented by Formula (11) described above or the hydroxystyrenic polymer produced therefrom, the acid or the base and the organic solvent are effectively mixed and brought into contact, and it may be any of a batch method, a semi-batch method and a continuous flow method.

The temperature and the time in the deblocking reaction are varied depending on a concentration and a molecular weight of the styrenic polymer represented by Formula (11) described above, the kind and the amount of the acid or the base and the kind of the organic solvent, and they are not set constant. However, the temperature in the deblocking reaction falls usually in a range of −20 to 200° C., preferably 0 to 150° C. and particularly preferably 15 to 100° C. The time in the deblocking reaction falls usually in a range of 72 hours or shorter, preferably 0.01 to 48 hours and particularly preferably 0.05 to 24 hours. It can be carried out as well, if necessary, at any of reduced pressure, atmospheric pressure and applied pressure. Further, this deblocking reaction can be carried out either under inert gas environment or in the presence of molecular oxygen such as air When an organic solvent having a low solubility such as hydrocarbon is used in, for example, the deblocking reaction, this resulting hydroxystyrenic polymer is deposited in the form of solid during the deblocking reaction, and therefore it can be isolated by conventional separating operation such as filtering and decantation, or when an organic solvent having a high solubility such as alcohol is used, it is uniformly dissolved, and therefore it can be isolated by a conventional method such as a method in which a suitable poor solvent is used for depositing and separating the polymer after carrying out conventional refining operation such as extraction, stripping and ion exchange or without carrying out any refining operation and a method using drying operation such as a desolvent method.

Next, it shall be explained to modify the block copolymer comprising the structural units represented by Formulas (12) and (13) as the segments to produce the block•graft copolymer comprising the structural unit represented by Formula (23).

In the present invention, after preparing the syndiotactic styrenic block copolymer by the process described above (step 1), a part or the whole part of methylstyrene contained in the structural unit thereof is converted into styrene having a halogenated methyl group (step 2), and the polymer is further graft-polymerized with a nitrogen-containing aromatic monomer (step 3), whereby the syndiotactic styrenic block•graft copolymer which is useful for application as a functional material can be prepared.

The syndiotactic styrenic polymer and the syndiotactic styrenic block copolymer each having a halogenated methyl group comprise the structural unit represented by Formula (20).

A process for the preparation of the syndiotactic styrenic polymer and the syndiotactic styrenic block copolymer each comprising the structural unit represented by Formula (20) shall not specifically be restricted, and to be specific, it is carried out by using the syndiotactic styrenic polymers comprising the structural unit represented by Formula (12) described above and/or the syndiotactic styrenic block copolymer comprising the polymer segment (I) and the polymer segment (II) and reacting them at a temperature of −20 to 200° C. for one minute to 100 hours in the presence of a halogenating agent, a catalyst and a solvent.

If the reaction temperature is lower than −20° C., the reaction becomes uneven, which is attributed to the syndiotacticity of a high degree, and the reaction is reduced in efficiency. Accordingly, it is not preferred. On the other hand, if the reaction temperature exceeds 200° C., side reaction is increased, and therefore it is also not preferred. The reaction temperature is more preferably −10 to 100° C., most preferably 0 to 80° C.

Capable of being used as the halogenating agent are halogens such as fluorine, chlorine, bromine and iodine, compounds such as sodium hypochlorite, potassium hypochlorite, calcium hypochlorite, sodium hypobromite and sodium hypoiodite and compounds such as sulfuryl chloride, sulfuryl bromide and sulfuryl iodide.

Further, capable of being used as the catalyst are azobis compounds such as 2,2'-azobis(isobutyronitrile), 2,2'-azobis (isobutyric acid) dimethyl ester, 1,1'-azobis(cyclohexane-1-carbonitrile), 4,4'-azobis(4-cyanovaleric acid), 2,2'-azobis (2,4-dimethylvaleronitrile) and 2,2'-azobis(4-methoxy-2,4-dimethylvaleronitrile), peroxides such as benzoyl peroxide, isobutyryl peroxide, 3,5,5-trimethylhexanoyl peroxide, lauroyl peroxide, p-chlorobenzoyl peroxide, t-butyl hydroperoxide, cumene hydroperoxide and t-butyl-α-cumyl peroxide and compounds such as tetra-n-butylammonium chloride, tetra-n-butylammonium bromide, tetra-n-butylammonium iodide, tetra-n-butylammonium hydrogensulfite, benzyltriethylammonium chloride, tetraethylammonium chloride, tetraethylammonium bromide and tetraethylammonium iodide.

When used as the catalyst is a phase transfer catalyst such as tetra-n-butylammonium bromide, tetra-n-butylammonium hydrogensulfite and benzyltriethylammonium chloride, salts such as sodium chloride and sodium nitrate can be used as the co-catalyst.

On the other hand, capable of being used as the solvent are hydrocarbon solvents such as butane, pentane, hexane, heptane, octane, cyclohexane, mineral oil, benzene, toluene and xylene or halogenated hydrocarbon solvents such as chloroform, methylene chloride, dichloroethane and chlorobenzene. Further, water can be used, if necessary, in combination therewith.

In the syndiotactic styrenic block copolymer thus obtained having a halogenated methyl group, a part or the whole part of the structural unit having the halogenated methyl group can be converted into the unit represented by Formula (23). The copolymer thus converted is the syndiotactic styrenic block•graft copolymer, and a relation (Mw/Mn) between a number average molecular weight and a weight average molecular weight of a graft chain polymer in this block•graft copolymer is preferably 2 or less, particularly preferably 1.5 or less. If this value is larger than 2, characteristics required to the functional resin material are less liable to be revealed, and therefore it is not preferred.

Various monomers can be used as the monomer providing the structural unit represented by Formula (23) described above having a nitrogen-containing aromatic group as long as they are anionically polymerizable monomers providing living polymers which can be graft-copolymerized with the halogenated methyl group-modified syndiotactic styrenic polymer described above. Among them, monomers which are particularly suited in terms of easiness in availability and revelation of the functions such as an adhesive property include 2-vinylpyridine and 4-vinylpyridine.

A steric structure of the graft chain in the block•graft copolymer described above shall not specifically be restricted and may be an atactic structure, an isotactic structure, a syndiotactic structure or a mixed structure thereof. The steric structure of the graft chain is varied depending on the kind of the polymerization initiator and the polymerization conditions.

On the other hand, the syndiotactic styrenic block•graft copolymer of the present invention desirably has a molecular weight in a range of preferably 1,500 to 30,000,000, more preferably 3,000 to 10,000,000 and particularly preferably 10,000 to 5,000,000 in terms of a number average molecular weight. If the molecular weight is too small, the physical properties as the polymer become so unsatisfactory that the mechanical strength is low. On the other hand, if the molecular weight is too large, the problem that molding becomes difficult is caused. With respect to a molecular weight distribution of the syndiotactic styrenic block•graft copolymer of the present invention, the molecular weight distribution (Mw/Mn) which is a ratio of the weight average molecular weight (Mw) to the number average molecular weight (Mn) is in a range of preferably 20 or less, more preferably 15 or less, particularly preferably 10 or less and further preferably 3.0 or less. If the molecular weight distribution is too broad, the problem that the physical properties are reduced is caused, and therefore it is not preferred.

A content of a graft polymer in the block•graft copolymer of the present invention is not necessarily invariable depending on a molecular weight and a molecular number of a used prepolymer chain to be grafted having a living polymerization terminal, and it is usually 0.005 to 90% by weight, preferably 0.01 to 70% by weight.

The graft copolymer and/or the block•graft copolymer in the step 3 can be produced by living-polymerizing the nitrogen-containing aromatic monomer represented by Formula (25) described above in the presence of a suitable anionic initiator:

(25)

and then bringing it into contact with the halogenated methyl group-modified syndiotactic styrenic polymer and/or the halogenated methyl group-modified syndiotactic styrenic block copolymer described above obtained in the step 2.

The anionic initiator used above includes, for example, alkali metals (Cs, Rb, K, Na and Li), alkali metal alkyls (n-butyllithium, octylpotassim and benzylbarium), alkali metal aromatic compound complexes (Na-naphthalene) and alkali metal amides ($KNH_2$ and $LiN(C_2H5)_2$).

In the process of the present invention, graft copolymerization reaction is advanced in the graft polymerization step (step 3) by using the raw materials and the initiator described above and setting up the suitable conditions. With respect to the reaction conditions of the halogenated methyl group-modified syndiotactic styrenic polymer obtained in the step 2 with the anionically polymerized living graft prepolymer chain, capable of being suitably selected are the reaction temperature in a range of −100 to 200° C., preferably −80 to 120° C. and the reaction time in a range of one second to 10 hours.

A ratio of the structural unit represented by Formula (20) in the halogenated methyl group-modified syndiotactic styrenic polymer obtained in the step 2 to the anionically polymerized living graft prepolymer chain is usually latter/former=0.01 to 10 (mole ratio), preferably 0.05 to 5 and more preferably 0.1 to 2.

A polymerization method in the step 3 described above can be any method of bulk, solution and suspension polymerizations. In the solution polymerization, capable of being used as a solvent are aliphatic hydrocarbons such as pentane, hexane and heptane, alicyclic hydrocarbons such as cyclohexane, aromatic hydrocarbons such as benzene, toluene and xylene and solvents containing heteroatoms such as oxygen, nitrogen, sulfur and the like, such as tetrahydrofuran and 1,4-dioxane. The solvent used may be the same as or different from those used in the step 2 described above. It is conducted to remove the remaining unreacted monomers and the catalyst, and further a washing step is conducted in order to increase the graft efficiency.

EXAMPLES

Next, the present invention shall be explained in more details with reference to examples, but the present invention shall by no means be restricted by these examples.

First, the respective evaluation and measuring methods used in the examples in the present invention shall be described.

1) Catalyst Activity

Shown by an amount (g) of polymer per mmol of a catalyst metal per hour.

2) Molecular Weight and Molecular Weight Distribution of Polymer

Measured by means of a gel permeation chromatogaphy of model SSC-7100 manufactured by Senshu Science Co., Ltd. or model 8020 manufactured by Tosoh Corporation with an RI detector.

3) Syndiotacticity

Determined by measuring a pentad (racemic pentad) by $^{13}$C-NMR analysis by means of a nuclear magnetic resonance spectrometer of model JNM-LA600 manufactured by JEOL Ltd.

4) Melting Temperature

A melting temperature (Tm) determined by a peak top temperature at a crystal melting peak in c) according to a profile shown below and a glass transition temperature (Tg) were measured by DSC3200S manufactured by MacScience Co., Ltd in argon atmosphere.

a) heated from 0° C. up to 220° C. at 10° C./min
b) cooled from 220° C. down to 0° C. at 10° C./min
c) heated again from 0° C. up to 350° C. at 10° C./min 5) Block•Graft Copolymer Composition Determined by $^1$H-NMR by means of a nuclear magnetic resonance spectrometer of model JNM-LA600 manufactured by JEOL Ltd.

Example 1

A 100 ml glass-made three-neck flask which was dried and replaced therein with nitrogen was used to carry out polymerization reaction under nitrogen atmosphere. The 100 ml glass-made three-neck flask which was charged with 16.2 ml of toluene and 0.05 mmol of trioctylaluminum to carry out aging at room temperature for 10 minutes. The flask was then charged with 0.05 mmol of (trimethyl)pentamethylcyclopentadienyltitanium and subsequently 0.05 mmol of tris(pentafluorophenyl)boron and subjected to aging at room temperature for 10 minutes. Next, it was maintained at a constant temperature of −20° C. A toluene solution of 0.05 mmol of styrene was added thereto to carry out aging for 60 minutes.

Finally, 2.0 mmol of styrene and 2.0 mmol of p-methylstyrene were charged therein to carry out polymerization reaction at −20° C. for 90 minutes. A small amount of methanol was added to terminate the polymerization reaction, and the polymerization solution was poured into a large amount of acid methanol to deposit a polymer. The polymer thus obtained was washed, filtered, dried and weighed to obtain 0.173 g (yield: 38.5 wt %) of the polymer. The polymerization activity was 2.31 (g of polymer)/(mmol Ti)×hr).

The polymer thus obtained had a weight average molecular weight (Mw) of 372,000, a number average molecular weight (Mn) of 262,000 and a molecular weight distribution (Mw/Mn) of 1.42. Further, the syndiotacticity determined by $^{13}$C-NMR measurement was 95% or more in terms of a racemic pentad. The results thereof are shown in Table 1.

Example 2

A 100 ml glass-made three-neck flask which was dried and replaced therein with nitrogen was used to carry out polymerization reaction under nitrogen atmosphere. A Schlenk bottle having a content volume of 20 ml was charged with 4.3 ml of toluene, 5.0 mmol of methylaluminoxane and 0.05 mmol of styrene and maintained at a constant temperature of −20° C. A toluene solution of 0.05 mmol of indenyltrichlorotitanium (IndTiCl₃) was added thereto and subjected to aging for 60 minutes. on the other hand, a reactor (100 ml glass-made three-neck flask) was charged with 19.2 ml of toluene, 2 mmol of styrene, 2 mmol of p-methylstyrene and 16 mmol of methylaluminoxane and maintained at a constant temperature of −20° C. to carry out aging for 10 minutes.

Then, a solution in which indenyltrichlorotitanium (IndTiCl₃), methylaluminoxane and styrene were dissolved and which is subjected in advance to aging was added to the reactor to carry out polymerization reaction at −20° C. for 4 hours and 30 minutes. A small amount of methanol was added to terminate the polymerization reaction, and the polymerization solution was poured into a large amount of acid methanol to deposit a polymer. The polymer thus obtained was washed, filtered, dried and weighed to obtain 0.318 g (yield: 71.5 wt %) of the polymer. The polymerization activity was 1.41 (g of polymer)/(mmol Ti)×hr).

Measured were a weight average molecular weight (Mw), a number average molecular weight (Mn), a molecular weight distribution (Mw/Mn) and a syndiotacticity of the polymer thus obtained. The results thereof are shown in Table 1.

Example 3

A 200 ml glass-made three-neck flask which was dried and replaced therein with nitrogen was used to carry out polymerization reaction under nitrogen atmosphere. The 200 ml glass-made three-neck flask which was charged with 66.9 ml of toluene and 0.1 mmol of trioctylaluminum to carry out aging at room temperature for 10 minutes. The flask was then charged with 0.1 mmol of (trimethyl) pentamethylcyclopentadienyltitanium and subsequently 0.09 mmol of tris(pentafluorophenyl)boron to carry out aging at 15° C. for 10 minutes. Next, it was maintained at a constant temperature of −25° C. A toluene solution of 0.1 mmol of p-chlorostyrene was added thereto to carry out aging for 60 minutes.

Finally, 10.0 mmol of p-chlorostyrene was charged therein to carry out polymerization reaction at −25° C. for 2 hours. A small amount of methanol was added to terminate the polymerization reaction, and the polymerization solution was poured into a large amount of acid methanol to deposit a polymer. The polymer thus obtained was washed, filtered, dried and weighed to obtain 0.178 g (yield: 12.7 wt %) of the polymer. The polymerization activity was 0.888 (g of polymer)/(mmol Ti)×hr).

Measured were a weight average molecular weight (Mw), a number average molecular weight (Mn), a molecular weight distribution (Mw/Mn) and a syndiotacticity of the polymer thus obtained. The results thereof are shown in Table 1.

Example 4

A 200 ml three-neck flask which was dried and replaced therein with nitrogen was used to carry out polymerization reaction under nitrogen atmosphere. The 200 ml glass-made three-neck flask was charged with 67.6 ml of toluene and 0.1 mmol of trioctylaluminum to carry out aging at room temperature for 10 minutes. The flask was then charged with 0.1 mmol of (trimethyl) pentamethylcyclopentadienyltitanium and subsequently 0.09 mmol of tris(pentafluorophenyl)boron to carry out aging at 15° C. for 10 minutes. Next, it was maintained at a constant temperature of −25° C. A toluene solution of 0.1 mmol of p-chlorostyrene was added thereto to carry out aging for 60 minutes.

Finally, 2.0 mmol of p-chlorostyrene was charged therein to carry out polymerization reaction at −25° C. for 10 hours. A small amount of methanol was added to terminate the polymerization reaction, and the polymerization solution was poured into a large amount of acid methanol to deposit a polymer. The polymer thus obtained was washed, filtered, dried and weighed to obtain 0.133 g (yield: 45.7 wt %) of the polymer. The polymerization activity was 0.133 (g of polymer)/(mmol Ti)×hr).

Measured were a weight average molecular weight (Mw), a number average molecular weight (Mn), a molecular weight distribution (Mw/Mn) and a syndiotacticity of the polymer thus obtained. The results thereof are shown in Table 1.

Example 5

The same procedure as in Example 4 was carried out, except the polymerization condition was set to 14 hours at −25° C.

Measured were a weight average molecular weight (Mw), a number average molecular weight (Mn), a molecular weight distribution (Mw/Mn) and a syndiotacticity of the polymer thus obtained. The results thereof are shown in Table 1.

Example 6

A 200 ml glass-made three-neck flask was dried and replaced therein with nitrogen was used to carry out polymerization reaction under nitrogen atmosphere. The 200 ml glass-made three-neck flask which was charged with 65.5 ml of toluene and 0.2 mmol of trioctylaluminum to carry out aging at room temperature for 10 minutes. The flask was then charged with 0.2 mmol of (trimethyl) pentamethylcyclopentadienyltitanium and subsequently 0.18 mmol of tris(pentafluorophenyl)boron to carry out aging at 5° C. for 10 minutes. Next, it was maintained at a constant temperature of −25° C. A toluene solution of 0.1 mmol of p-chlorostyrene was added thereto to carry out aging for 60 minutes.

Finally, 2.0 mmol of p-chlorostyrene was charged therein to carry out polymerization reaction at −25° C. for 13.5 hours. A small amount of methanol was added to terminate the polymerization reaction, and the polymerization solution was poured into a large amount of acid methanol to deposit a polymer. The polymer thus obtained was washed, filtered, dried and weighed to obtain 0.268 g (yield: 92.1 wt %) of the polymer. The polymerization activity was 0.0993 (g of polymer)/(mmol Ti)×hr).

Measured were a weight average molecular weight (Mw), a number average molecular weight (Mn), a molecular weight distribution (Mw/Mn) and a syndiotacticity of the polymer thus obtained. The results thereof are shown in Table 1.

Example 7

A 200 ml glass-made three-neck flask which was dried and replaced therein with nitrogen was used to carry out polymerization reaction under nitrogen atmosphere. The 200 ml glass-made three-neck flask was charged with 65.5 ml of toluene and 0.2 mmol of trioctylaluminum to carry out aging at room temperature for 10 minutes. The flask was then charged with 0.1 mmol of (trimethyl)pentamethylcyclopentadienyltitanium and subsequently 0.1 mmol of tris(pentafluorophenyl)boron to carry out aging at 15° C. for 10 minutes.

Finally, 2.0 mmol of styrene was charged therein to carry out polymerization reaction at 15° C. for 5 minutes. A small amount of methanol was added to terminate the polymerization reaction, and the polymerization solution was poured into a large amount of acid methanol to deposit a polymer. The polymer thus obtained was washed, filtered, dried and weighed to obtain 0.194 g (yield: 93.1 wt %) of the polymer. The polymerization activity was 23.4 (g of polymer)/(mmol Ti)×hr).

Measured were a weight average molecular weight (Mw), a number average molecular weight (Mn), a molecular weight distribution (Mw/Mn) and a syndiotacticity of the polymer thus obtained. The results thereof are shown in Table 1.

Example 8

Synthesis of p-triisopropylsilyloxystyrene

A 300 ml glass-made three-neck flask was charged with 0.134 mol of p-vinylphenol, 0.343 mol of imidazole and 90 ml of dimethylformamide as a solvent, and a solution prepared by dissolving 0.174 mol of triisopropylsilyl chloride in 90 ml of dimethylformamide was dropwise added thereto at 0° C. in 50 minutes. Then, the reaction temperature was elevated up to room temperature to carry out reaction for 10 hours in the same condition. Water was added thereto, and the reaction product was extracted with chloroform. The solvent was distilled off, and the residue was dissolved in diethyl ether and washed with a sodium hydroxide aqueous solution and water. The product was dried on magnesium sulfate and filtered, and then it was further dried on a calcium hydride. Then, the reaction product was distilled at a reduced pressure under nitrogen flow to obtain aimed p-triisopropylsilyloxystyrene at a yield of 70%.

The structure of the product was confirmed by $^1$H-NMR, $^{13}$C-NMR, IR and elemental analysis. $^1$H-NMR ($C_2D_2Cl_4$) δ 7.22–6.75 (4H, dd, Ar), 6.61–6.56 (1H, dd, CH=), 5.56–5.05 (2H, dd, $CH_2$=), 1.20–1.15 (3H, m, SiCH), 1.03–1.01 (18H, t, $SiCH_3$) $^{13}$C-NMR ($C_2D_2Cl_4$) δ 156.2 ($ArC_4$), 136.6 (CH=), 130.7 ($ArC_1$), 127.7 ($ArC_2$ and C6), 120.3 ($ArC_3$ and C5), 112.0 ($CH_2$=), 18.3 ($CH_3$), 12.9 (SiCH) IR (KBr) 1266, 988, 913, 840, 790 $cm^{-1}$ Elemental analysis: calculated (C: 73.85; H: 10.21), analyzed (C: 73.96; H: 10.39)

Example 9

A 200 ml glass-made three-neck flask which was dried and replaced therein with nitrogen was used to carry out polymerization reaction under nitrogen atmosphere. The glass-made three-neck flask was charged with 68.1 ml of toluene and 0.2 mmol of trioctylaluminum to carry out aging at room temperature for 10 minutes. The flask was then charged with 0.1 mmol of (trimethyl)pentamethylcyclopentadienyltitanium and subsequently 0.09 mmol of tris(pentafluorophenyl)boron to carry out aging at room temperature for 10 minutes. Next, it was maintained at a constant temperature of –25° C. to carry out aging for 30 minutes.

Finally, 0.9 mmol of p-triisopropylsilyloxystyrene was charged therein to carry out polymerization reaction at –25° C. for 60 minutes. A small amount of methanol was added thereto to terminate the polymerization reaction, and the polymerization solution was poured into a large amount of methanol to deposit a polymer. The polymer thus obtained was dissolved again in toluene and filtered, and then the solution was poured again into a large amount of methanol to deposit the polymer. It was washed, filtered, dried and weighed to obtain 0.193 g (yield: 76.4 wt %) of the polymer. The polymerization activity was 1.93 (g of polymer)/(mmol Ti)×hr).

Measured were a weight average molecular weight (Mw), a number average molecular weight (Mn), a molecular weight distribution (Mw/Mn) and a syndiotacticity of the polymer thus obtained. Further, thermal analysis was carried out to find that observed were Tm in the vicinity of 251° C. and Tg in the vicinity of 116° C. The results thereof are shown in Table 2.

(Confirming that the Polymer Obtained in Example 9 has a Syndiotactic Structure)

Figure 2A:
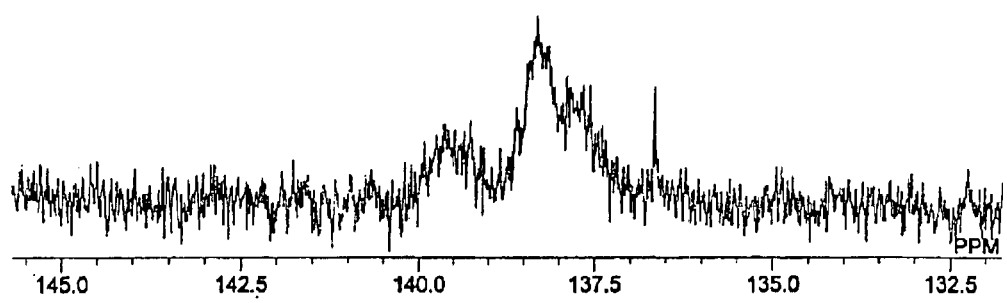
FIG. 2 is a $^{13}$C-NMR spectrum of an atactic polymer from the same monomer as in Example 9.

A $^{13}$C-NMR spectrum of the polymer obtained in Example 9 is shown in FIGS. 1(a) and (b), and a $^{13}$C-NMR spectrum of a polymer having an atactic structure is shown in FIGS. 2(a) and (b)

Figure 1B:
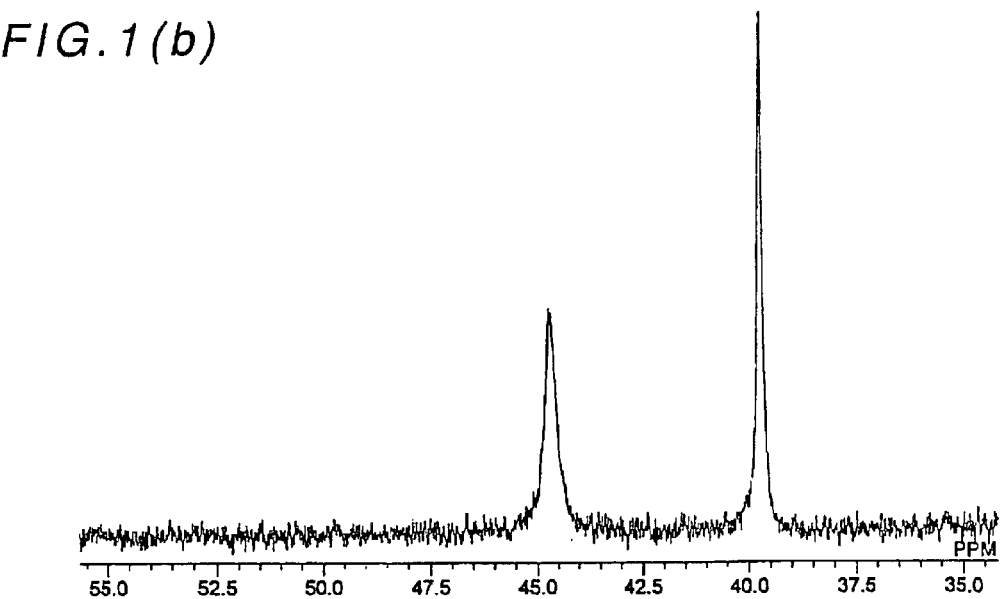
Figure 2B:
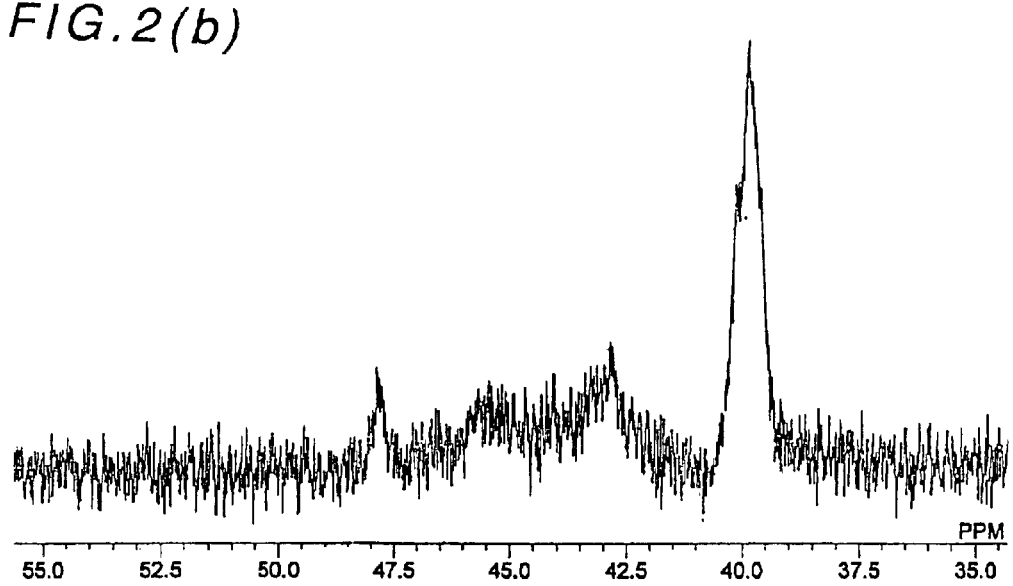

In FIG. 1(a), a peak of 137.87 ppm attributing to phenyl $^1$C carbon is sharpened very much as compared with that in FIG. 2(a) (atactic), and a peak of 44.72 ppm attributing to methine carbon in a main chain in FIG. 1(b) is sharpened very much as compared with that in FIG. 2(b). Accordingly, it can be found that the polymer obtained in Example 9 has a very high stereoregularity.

Also, the presence of an endothermic peak (melting point) observed by DSC measurement supports this fact. Further, as shown in Macromolecules, vol. 21, No. 12, p. 3356 (1988), in general, a peak of a racemic pentad structure derived from a syndiotactic structure is positioned on a high magnetic field side as compared with a complicated peak of an atactic structure. On the other hand, a peak of 137.87 ppm of phenyl $^1$C carbon in the polymer obtained in Example 9 shown in FIG. 1(a) is positioned on a high magnetic field side in a complicated peak of 137.0 to 141.0 ppm of phenyl $^1$C carbon having an atactic structure shown in FIG. 2(a). It can be found from these facts that the polymer obtained in Example 9 has a syndiotactic structure.

Example 10

A 200 ml glass-made three-neck flask which was dried and replaced therein with nitrogen was used to carry out polymerization reaction under nitrogen atmosphere. The glass-made three-neck flask was charged with 68.1 ml of toluene and 0.1 mmol of (trimethyl)pentamethylcyclopentadienyltitanium, and it was subsequently charged with 0.09 mmol of tris(pentafluorophenyl)boron to carry out aging at room temperature for 10 minutes. The flask was then charged with 0.2 mmol of trioctylaluminum to carry out aging at room temperature for 10 minutes. Next, it was maintained at a constant temperature of –25° C. to carry out aging for 30 minutes.

Finally, 0.9 mmol of p-triisopropylsilyloxystyrene was charged therein to carry out polymerization reaction at –25° C. for 15 minutes. A small amount of methanol was added thereto to terminate the polymerization reaction, and the polymerization solution was poured into a large amount of methanol to deposit a polymer. The polymer thus obtained was dissolved again in toluene and filtered, and then the solution was poured again into a large amount of methanol to deposit the polymer. It was washed, filtered, dried and weighed to obtain 0.041 g (yield: 16.2 wt %) of the polymer. The polymerization activity was 1.64 (g of polymer)/(mmol Ti)×hr).

Measured were a weight average molecular weight (Mw), a number average molecular weight (Mn), a molecular weight distribution (Mw/Mn) and a syndiotacticity of the polymer thus obtained. Further, thermal analysis was carried out to find that observed were Tm in the vicinity of 250° C. and Tg in the vicinity of 114° C. The results thereof are shown in Table 2.

Example 11

A 200 ml glass-made three-neck flask which was dried and replaced therein with nitrogen was used to carry out polymerization reaction under nitrogen atmosphere. The glass-made three-neck flask was charged with 69.0 ml of toluene and 0.1 mmol of (trimethyl)pentamethylcyclopentadienyltitanium, and it was subsequently charged with 0.09 mmol of tris(pentafluorophenyl)boron to carry out aging at room temperature for 10 minutes. The flask was then charged with 0.2 mmol of trioctylaluminum to carry out aging at room temperature for 10 minutes. Next, it was maintained at a constant temperature of −25° C. to carry out aging for 30 minutes.

Finally, 2.0 mmol of p-triisopropylsilyloxystyrene was charged therein to carry out polymerization reaction at −25° C. for 30 minutes. A small amount of methanol was added thereto to terminate the polymerization reaction, and the polymerization solution was poured into a large amount of methanol to deposit a polymer. The polymer thus obtained was dissolved again in toluene and filtered, and then the solution was poured again into a large amount of methanol to deposit the polymer. It was washed, filtered, dried and weighed to obtain 0.233 g (yield: 48.5 wt %) of the polymer. The polymerization activity was 4.66 (g of polymer)/(mmol Ti)×hr).

Measured were a weight average molecular weight (MW), a number average molecular weight (Mn), a molecular weight distribution (Mw/Mn) and a syndiotacticity of the polymer thus obtained. The results thereof are shown in Table 2.

Example 12

A 200 ml glass-made three-neck flask which was dried and replaced therein with nitrogen was used to carry out polymerization reaction under nitrogen atmosphere. The glass-made three-neck flask was charged with 69.0 ml of toluene and 0.1 mmol of (trimethyl)pentamethylcyclopentadienyltitanium, and it was subsequently charged with 0.09 mmol of tris(pentafluorophenyl)boron to carry out aging at room temperature for 10 minutes. The flask was then charged with 0.2 mmol of trioctylaluminum to carry out aging at room temperature for 10 minutes. Next, it was maintained at a constant temperature of −25° C. to carry out aging for 30 minutes.

Finally, 2.0 mmol of p-triisopropylsilyloxystyrene was charged therein to carry out polymerization reaction at −25° C. for 60 minutes. A small amount of methanol was added thereto to terminate the polymerization reaction, and the polymerization solution was poured into a large amount of methanol to deposit a polymer. The polymer thus obtained was dissolved again in toluene and filtered, and then the solution was poured again into a large amount of methanol to deposit the polymer. It was washed, filtered, dried and weighed to obtain 0.383 g (yield: 79.7 wt %) of the polymer. The polymerization activity was 3.83 (g of polymer)/(mmol Ti)×hr).

Measured were a weight average molecular weight (Mw), a number average molecular weight (Mn), a molecular weight distribution (Mw/Mn) and a syndiotacticity of the polymer thus obtained. The results thereof are shown in Table 2.

Example 13

A 200 ml glass-made three-neck flask which was dried and replaced therein with nitrogen was used to carry out polymerization reaction under nitrogen atmosphere. The glass-made three-neck flask was charged with 68.1 ml of toluene and 0.1 mmol of trioctylaluminum to carry out aging at room temperature for 10 minutes. The flask was then charged with 0.1 mmol of (trimethyl)pentamethylcyclopentadienyltitanium and subsequently 0.09 mmol of tris(pentafluorophenyl)boron to carry out aging at room temperature for 10 minutes. Next, it was maintained at a constant temperature of −25° C. to carry out aging for 10 minutes.

The flask was then charged with a toluene solution of 0.1 mmol of p-tert-butyldimethylsilyloxystyrene to further carry out aging at a temperature of −25° C. for 60 minutes.

Finally, a toluene solution of 2.0 mmol of p-tert-butyldimethylsilyloxystyrene was charged therein to carry out polymerization reaction at −25° C. for 5 minutes. A small amount of methanol was added thereto to terminate the polymerization reaction, and the polymerization solution was poured into a large amount of methanol to deposit a polymer. The polymer thus obtained was dissolved again in toluene and filtered, and then the solution was poured again into a large amount of methanol to deposit the polymer. It was washed, filtered, dried and weighed to obtain 0.119 g (yield: 24.2 wt %) of the polymer. The polymerization activity was 14.3 (g of polymer)/(mmol Ti)×hr).

Measured were a weight average molecular weight (Mw), a number average molecular weight (Mn), a molecular weight distribution (Mw/Mn) and a syndiotacticity of the polymer thus obtained. Further, thermal analysis was carried out to find that Tg was observed at 104° C. The results thereof are shown in Table 2.

Example 14

A 200 ml glass-made three-neck flask which was dried and replaced therein with nitrogen was used to carry out polymerization reaction under nitrogen atmosphere. The glass-made three-neck flask was charged with 68.1 ml of toluene and 0.1 mmol of trioctylaluminum to carry out aging at room temperature for 10 minutes. The flask was then charged with 0.1 mmol of (trimethyl)pentamethylcyclopentadienyltitanium and subsequently 0.09 mmol of tris(pentafluorophenyl)boron to carry out aging at room temperature for 10 minutes. Next, it was maintained at a constant temperature of −25° C. to carry out aging for 10 minutes.

The flask was then charged with a toluene solution of 0.1 mmol of p-tert-butyldimethylsilyloxystyrene to further carry out aging at a temperature of −25° C. for 60 minutes.

Finally, a toluene solution of 2.0 mmol of p-tert-butyldimethylsilyloxystyrene was charged therein to carry out polymerization reaction at −25° C. for 10 minutes. A small amount of methanol was added thereto to terminate the polymerization reaction, and the polymerization solution was poured into a large amount of methanol to deposit a polymer. The polymer thus obtained was dissolved again in toluene and filtered, and then the solution was poured again into a large amount of methanol to deposit the polymer. It was washed, filtered, dried and weighed to obtain 0.227 g (yield: 46.2 wt %) of the polymer. The polymerization activity was 13.6 (g of polymer)/(mmol Ti)×hr).

Measured were a weight average molecular weight (Mw), a number average molecular weight (Mn), a molecular weight distribution (Mw/Mn) and a syndiotacticity of the polymer thus obtained. Further, thermal analysis was carried out to find that Tg was observed at 105° C. The results thereof are shown in Table 2.

Example 15

A 200 ml glass-made three-neck flask which was dried and replaced therein with nitrogen was used to carry out polymerization reaction under nitrogen atmosphere. The glass-made three-neck flask was charged with 68.1 ml of toluene and 0.1 mmol of trioctylaluminum to carry out aging at room temperature for 10 minutes. The flask was then charged with 0.1 mmol of (trimethyl)pentamethylcyclopentadienyltitanium and subsequently 0.09 mmol of tris(pentafluorophenyl)boron to carry out aging at room temperature for 10 minutes. Next, it was maintained at a constant temperature of −25° C. to carry out aging for 10 minutes.

The flask was then charged with a toluene solution of 0.1 mmol of p-tert-butyldimethylsilyloxystyrene to further carry out aging at a temperature of −25° C. for 60 minutes.

Finally, a toluene solution of 2.0 mmol of p-tert-butyldimethylsilyloxystyrene was charged therein to carry out polymerization reaction at −25° C. for 20 minutes. A small amount of methanol was added thereto to terminate the polymerization reaction, and the polymerization solution was poured into a large amount of methanol to deposit a polymer. The polymer thus obtained was dissolved again in toluene and filtered, and then the solution was poured again into a large amount of methanol to deposit the polymer. It was washed, filtered, dried and weighed to obtain 0.364 9 (yield: 73.9 wt %) of the polymer. The polymerization activity was 10.9 (g of polymer)/(mmol Ti)×hr).

Measured were a weight average molecular weight (MW), a number average molecular weight (Mn), a molecular weight distribution (Mw/Mn) and a syndiotacticity of the polymer thus obtained. Further, thermal analysis was carried out to find that Tg was observed at 105° C. The results thereof are shown in Table 2.

(Confirming that the Polymer Obtained in Example 15 has a Syndiotactic Structure)

Figure 3A:
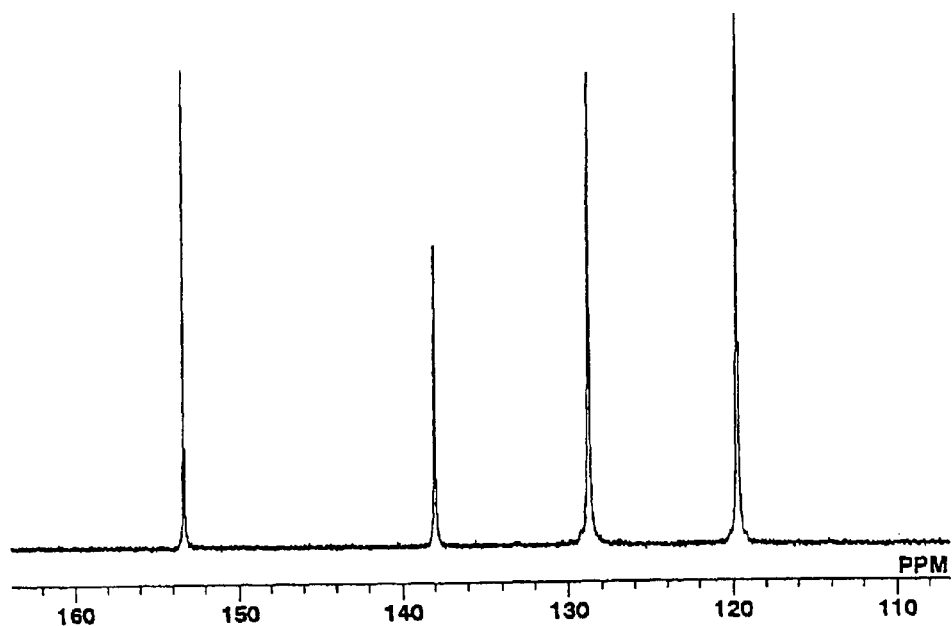
FIG. 3 is a $^{13}$C-NMR spectrum of a polymer obtained in Example 15.
Figure 4A:
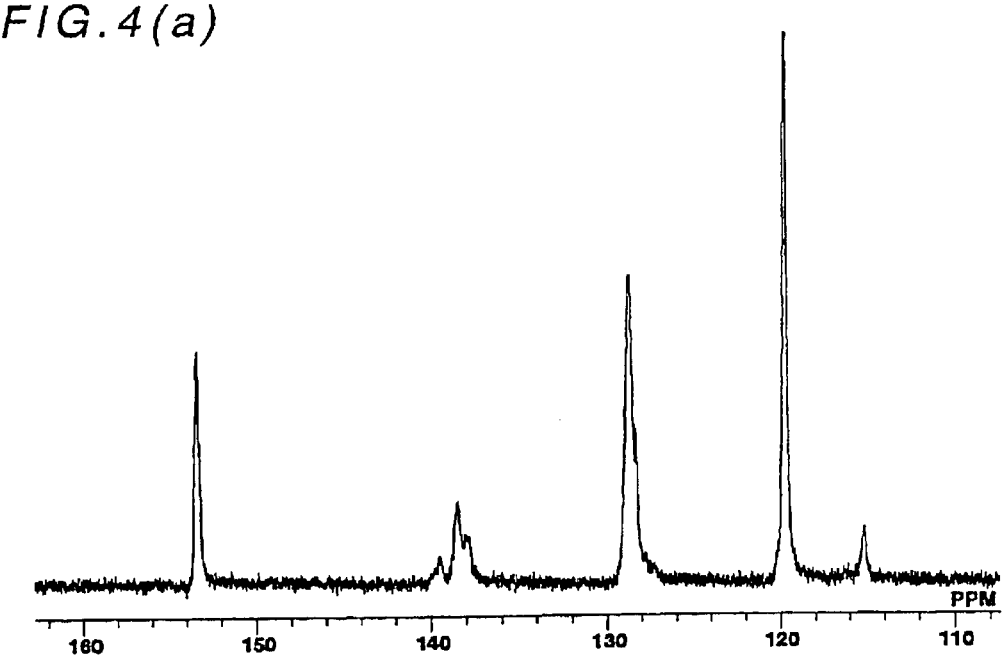
FIG. 4 is a $^{13}$C-NMR spectrum of an atactic polymer obtained from the same monomer as in Example 15 by thermal polymerization.

A $^{13}$C-NMR spectrum of the polymer obtained in Example 15 is shown in FIGS. 3(a) and (b), and a $^{13}$C-NMR spectrum of a polymer having an atactic structure is shown in FIGS. 4(a) and (b)

Figure 3B:
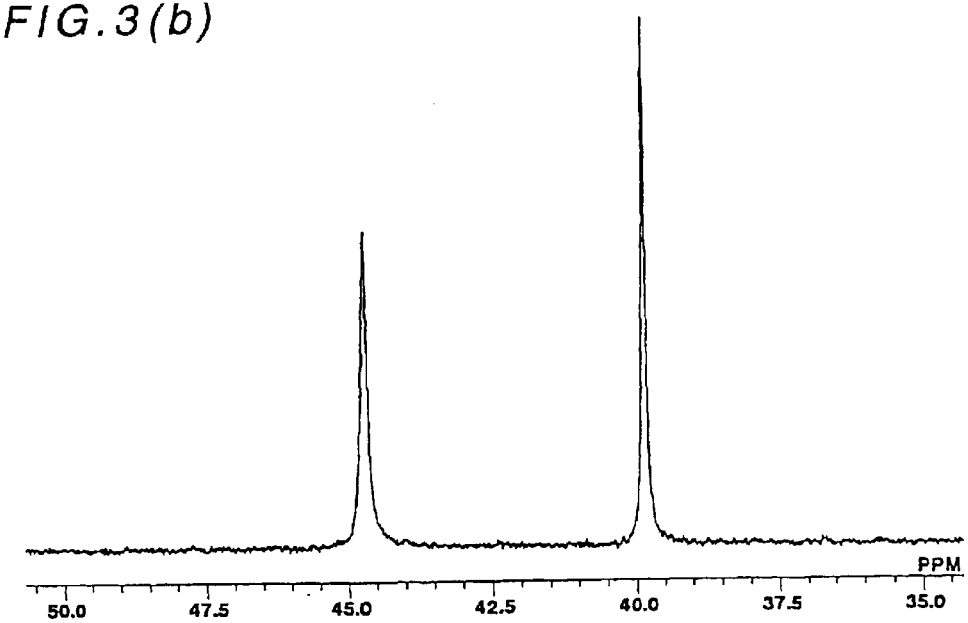
Figure 4B:
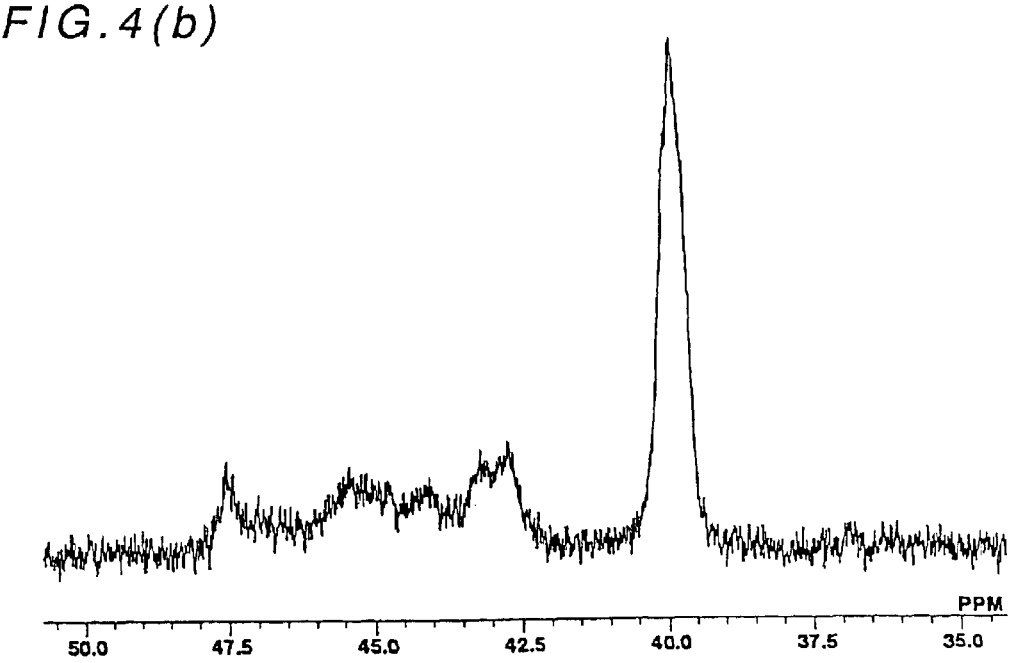

In FIG. 3(a), a peak of 138.01 ppm attributing to phenyl $^1$C carbon is sharpened very much as compared with that in FIG. 4(a) (atactic), and a peak of 44.73 ppm attributing to methine carbon in a main chain in FIG. 3(b) is sharpened very much as compared with that in FIG. 4(b). Accordingly, it can be found that the polymer obtained in Example 15 has a very high stereoregularity.

Further, as shown in Macromolecules, vol. 21, No. 12, p. 3356 (1988), in general, a peak of a racemic pentad structure derived from a syndiotactic structure is positioned on a high magnetic field side as compared with a complicated peak of an atactic structure. On the other hand, a peak of 138.01 ppm of phenyl $^1$C carbon in the polymer obtained in Example 15 shown in FIG. 3(a) is positioned on a high magnetic field side in a complicated peak of 137.0 to 140.5 ppm of phenyl $^1$C carbon having an atactic structure shown in FIG. 4(a). It can be found from these facts that the polymer obtained in Example 15 has a syndiotactic structure.

Example 16

A 200 ml glass-made three-neck flask which was dried and replaced therein with nitrogen was used to carry out polymerization reaction under nitrogen atmosphere. The glass-made three-neck flask was charged with 68.1 ml of toluene and 0.1 mmol of trioctylaluminum to carry out aging at room temperature for 10 minutes. The flask was then charged with 0.1 mmol of (trimethyl)pentamethylcyclopentadienyltitanium and subsequently 0.09 mmol of tris(pentafluorophenyl)boron to carry out aging at room temperature for 10 minutes. Next, it was maintained at a constant temperature of −25° C. to carry out aging for 10 minutes.

The flask was then charged with a toluene solution of 0.1 mmol of p-tert-butyldimethylsilyloxystyrene to further carry out aging at a temperature of −25° C. for 60 minutes.

Finally, a toluene solution of 2.0 mmol of p-tert-butyldimethylsilyloxystyrene was charged therein to carry out polymerization reaction at −25° C. for 30 minutes. A small amount of methanol was added thereto to terminate the polymerization reaction, and the polymerization solution was poured into a large amount of methanol to deposit a polymer. The polymer thus obtained was dissolved again in toluene and filtered, and then the solution was poured again into a large amount of methanol to deposit the polymer. It was washed, filtered, dried and weighed to obtain 0.444 g (yield: 90.2 wt %) of the polymer. The polymerization activity was 8.88 (g of polymer)/(mmol Ti)×hr).

Measured were a weight average molecular weight (MW), a number average molecular weight (Mn), a molecular weight distribution (Mw/Mn) and a syndiotacticity of the polymer thus obtained. Further, thermal analysis was carried out to find that Tg was observed at 105° C. The results thereof are shown in Table 2.

Example 17

A 30 ml Schlenk bottle which was dried and replaced therein with nitrogen was used to carry out reaction under nitrogen atmosphere. The glass-made Schlenk bottle was charged with 0.049 g of poly(p-triisopropylsilyloxystyrene) obtained in Example 9 and subsequently charged with 5.0 mmol of tetrabutylammonium fluoride and 25 ml of tetrahydrofuran, and the mixture was stirred at room temperature for 120 minutes. Next, it was maintained at a constant temperature of 60° C. and stirred for 120 minutes. The polymer solution described above was poured into a large amount of a saturated ammonium chloride aqueous solution to deposit a polymer. The polymer thus obtained was washed well with water and dissolved again in ethanol, and it was poured into hexane to deposit the polymer. It was washed, filtered, dried and weighed to obtain 0.010 g (yield: 19.5 wt %) of the polymer.

Measured were a weight average molecular weight (Mw), a number average molecular weight (Mn), a molecular weight distribution (Mw/Mn) and a syndiotacticity of the polymer thus obtained. The results thereof are shown in Table 2.

(Confirming that the Polymer Obtained in Example 17 has a Syndiotactic Structure)

Figure 5A:
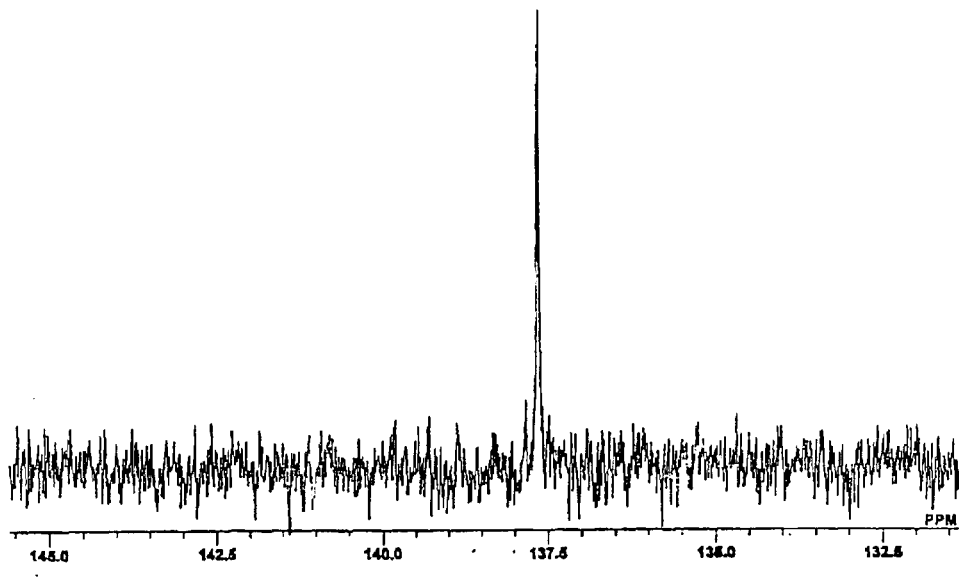
FIG. 5 is a $^{13}$C-NMR spectrum of a polymer obtained in Example 17.
Figure 6A:
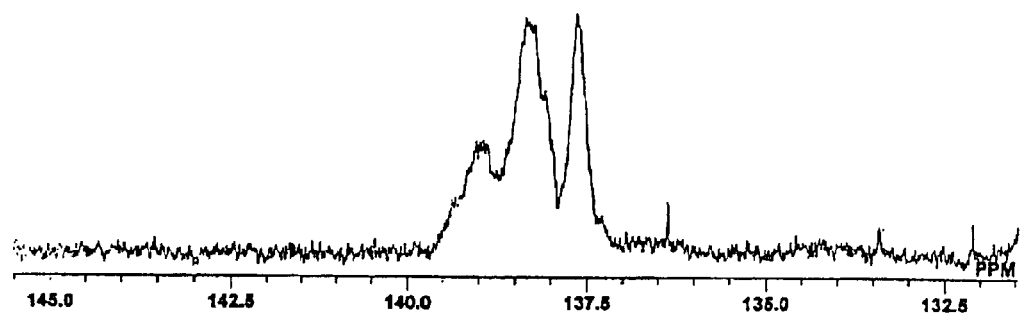
FIG. 6 is a $^{13}$C-NMR spectrum of the atactic hydroxystyrenic polymers produced from the same monomer as in Example 17.

A $^{13}$C-NMR spectrum of the polymer obtained in Example 17 is shown in FIGS. 5(a) and (b), and a $^{13}$C-NMR spectrum of a polymer having an atactic structure is shown in FIGS. 6(a) and (b).

Figure 5B:
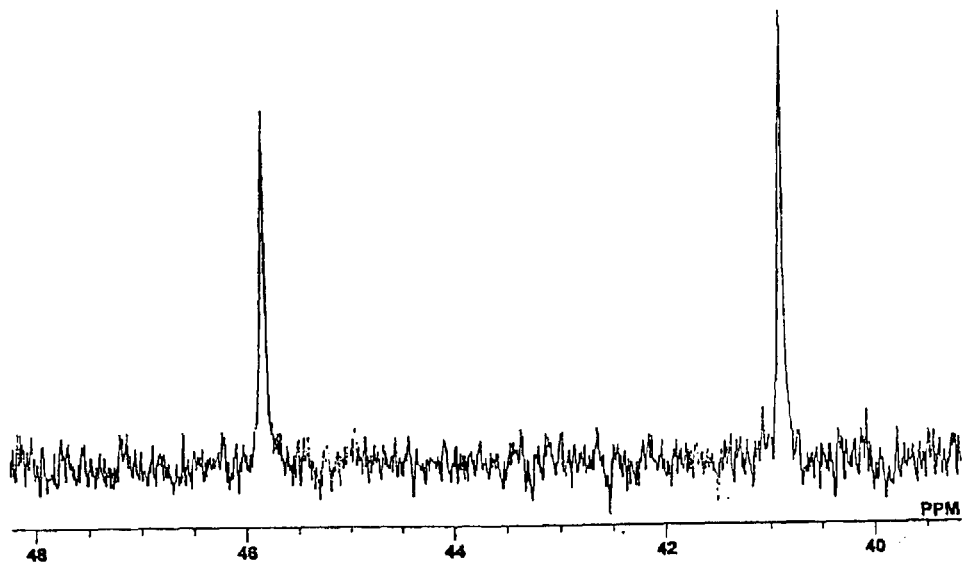
Figure 6B:
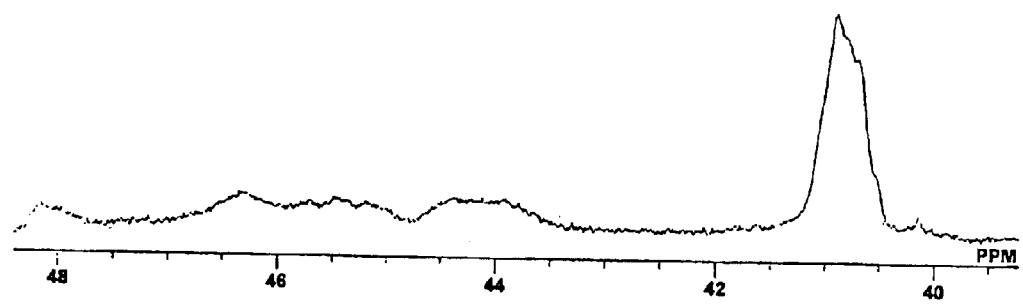

In FIG. 5(a), a peak of 137.66 ppm attributing to phenyl $^1$C carbon is sharpened very much as compared with that in FIG. 6(a) (atactic), and a peak of 45.84 ppm attributing to methine carbon in a main chain in FIG. 5(b) is sharpened very much as compared with that in FIG. 6(b). Accordingly, it can be found that the polymer obtained in Example 17 has a very high stereoregularity.

Further, as shown in Macromolecules, vol. 21, No. 12, p. 3356 (1988), in general, a peak of a racemic pentad structure derived from a syndiotactic structure is positioned on a high magnetic field side as compared with a complicated peak of an atactic structure. On the other hand, a peak of 137.66 ppm of phenyl $^1$C carbon in the polymer obtained in Example 17 shown in FIG. 5(a) is positioned on a high magnetic field side in a complicated peak of 137.2 to 139.7 ppm of phenyl $^1$C carbon having an atactic structure shown in FIG. 6(a). It can be found from these facts that the polymer obtained in Example 17 has a syndiotactic structure.

Example 18

A 30 ml glass-made Schlenk bottle which was dried and replaced therein with nitrogen was used to carry out reaction under nitrogen atmosphere. The glass-made Schlenk bottle was charged with 0.077 g of poly(p-triisopropylsilyloxystyrene) obtained in Example 12 and subsequently charged with 7.0 ml of a 10% potassium hydroxide methanol solution and 20 ml of tetrahydrofuran, and the mixture was stirred at 60° C. for 120 minutes. The polymer solution described above was poured into a large amount of a hydrochloric acid aqueous solution to deposit a polymer. The polymer thus obtained was washed well with water and dissolved again in methanol, and it was poured again into a hydrochloric acid aqueous solution to deposit the polymer. It was washed, filtered, dried and weighed to obtain 0.031 g (yield: 40.6 wt %) of the polymer.

Measured were a weight average molecular weight (Mw), a number average molecular weight (Mn), a molecular weight distribution (Mw/Mn) and a syndiotacticity of the polymer thus obtained. The results thereof are shown in Table 2.

Example 19

A 50 ml glass-made three neck flask which was dried and replaced therein with nitrogen was used to carry out reaction under nitrogen atmosphere. A glass-made three-neck flask was charged with 0.201 g of poly(p-tert-butyldimethylsilyloxystyrene) obtained in Example 15 and subsequently charged with 30 ml of tetrahydrofuran to dissolve the polymer. Then, it was charged with 6.0 ml of 37% hydrochloric acid and stirred at a temperature at which tetrahydrofuran was refluxed for 240 minutes while heating. After stopping heating, the polymer solution described above was poured into water to deposit a polymer. The polymer thus obtained was washed well with water and dissolved again in ethanol, and it was poured into hexane to deposit the polymer, which was repeated twice. It was washed, filtered, dried and weighed to obtain 0.086 g (yield: 83.9 wt %) of the polymer.

Measured were a weight average molecular weight (Mw), a number average molecular weight (Mn), a molecular weight distribution (Mw/Mn) and a syndiotacticity of the polymer thus obtained. Further, thermal analysis was carried out to find that Tg was observed at 194° C. The results thereof are shown in Table 2.
(Confirming that the Polymer Obtained in Example 19 has a Syndiotactic Structure)

A $^{13}$C-NMR spectrum of the polymer obtained in Example 19 is shown in FIG. 7, and a $^{13}$C-NMR spectrum of a polymer having an atactic structure is shown in FIG. 6.

Figure 7A:
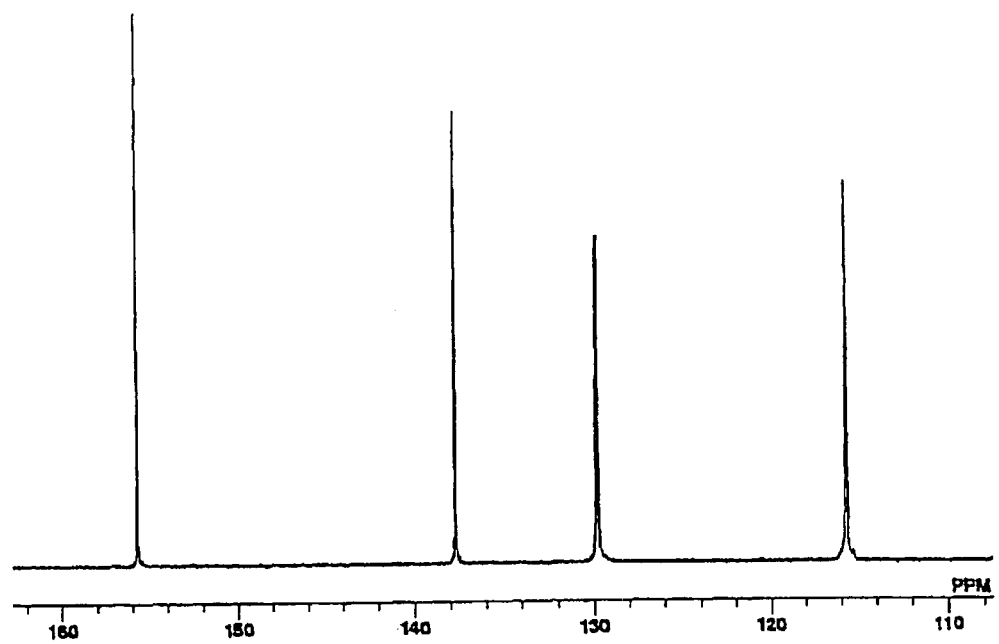
FIG. 7 is a $^{13}$C-NMR spectrum of a polymer obtained in Example 19.
Figure 7B:
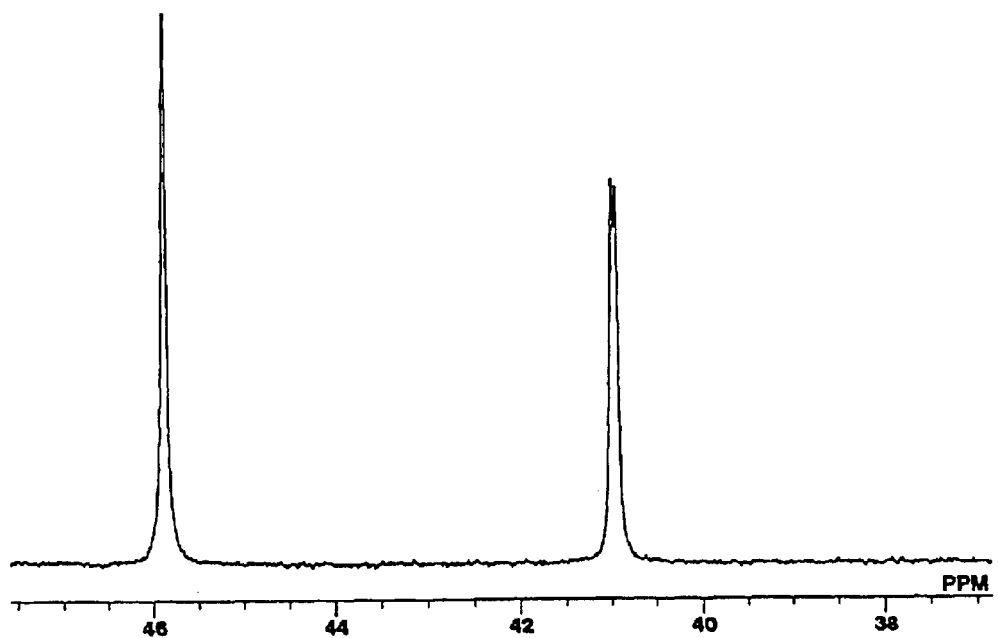

In FIG. 7(a), a peak of 137.76 ppm attributing to phenyl $^1$C carbon is sharpened very much as compared with that in FIG. 6(a) (atactic), and a peak of 45.88 ppm attributing to methine carbon in a main chain in FIG. 7(b) is sharpened very much as compared with that in FIG. 6(b). Accordingly, it can be found that the polymer obtained in Example 19 has a very high stereoregularity.

Further, as shown in Macromolecules, vol. 21, No. 12, p. 3356 (1988), in general, a peak of a racemic pentad structure derived from a syndiotactic structure is positioned on a high magnetic field side as compared with a complicated peak of an atactic structure. On the other hand, a peak of 137.76 ppm of phenyl $^1$C carbon in the polymer obtained in Example 19 shown in FIG. 7(a) is positioned on a high magnetic field side in a complicated peak of 137.2 to 139.7 ppm of phenyl $^1$C carbon having an atactic structure shown in FIG. 6(a). It can be found from these facts that the polymer obtained in Example 19 has a syndiotactic structure.

Reference Example 1

Production of p-methylstyrene homopolymer

A 200 ml glass-made three-neck flask which was dried and replaced therein with nitrogen was used to carry out polymerization reaction under nitrogen atmosphere. The three-neck flask was charged with 68 ml of toluene and 0.1 mmol of trioctylaluminum to carry out aging at room temperature for 10 minutes. The flask was then charged with 0.1 mmol of (trimethyl)pentamethylcyclopentadienyltitanium and subsequently 0.09 mmol of tris(pentafluorophenyl)boron to carry out aging at room temperature for 10 minutes. Next, it was maintained at a constant temperature of −25° C. to carry out aging for 10 minutes. Then, the flask was charged with a toluene solution of 0.1 mmol of p-methylstyrene to further carry out aging for 60 minutes.

Then, after the flask was charged with 20 ml of a toluene solution of 2.0 mmol of p-methylstyrene to carry out polymerization reaction at −25° C. for 25 minutes, a small amount of methanol was added thereto to terminate the reaction, and the polymerization solution was poured into a large amount of a hydrochloric acid methanol solution to deposit a polymer. The polymer thus obtained was washed, filtered and dried, and then it was further dissolved in toluene and filtered. Then, the polymer was deposited again in a large amount of methanol, and the resulting polymer was washed, filtered, dried and then weighed to obtain 0.249 g (monomer conversion rate: 99%) of the polymer.

Measured were a weight average molecular weight (Mw), a number average molecular weight (Mn), a molecular weight distribution (Mw/Mn) and a syndiotacticity of the polymer thus obtained. The results thereof are shown in Table 2.

TABLE 1

Examples 1 to 7

| | Example | | | | | | |
|---|---|---|---|---|---|---|---|
| | 1 | 2 | 3 | 4 | 5 | 6 | 7 |
| Weight average molecular weight (Mw) | 372000 | 541000 | 35900 | 25100 | 30100 | 21300 | 23300 |
| Number average molecular weight (Mn) | 262000 | 369000 | 31500 | 20600 | 25100 | 15800 | 15000 |
| Molecular weight distribution (Mw/Mn) | 1.42 | 1.47 | 1.14 | 1.22 | 1.20 | 1.35 | 1.30 |
| Syndiotacticity (%) | 95 or more | 95 or more | 95 or more | 95 or more | 95 or more | 95 or more | 95 or more |

TABLE 2

Examples 9 to 19 & Reference Example 1

| | Example | | | | | | | | | | | Reference |
|---|---|---|---|---|---|---|---|---|---|---|---|---|
| | 9 | 10 | 11 | 12 | 13 | 14 | 15 | 16 | 17 | 18 | 19 | Example 1 |
| Weight average molecular weight (Mw) | 45600 | 18500 | 69000 | 102000 | 31600 | 46800 | 65500 | 89900 | 23300 | 102000 | 54300 | 61100 |
| Number average molecular weight (Mn) | 36300 | 13400 | 55200 | 81700 | 29300 | 44000 | 60800 | 82400 | 19900 | 39800 | 49900 | 52000 |
| Molecular weight distribution (Mw/Mn) | 1.26 | 1.38 | 1.25 | 1.25 | 1.08 | 1.06 | 1.08 | 1.09 | 1.17 | 2.56 | 1.09 | 1.18 |
| Syndiotacticity (%) | 95 or more | 95 or more | 95 or more | 95 or more | 95 or more | 95 or more | 95 or more | 95 or more | 95 or more | 90 or more | 95 or more | 90 or more |
| Crystal melting temperature Tm (° C.) | 251 | 250 | — | — | — | — | — | — | — | — | — | — |
| Glass transition temperature Tg (° C.) | 116 | 114 | — | — | 104 | 105 | 105 | 105 | — | — | 194 | — |

*—: not measured

Example 20

Production of (p-methylstyrene)-b-(styrene-co-(m-methylstyrene)) Block Copolymer A 200 ml glass-made three-neck flask which was dried and replaced therein with nitrogen was used to carry out polymerization reaction under nitrogen atmosphere. The three-neck flask was charged with 68 ml of toluene and 0.1 mmol of trioctylaluminum to carry out aging at room temperature for 10 minutes. The flask was then charged with 0.1 mmol of (trimethyl)pentamethylcyclopentadienyltitanium and subsequently 0.09 mmol of tris(pentafluorophenyl)boron to carry out aging at room temperature for 10 minutes. Next, it was maintained at a constant temperature of −25° C. to carry out aging for 10 minutes. Then, the flask was charged with a toluene solution of 0.1 mmol of p-methylstyrene to further carry out aging for 60 minutes.

Then, the flask was charged with 20 ml of a toluene solution of 2.0 mmol of p-methylstyrene to carry out polymerization reaction at −25° C. for 25 minutes. Then, after a toluene solution of 19.0 mmol of styrene and 1.0 mmol of m-methylstyrene was added thereto to carry out the polymerization reaction at the same temperature for 30 minutes, a small amount of methanol was added thereto to terminate the reaction, and the polymerization solution was poured into a large amount of a hydrochloric acid methanol solution to deposit a polymer. The polymer thus obtained was washed, filtered and dried, and then it was further dissolved in toluene and filtered. Then, the polymer was deposited again in a large amount of methanol, and the resulting polymer was washed, filtered, dried and then weighed to obtain 0.663 g of the polymer.

The polymer thus obtained had a weight average molecular weight (Mw) of 121000, a number average molecular weight (Mn) of 87100 and a molecular weight distribution (Mw/Mn) of 1.39. Further, an average molecular weight and a molecular weight distribution of the p-methylstyrene polymer segment (I) contained in the present block copolymer were obtained from the results of Reference Example 1 and were a weight average molecular weight (Mw) of 61100, a number average molecular weight (Mn) of 52000 and a molecular weight distribution (Mw/Mn) of 1.18. Also, the syndiotacticity determined by $^{13}$C-NMR measurement was 90% or more in terms of a racemic pentad. Further, the block copolymer had a composition of 64.2 mole % of styrene, 27.0 mole % of p-methylstyrene and 8.8 mole % of m-methylstyrene which were determined by $^{13}$C-NMR.

Example 21

Production of chloromethyl-modified (p-methylstyrene)-b-(styrene-co-(m-methylstyrene)) Block Copolymer A 100 ml glass-made Schlenk bottle which was dried and replaced therein with nitrogen was used to carry out reaction under nitrogen atmosphere. The Schlenk flask was charged with 0.204 g of the (p-methylstyrene)-b-(styrene-co-(m-methylstyrene)) block copolymer obtained in Example 20 and 10.0 ml of chloroform and then charged with 13.6 ml of a 5% sodium hypochlorite aqueous solution (pH was adjusted to 8.4 by conc. hydrochloric acid). Subsequently, an aqueous solution of 0.04 mmol of benzyltriethylammonium chloride was added thereto to carry out reaction at 25° C. for 2 hours.

Then, the reaction solution was poured into a large amount of methanol to deposit a polymer. The polymer thus obtained was washed, filtered, dried and then weighed to obtain 0.204 g of the polymer. Converted into chloromethyl groups was 5.0 mole % of the methyl groups in p-methylstyrene and m-methylstyrene of the block copolymer, which was determined by $^{13}$C-NMR measurement. No change was observed in the steric structure of the resulting chloromethyl-modified (p-methylstyrene)-b-(styrene-co-(m-methylstyrene)) block copolymer as compared with that of the (p-methylstyrene)-b-(styrene-co-(m-methylstyrene)) block copolymer obtained in Example 20, which was the raw material.

Example 22

Production of (p-methylstyrene)-b-(styrene-co-(m-methylstyrene))-g-(2-vinylpyridine)) Block•Graft Copolymer A 100 ml glass-made Schlenk bottle which was dried and replaced therein with nitrogen was used to carry out polymerization reaction under nitrogen atmosphere. The glass-made Schlenk bottle was charged with 20.0 ml of tetrahydrofuran (THF) and a cyclohexane/n-hexane solution of 0.2 mmol of sec-BuLi at –78° C. to carry out aging for 10 minutes. Then, 0.5 ml of 2-vinylpyridine was slowly added thereto to start polymerization reaction. The polymerization reaction was carried out at the same temperature for 120 minutes.

Sampled was 9.3 ml of this polymerization reaction solution, and it was charged into another glass-made Schlenk bottle at 25° C. Then, a THF solution of 0.062 g of the chloromethyl-modified (p-methylstyrene)-b-(styrene-co-(m-methylstyrene)) block copolymer obtained in Example 21 was added thereto to carry out grafting reaction. A small amount of methanol was added thereto to terminate the reaction, and the polymer solution was poured into a large amount of hexane to deposit a polymer.

The polymer thus obtained was washed, filtered, dried and weighed to obtain 0.299 g of the polymer. The resulting polymer was measured for a molecular weight by GPC to observe a peak derived from the block•graft copolymer having a weight average molecular weight (Mw) of 849000, a number average molecular weight (Mn) of 129000 and a molecular weight distribution (Mw/Mn) of 6.57 on a high molecular weight side of the raw material block copolymer.

Further, molecular weight analysis of the peak of unreacted poly(2-vinylpyridine) showed that the grafted polymer had a weight average molecular weight (Mw) of 2310, a number average molecular weight (Mn) of 2050 and a molecular weight distribution (Mw/Mn) of 1.13.

Reference Example 2

Production of p-methylstyrene homopolymer

A 200 ml glass-made three-neck flask which was dried and replaced therein with nitrogen was used to carry out polymerization reaction under nitrogen atmosphere. The three-neck flask was charged with 72 ml of toluene and 0.1 mmol of trioctylaluminum to carry out aging at room temperature for 10 minutes. The flask was then charged with 0.1 mmol of (trimethyl)pentamethylcyclopentadienyltitanium and subsequently 0.09 mmol of tris(pentafluorophenyl)boron to carry out aging at room temperature for 10 minutes. Next, it was maintained at a constant temperature of –25° C. to carry out aging for 10 minutes. Then, the flask was charged with a toluene solution of 0.1 mmol of p-methylstyrene to further carry out aging for 60 minutes.

Then, after the flask was charged with 20 ml of a toluene solution of 2.0 mmol of p-methylstyrene to carry out polymerization reaction at –25° C. for 20 minutes, a small amount of methanol was added thereto to terminate the reaction, and the polymerization solution was poured into a large amount of a hydrochloric acid methanol solution to deposit a polymer. The polymer thus obtained was washed, filtered and dried, and then it was further dissolved in toluene and filtered. Then, the polymer was deposited again in a large amount of methanol, and the resulting polymer was washed, filtered, dried and then weighed to obtain 0.212 g (monomer conversion rate: 85%) of the polymer.

The polymer thus obtained had a weight average molecular weight (Mw) of 65700, a number average molecular weight (Mn) of 57000 and a molecular weight distribution (Mw/Mn) of 1.15. Further, the syndiotacticity determined by $^{13}$C-NMR measurement was 90% or more in terms of a racemic pentad.

Example 23

Production of chloromethyl-modified p-methylstyrene polymer

A 100 ml glass-made Schlenk flask which was dried and replaced therein with nitrogen was used to carry out reaction under nitrogen atmosphere. The Schlenk flask was charged with 0.102 g of the p-methylstyrene homopolymer obtained in Reference Example 2 and 10.0 ml of benzene and then charged with a benzene solution of 0.0061 mmol of 2,2'-azobis(isobutyronitrile) and 0.62 mmol of sulfuryl chloride. Subsequently, the flask was heated to carry out reaction at 50° C. for 40 minutes.

Then, the reaction solution was poured into a large amount of methanol to deposit a polymer. The polymer thus obtained was washed, filtered, dried and then weighed to obtain 0.110 g of the polymer. Converted into chloromethyl groups was 8.1 mole % of the methyl groups in p-methylstyrene of the p-methylstyrene polymer, which was determined by $^{13}$C-NMR measurement. No change was observed in the steric structure of the resulting chloromethyl-modified p-methylstyrene polymer as compared with that of the p-methylstyrene polymer obtained in Reference Example 2, which was the raw material.

Example 24

Production of (p-methylstyrene)-g-(2-vinylpyridine) graft copolymer

A 100 ml glass-made Schlenk bottle which was dried and replaced therein with nitrogen was used to carry out polymerization reaction under nitrogen atmosphere. The glass-made Schlenk bottle was charged with 20.0 ml of tetrahydrofuran (THF) and a cyclohexane/n-hexane solution of 0.1 mmol of sec-BuLi at –78° C. to carry out aging for 10 minutes. Then, 0.25 ml of 2-vinylpyridine was slowly added thereto to start polymerization reaction. The polymerization reaction was carried out at the same temperature for 120 minutes.

Sampled was 12.0 ml of this polymerization reaction solution, and it was charged into another glass-made Schlenk bottle at 25° C. Then, a THF solution of 0.060 g of the chloromethyl-modified p-methylstyrene polymer obtained in Example 23 was added thereto to carry out grafting reaction. A small amount of methanol was added thereto to terminate the reaction, and the polymer solution was poured into a large amount of hexane to deposit a polymer. The polymer thus obtained was washed, filtered, dried and then weighed to obtain 0.171 g of the polymer.

The resulting polymer was measured for a molecular weight by GPC to observe a peak derived from the graft copolymer having a weight average molecular weight (Mw) of 139000, a number average molecular weight (Mn) of 72700 and a molecular weight distribution (Mw/Mn) of 1.91 on a high molecular weight side of the raw material block copolymer.

Further, molecular weight analysis of the peak of unreacted poly(2-vinylpyridine) showed that the grafted copolymer had a weight average molecular weight (Mw) of 3140, a number average molecular weight (Mn) of 2580 and a molecular weight distribution (Mw/Mn) of 1.22.

Example 25

Production of (p-methylstyrene)-b-(p-chlorostyrene-co-(m-methylstyrene)) block copolymer A 200 ml glass-made three-neck flask which was dried and replaced therein with nitrogen was used to carry out polymerization reaction under nitrogen atmosphere. The three-neck flask was charged with 69 ml of toluene and 0.1 mmol of trioctylaluminum to carry out aging at room temperature for 10 minutes. The flask was then charged with 0.1 mmol of (trimethyl)pentamethylcyclopentadienyltitanium and subsequently 0.09 mmol of tris(pentafluorophenyl)boron to carry out aging at room temperature for 10 minutes. Next, it was maintained at a constant temperature of −25° C. to carry out aging for 10 minutes. Then, the flask was charged with a toluene solution of 0.1 mmol of p-methylstyrene to further carry out aging for 60 minutes.

Then, the flask was charged with 20 ml of a toluene solution of 2.0 mmol of p-methylstyrene to carry out polymerization reaction at −25° C. for 25 minutes. Then, after a toluene solution of 10.0 mmol of p-chlorostyrene and 10.0 mmol of p-methylstyrene was added thereto to carry out the polymerization at the same temperature for 60 minutes, a small amount of methanol was added thereto to terminate the reaction, and the polymerization solution was poured into a large amount of a hydrochloric acid methanol solution to deposit a polymer. The polymer thus obtained was washed, filtered and dried, and then it was further dissolved in toluene and filtered. Then, the polymer was deposited again in a large amount of methanol, and the resulting polymer was washed, filtered, dried and then weighed to obtain 1.567 g of the polymer.

The polymer thus obtained had a weight average molecular weight (Mw) of 262000, a number average molecular weight (Mn) of 195000 and a molecular weight distribution (Mw/Mn) of 1.34.

Further, an average molecular weight and a molecular weight distribution of the p-methylstyrene polymer segment (I) contained in the present block copolymer were obtained from the production results of the homopolymer and were a weight average molecular weight (Mw) of 60800, a number average molecular weight (Mn) of 51100 and a molecular weight distribution (Mw/Mn) of 1.19. Also, the syndiotacticity determined by $^{13}$C-NMR measurement was 90% or more in terms of a racemic pentad. Further, the block copolymer had a composition of 89.5 mole % of p-methylstyrene and 10.5 mole % of p-chlorostyrene which were determined by $^{13}$C-NMR measurement.

Example 26

Production of chloromethyl-modified (p-methylstyrene)-b-(p-chlorostyrene-co-p-methylstyrene) block copolymer A 100 ml glass-made Schlenk flask which was dried and replaced therein with nitrogen was used to carry out reaction under nitrogen atmosphere. The Schlenk flask was charged with 0.100 g of the (p-methylstyrene)-b-(p-chlorostyrene-co-p-methylstyrene) block copolymer obtained in Example 25 and 2.0 ml of chloroform and then charged with 6.8 ml of a 5% sodium hypochlorite aqueous solution (pH was adjusted to 8.4 by conc. hydrochloric acid). Subsequently, an aqueous solution of 0.08 mmol of benzyltriethylammonium chloride was added thereto to carry out reaction at 25° C. for 6 hours.

Then, the reaction solution was poured into a large amount of methanol to deposit a polymer. The polymer thus obtained was washed, filtered, dried and then weighed to obtain 0.110 g of the polymer.

Converted into chloromethyl groups was 34.7 mole % of the methyl groups in p-methylstyrene of the block copolymer, which was determined by $^{13}$C-NMR measurement.

No change was observed in the steric structure of the resulting chloromethyl-modified (p-methylstyrene)-b-(p-chlorostyrene-co-p-methylstyrene) block copolymer as compared with that of the (p-methylstyrene)-b-(p-chlorostyrene-co-p-methylstyrene) block copolymer obtained in Example 25, which was the raw material.

Example 27

Production of (p-methylstyrene)-b-(styrene-co-(m-methylstyrene)) block copolymer A 200 ml glass-made three-neck flask which was dried and replaced therein with nitrogen was used to carry out polymerization reaction under nitrogen atmosphere. The three-neck flask was charged with 68 ml of toluene and 0.1 mmol of trioctylaluminum to carry out aging at room temperature for 10 minutes. The flask was then charged with 0.1 mmol of (trimethyl)pentamethylcyclopentadienyltitanium and subsequently 0.09 mmol of tris(pentafluorophenyl)boron to carry out aging at room temperature for 10 minutes. Next, it was maintained at a constant temperature of −25° C. to carry out aging for 10 minutes. Then, the flask was charged with a toluene solution of 0.1 mmol of p-methylstyrene to further carry out aging for 60 minutes.

Then, the flask was charged with 20 ml of a toluene solution of 2.0 mmol of p-methylstyrene to carry out polymerization reaction at −25° C. for 25 minutes. Then, after a toluene solution of 19.0 mmol of styrene and 10.0 mmol of m-methylstyrene was added thereto to carry out the polymerization at the same temperature for 30 minutes, a small amount of methanol was added thereto to terminate the reaction, and the polymerization solution was poured into a large amount of a hydrochloric acid methanol solution to deposit a polymer. The polymer thus obtained was washed, filtered and dried, and then it was further dissolved in toluene and filtered. Then, the polymer was deposited again in a large amount of methanol, and the resulting polymer was washed, filtered, dried and then weighed to obtain 0.781 g of the polymer.

The polymer thus obtained had a weight average molecular weight (Mw) of 209000, a number average molecular weight (Mn) of 153000 and a molecular weight distribution (Mw/Mn) of 1.37. Further, an average molecular weight and a molecular weight distribution of the p-methylstyrene polymer segment (I) contained in the present block copolymer were obtained from the production results of the homopolymer and were a weight average molecular weight (Mw) of 61100, a number average molecular weight (Mn) of 52000 and a molecular weight distribution (Mw/Mn) of 1.18. Also, the syndiotacticity determined by $^{13}$C-NMR measurement was 90% or more in terms of a racemic pentad. Further, the block copolymer had a composition of 63.3 mole % of styrene, 27.5 mole % of p-methylstyrene and 9.2 mole % of m-methylstyrene which were determined by $^{13}$C-NMR measurement.

Example 28

Production of chloromethyl-modified (p-methylstyrene)-b-(styrene-co-(m-methylstyrene)) Block Copolymer A 100 ml glass-made Schlenk flask which was dried and replaced therein with nitrogen was used to carry out reaction under nitrogen atmosphere. The Schlenk flask was charged with 0.200 g of the (p-methylstyrene)-b-(styrene-co-(m-methylstyrene)) block copolymer obtained in Example 27 and 10.0 ml of chloroform and then charged with 13.6 ml of a 5% sodium hypochlorite aqueous solution (pH was adjusted to 8.5 by conc. hydrochloric acid). Subsequently, an aqueous solution of 0.04 mmol of tetrabutylammonium hydrogen sulfite was added thereto to carry out reaction at 25° C. for 2 hours.

Then, the reaction solution was poured into a large amount of methanol to deposit a polymer. The polymer thus obtained was washed, filtered, dried and then weighed to obtain 0.185 g of the polymer.

Converted into chloromethyl groups was 13.6 mole % of the methyl groups in p-methylstyrene and m-methylstyrene of the block copolymer, which was determined by $^{13}$C-NMR measurement. No change was observed in the steric structure of the resulting chloromethyl-modified (p-methylstyrene)-b-(styrene-co-p-methylstyrene)) block copolymer as compared with that of the (p-methylstyrene)-b-(styrene-co-(m-methylstyrene)) block copolymer obtained in Example 27, which was the raw material.

Example 29

Production of (p-methylstyrene)-b-(styrene-co-(m-methylstyrene))-g-(2-vinylpyridine)) block•graft copolymer A 200 ml glass-made Schlenk bottle which was dried and replaced therein with nitrogen was used to carry out polymerization reaction under nitrogen atmosphere. A glass-made Schlenk bottle was charged with 50.0 ml of tetrahydrofuran (THF) and a cyclohexane/n-hexane solution of 0.1 mmol of sec-BuLi −78° to carry out aging for 10 minutes. Then, 2.0 ml of 2-vinylpyridine was slowly added thereto to start polymerization reaction. The polymerization reaction was carried out at the same temperature for 120 minutes.

Sampled was 35.9 ml of this polymerization reaction solution, and it was charged into another glass-made Schlenk bottle. Then, a THF solution of 0.080 g of the chloromethyl-modified (p-methylstyrene)-b-(styrene-co-(m-methylstyrene)) block copolymer obtained in Example 28 was added thereto to carry out grafting reaction for 15 hours. A small amount of methanol was added thereto to terminate the reaction, and the polymer solution was poured into a large amount of water to deposit a polymer. The polymer thus obtained was dissolved again in THF, and the solution was poured into a large amount of hexane to deposit the polymer.

The resulting polymer was washed, filtered, dried and then weighed to obtain 1.512 g of the polymer. The polymer thus obtained was extracted with methanol to remove unreacted poly(2-vinylpyridine).

The molecular weight was measured by GPC to observe a peak derived from the block•graft copolymer having a weight average molecular weight (Mw) of 7090000, a number average molecular weight (Mn) of 387000 and a molecular weight distribution (Mw/Mn) of 18.3. Further, the block•graft copolymer had a composition of 12.6 mole % of the total of styrene, p-methylstyrene and m-methylstyrene and a content of 87.4 mole % of 2-vinylpyridine which were determined by $^1$H-NMR measurement.

Further, molecular weight analysis of the peak of unreacted poly(2-vinylpyridine) showed that the grafted polymer had a weight average molecular weight (Mw) of 13100, a number average molecular weight (Mn) of 9570 and a molecular weight distribution (Mw/Mn) of 1.37.

Example 30

Production of (p-methylstyrene)-b-styrene block copolymer

A 200 ml glass-made three-neck flask which was dried and replaced therein with nitrogen was used to carry out polymerization reaction under nitrogen atmosphere. The three-neck flask was charged with 68 ml of toluene and 0.1 mmol of trioctylaluminum to carry out aging at room temperature for 10 minutes. The flask was then charged with 0.1 mmol of (trimethyl)pentamethylcyclopentadienyltitanium and subsequently 0.09 mmol of tris(pentafluorophenyl)boron to carry out aging at room temperature for 10 minutes. Next, it was maintained at a constant temperature of −25° C. to carry out aging for 10 minutes. Then, the flask was charged with a toluene solution of 0.1 mmol of p-methylstyrene to further carry out aging for 60 minutes.

Then, the flask was charged with 20 ml of a toluene solution of 2.0 mmol of p-methylstyrene to carry out polymerization reaction at −25° C. for 25 minutes. Then, after a toluene solution of 20.0 mmol of styrene was added thereto to carry-out the polymerization at the same temperature for 30 minutes, a small amount of methanol was added thereto to terminate the reaction, and the polymerization solution was poured into a large amount of a hydrochloric acid methanol solution to deposit a polymer. The polymer thus obtained was washed, filtered and dried, and then it was further dissolved in toluene and filtered. Then, the polymer was deposited again in a large amount of methanol, and the resulting polymer was washed, filtered, dried and then weighed to obtain 0.560 g of the polymer.

The polymer thus obtained had a weight average molecular weight (Mw) of 153000, a number average molecular weight (Mn) of 109000 and a molecular weight distribution (Mw/Mn) of 1.41. Further, an average molecular weight and a molecular weight distribution of the p-methylstyrene polymer segment (I) contained in the present block copolymer were obtained from the results in homopolymerization and were a weight average molecular weight (Mw) of 92900, a number average molecular weight (Mn) of 80900 and a molecular weight distribution (Mw/Mn) of 1.15. Also, the syndiotacticity determined by $^{13}$C-NMR measurement was 90% or more in terms of a racemic pentad. Further, the block copolymer had a composition of 63.0 mole % of styrene and 37.0 mole % of p-methylstyrene which were determined by $^{13}$C-NMR measurement.

Example 31

Production of (p-methylstyrene)-b-(p-tert-butylstyrene block copolymer

A 200 ml glass-made three-neck flask which was dried and replaced therein with nitrogen was used to carry out polymerization reaction under nitrogen atmosphere. The three-neck flask was charged with 68 ml of toluene and 0.1 mmol of trioctylaluminum to carry out aging at room temperature for 10 minutes. The flask was then charged with 0.1 mmol of (trimethyl) pentamethylcyclopentadienyltitanium and subsequently 0.09 mmol of tris(pentafluorophenyl)boron to carry out aging at room temperature for 10 minutes. Next, it was maintained at a constant temperature of −25° C. to carry out aging for 10 minutes. Then, the flask was charged with a toluene solution of 0.1 mmol of p-methylstyrene to further carry out aging for 60 minutes.

Then, the flask was charged with 20 ml of a toluene solution of 2.0 mmol of p-methylstyrene to carry out polymerization reaction at −25° C. for 25 minutes. Then, after a toluene solution of 20.0 mmol of p-tert-butylstyrene was added thereto to carry out the polymerization at the same temperature for 60 minutes, a small amount of methanol was added thereto to terminate the reaction, and the polymerization solution was poured into a large amount of a hydrochloric acid methanol solution to deposit a polymer. The polymer thus obtained was washed, filtered and dried, and then it was further dissolved in toluene and filtered. Then, the polymer was deposited again in a large amount of methanol, and the resulting polymer was washed, filtered, dried and then weighed to obtain 2.625 g of the polymer.

The polymer thus obtained had a weight average molecular weight (Mw) of 471000, a number average molecular weight (Mn) of 246000 and a molecular weight distribution (Mw/Mn) of 1.92. Further, an average molecular weight and a molecular weight distribution of the p-methylstyrene polymer segment (I) contained in the present block copolymer were obtained from the results in homopolymerization and were a weight average molecular weight (Mw) of 92900, a number average molecular weight (Mn) of 80900 and a molecular weight distribution (Mw/Mn) of 1.15. Also, the syndiotacticity determined by $^{13}$C-NMR measurement was 90% or more in terms of a racemic pentad. Further, the block copolymer had a composition of 10.0 mole % of styrene and 90.0 mole % of p-methylstyrene which were determined by $^{13}$C-NMR measurement.

Comparative Example 1

Production of poly-(p-chloromethylstyrene) polymer

A 200 ml glass-made three-neck flask which was dried and replaced therein with nitrogen was used to carry out polymerization reaction under nitrogen atmosphere. The three-neck flask was charged with 69 ml of toluene and 0.2 mmol of trioctylaluminum to carry out aging at room temperature for 10 minutes. The flask was then charged with 0.1 mmol of (trimethyl) pentamethylcyclopentadienyltitanium and subsequently 0.09 mmol of tris(pentafluorophenyl)boron to carry out aging at room temperature for 10 minutes. Next, it was maintained at a constant temperature of −25° C. to carry out aging for 30 minutes.

Then, after the flask was charged with 20 ml of a toluene solution of 2.0 mmol of p-chloromethylstyrene to carry out polymerization at −25° C. for 30 minutes, a small amount of methanol was added thereto to terminate the reaction, and the polymerization solution was poured into a large amount of a hydrochloric acid methanol solution to deposit a polymer. The polymer thus obtained was washed, filtered, dried and then weighed to obtain 0.171 g of the polymer.

The polymer thus obtained had a weight average molecular weight (Mw) of 1510, a number average molecular weight (Mn) of 1150 and a molecular weight distribution (Mw/Mn) of 1.31. The steric structure of the present polymer which was determined by $^{13}$C-NMR measurement was an atactic structure.

Comparative Example 2

Production of (p-chloromethylstyrene-co-p-methylstyrene) random copolymer

A 200 ml glass-made three-neck flask which was dried and replaced therein with nitrogen was used to carry out polymerization reaction under nitrogen atmosphere. The three-neck flask was charged with 69 ml of toluene and 0.2 mmol of trioctylaluminum to carry out aging at room temperature for 10 minutes. The flask was then charged with 0.1 mmol of (trimethyl) pentamethylcyclopentadienyltitanium and subsequently 0.09 mmol of tris(pentafluorophenyl)boron to carry out aging at room temperature for 10 minutes. Next, it was maintained at a constant temperature of −25° C. to carry out aging for 30 minutes.

Then, after the flask was charged with 20 ml of a toluene solution of 2.0 mmol of p-chloromethylstyrene and 8.0 mmol of p-methylstyrene to carry out polymerization reaction at −25° C. for 10 minutes, a small amount of methanol was added thereto to terminate the reaction, and the polymerization solution was poured into a large amount of a hydrochloric acid methanol solution to deposit a polymer. The polymer thus obtained was washed, filtered, dried and then weighed to obtain 1.216 g of the polymer.

The polymer thus obtained had a weight average molecular weight (Mw) of 4110, a number average molecular weight (Mn) of 1790 and a molecular weight distribution (Mw/Mn) of 2.30. The steric structure of the present polymer which was determined by $^{13}$C-NMR measurement was an atactic structure.

Industrial Applicability

The syndiotactic styrenic (co)polymer, the syndiotactic hydroxystyrenic (co)polymer, the syndiotactic styrenic block (co)polymer and the block•graft copolymer comprising a syndiotactic styrenic (co)polymer segment and a syndiotactic styrenic polymer segment containing a nitrogen-containing aromatic graft polymer according to the present invention can be used, because of a high syndiotacticity and a narrow molecular weight distribution thereof, as materials for printed circuit boards, offset PS printing plates and photoresists or various functional materials for flame retardant adhesives, compatibilizer, electroconductive resins, surfactants, raw materials of mosaic charging membrane for separating electrolytes, dispersants of light-emitting pigment for a photoelectric image and metal surface treating agents and as intermediates for producing functional resins such as anion exchange resins, supports for synthesizing peptide with solid phase and supports for high molecular reagents and high molecular catalysts, and an industrial usefulness thereof extends over a wide area.

Further, according to the process of the present invention, capable of being efficiently produced are a styrenic (co)polymer, a hydroxystyrenic (co)polymer, a styrenic block copolymer and a block•graft copolymer comprising a styrenic (co)polymer segment and a syndiotactic styrenic polymer segment containing a nitrogen-containing aromatic graft polymer each having a highly syndiotactic structure.

What is claimed is:

1. A syndiotactic trialkylsilyloxystyrenic polymer which is a polymer comprising a structural unit represented by the following Formula (7) and having a number average molecular weight of 600 or more:

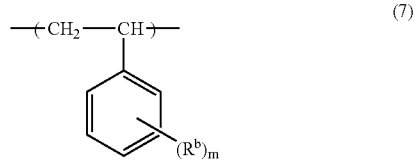

(7)

wherein $R^b$ represents a trialkylsilyloxy group having 3 to 30 carbon atoms;

n represents an integer of 1 to 3, and when n is plural, $R^b$'s may be the same or different; and in which a tacticity thereof is 30% or more in terms of a racemic pentad determined by $^{13}$C-NMR.

2. A process for the production of a trialkylsilyloxystyrenic polymer as described in claim 1 in which a trialkylsilyloxystyrenic monomer represented by the following Formula (8):

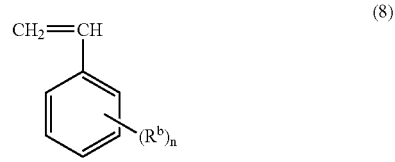

(8)

wherein $R^b$ represents a trialkylsilyloxy group having 3 to 30 carbon atoms;

n represents an integer of 1 to 3, and when n is plural, $R^b$'s may be the same or different is polymerized in the presence of a catalyst comprising a reaction product of a catalyst component (A) with a co-catalyst (B) wherein:

(A) is at least one transition metal compound selected from compounds represented by the following Formulas (4) or (5):

$$MR^1{}_x R^2{}_y R^3{}_z X^1{}_{4-(x+y+z)} \quad (4)$$

$$MR^1{}_u R^2{}_v X^3{}_{3-(u+v)} \quad (5)$$

wherein $R^1$, $R^2$ and $R^3$ each represent a hydrogen atom, an alkyl group having 1 to 20 carbon atoms, an aryl group, an alkylaryl group, an arylalkyl group and an aryloxy group each of which has 6 to 20 carbon atoms, an acyloxy group having 1 to 20 carbon atoms, an alkoxy group, having 1 to 20 carbon atoms, a thioalkoxy group having 1 to 20 carbon atoms, a thioaryloxy group having 6 to 20 carbon atoms, an amino group, a cyclopentadienyl group, a substituted cyclopentadienyl group, an indenyl group, a substituted indenyl group, a fluorenyl group or a substituted fluorenyl group, wherein $R^1$, $R^2$ and $R^3$ may be the same or different;

M represents a transition metal selected from the group consisting of titanium, zirconium, hafnium and vanadium;

$X^1$ represents a halogen atom;

x, y and z each represent an integer of 0 to 4, and u and v each represent an integer of 0 to 3; and (B) is at least one co-catalyst selected from the following (a) to (d):

(a) an organic aluminumoxy compound, (b) an ionic compound which can be reacted with the transition metal compound described above to form a cationic transition metal compound, (c) a Lewis acid compound which can be reacted with the transition metal compound described above to form a cationic transition metal compound, and (d) an organic metal compound of a first, second and thirteenth group elemental metal in the periodic table.

3. A hydroxystyrenic polymer having a syndiotactic structure which is a polymer having a structural unit represented by the following Formula (9) and a number average molecular weight of 600 or more:

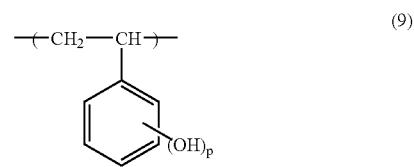

(9)

wherein p represents an integer of 1 to 3 and in which a tacticity thereof is 30% or more in terms of a racemic pentad determined by $^{13}$C-NMR.

4. A process for preparation of the hydroxystyrenic polymer as described in claim 3, comprising the steps of:

(i) polymerizing a styrenic monomer represented by the following Formula (10):

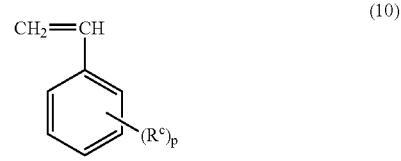

(10)

wherein $R^c$ represents a trialkylsilyloxy group having 3 to 30 carbon atoms, an alkoxy group having 4 to 31 carbon atoms or a trialkylgermaniumoxy group having 3 to 30 carbon atoms;

p represents an integer of 1 to 3, and when p is plural, $R^c$'s may be the same or different in the presence of a catalyst to thereby produce a styrenic polymer comprising at least one structural unit having a syndiotacticity of a high degree represented by the following Formula (11):

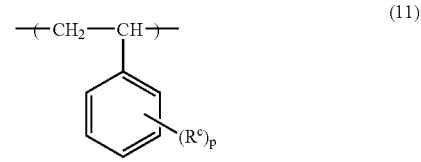

(11)

wherein $R^c$ represents a trialkylsilyloxy group having 3 to 30 carbon atoms, an alkoxy group having 4 to 31 carbon atoms or a trialkylgermaniumoxy group having 3 to 30 carbon atoms;

p represents an integer of 1 to 3, and when p is plural, $R^c$'s may be the same or different; and (ii) bringing the resulting styrenic polymer into contact with an acid or a base in the presence of an organic solvent to subject it to deblocking reaction, wherein the catalyst comprises a reaction product of a catalyst component (A) with a co-catalyst (B) wherein:

(A) is at least one transition metal compound selected from compounds represented by the following Formulas (4) or (5):

$$MR^1{}_xR^2{}_yR^3{}_zX^1{}_{4-(x+y+z)} \quad (4)$$

$$MR^1{}_uR^2{}_vX^3{}_{3-(u+v)} \quad (5)$$

wherein $R^1$ and $R^2$ and $R^3$ each represent a hydrogen atom, an alkyl group having 1 to 20 carbon atoms, an aryl group, an alkylaryl group, an arylalkyl group and an aryloxy group each of which has 6 to 20 carbon atoms, an acyloxy group having 1 to 20 carbon atoms, an alkoxy group, having 1 to 20 carbon atoms, a thioalkoxy group having 1 to 20 carbon atoms, a thioaryloxy group having 6 to 20 carbon atoms, an amino group, a cyclopentadienyl group, a substituted cyclopentadienyl group, an indenyl group, a substituted indenyl group, a fluorenyl group or a substituted fluorenyl group, wherein $R^1$, $R^2$ and $R^3$ may be the same or different;

M represents a transition metal selected from the group consisting of titanium, zirconium, hafnium and vanadium;

$X^1$ represents a halogen atom;

x, y and z each represent an integer of 0 to 4, and u and v each represent an integer of 0 to 3; and (B) is at least one co-catalyst selected from the following (a) to (d):

(a) an organic aluminumoxy compound, (b) an ionic compound which can be reacted with the transition metal compound described above to form a cationic transition metal compound, (c) a Lewis acid compound which can be reacted with the transition metal compound described above to form a cationic transition metal compound, and (d) an organic metal compound of a first, second and thirteenth group elemental metal in the periodic table.

5. A syndiotactic styrenic block copolymer comprising 0.1 mole % or more of at least one structural unit represented by the following Formula (20):

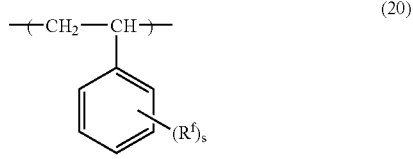

wherein $R^f$ represents a halogenated methyl group having a halogen atom selected from the group consisting of fluorine, chlorine, bromine and iodine, and s represents an integer of 1 to 5 in which $C_1$ carbon of the phenyl group thereof has a tacticity of 30% or more in terms of a racemic pentad determined by $^{13}$C-NMR.

6. A halogenated methyl-modified syndiotactic styrenic block polymer comprising structural units represented by the following Formula (12) and the following Formula (20):

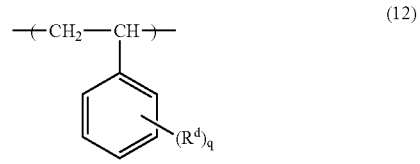

wherein $R^d$ represents a methyl group, and q represents an integer of 1 to 5

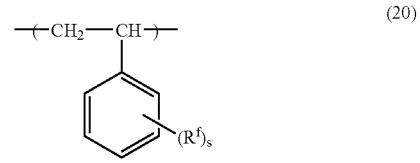

wherein $R^f$ represents a halogenated methyl group having a halogen atom selected from the group consisting of fluorine, chlorine, bromine and iodine, and s represents an integer of 1 to 5, wherein one or more structural units represented by Formula (12) and Formula (20) have a content satisfying the following equations (21) and (22), and $C_1$ carbon of phenyl groups in the polymer segments has a tacticity of 30% or more in terms of a racemic pentad determined by $^{13}$C-NMR:

$$2 < \text{structural unit (Formula (12))} + \text{structural unit (Formula (20))} < 100 \quad (21)$$

$$0.1 \leq \text{structural unit (Formula (20))} < 100 \quad (22).$$

7. A process for the preparation of a halogenated methyl-modified syndiotactic styrenic block polymer, comprising reacting a syndiotactic styrenic polymer comprising a structural unit represented by the following Formula (12):

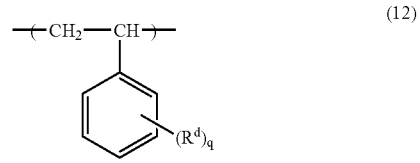

wherein $R^d$ represents a methyl group, and q represents an integer of 1 to 5 with a halogenating agent at a temperature of −20 to 200° C. in the presence of a catalyst and a solvent to convert a part or the whole part of the methyl groups to halogenated methyl groups, in which $C_1$ carbon of phenyl group thereof has a tacticity of 30% or more in terms of a racemic pentad determined by $^{13}$C-NMR.

8. A process for the production of a halogenated methyl-modified syndiotactic styrenic block copolymer, comprising reacting the syndiotactic styrenic block copolymer with a halogenating agent at a temperature of −20 to 200° C. in the presence of a catalyst and a solvent to convert a part or the whole part of the methyl groups to halogenated methyl groups, wherein the syndiotactic styrenic block copolymer has a structure where a polymer segment (I) which comprises at least one structural unit represented by the following Formula (12):

(12)

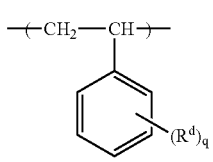

wherein $R^d$ represents a methyl group, and q represents an integer of 1 to 5 and in which $C_1$ carbon of a phenyl group thereof has a tacticity of 30% or more in terms of a racemic pentad determined by $^{13}$C-NMR is connected in series with a polymer segment (II) which comprises at least one structural unit represented by the following Formula (13):

(13)

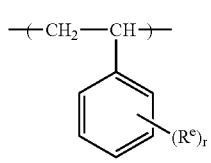

wherein $R^e$ represents a hydrogen atom, a hydrocarbon group having 1 to 30 carbon atoms or a substituent containing at least one selected from the group consisting of an oxygen atom, a nitrogen atom, a sulfur atom, a phosphorus atom, a selenium atom, a silicon atom, a tin atom and a germanium atom; and r represents an integer of 0 to 5, provided that when r is plural, respective $R^e$'s may be the same or different, and in which $C_1$ carbon of a phenyl group thereof has a tacticity of 30% or more in terms of a racemic pentad determined by $^{13}$C-NMR;

polymer segment (II) being different from polymer segment (I);

the number average molecular weight (Mn) desirably satisfies in a range of the following equation (14);

and a relation between the number average molecular weight (Mn) and the weight average molecular weight (Mw) of the block copolymer satisfies the following equation (15):

$$1200 \leq Mn \leq 20000000 \quad (14)$$

$$Mw/Mn \leq 2.5 \quad (15)$$

and Mw/Mn of the polymer segment (I) is 1.5 or lower.

9. A syndiotactic styrenic block•graft copolymer in which at least one structural unit per molecule of the polymer out of the structural units represented by Formula (20) contained in the syndiotactic styrenic polymer as described in any one of claims 5 or 6 is converted to a structural unit represented by the following Formula (23):

(23)

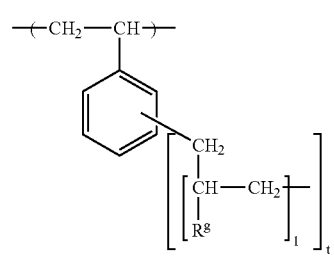

wherein $R^g$ represents at least one nitrogen-containing aromatic residue selected from the group consisting of pyridine, substituted pyridine, pyrimidine, substituted pyrimidine, pyrazine, substituted pyrazine, triazine, substituted triazine, quinoline, substituted quinoline, isoquinoline, substituted isoquinoline, acridine, substituted acridine, phthalazine, substituted phthalazine, quinoxaline, substituted quinoxaline, phenanthroline and substituted phenanthroline;

l represents a polymerization degree of 3 or more of the graft polymer; and t represents an integer of 0 to 5, wherein a relation between the number average molecular weight (Mn) and the weight average molecular weight (Mw) in the graft chain satisfies the following equation (24):

$$Mw/Mn \leq 2.0 \quad (24)$$

10. A process for the preparation of a syndiotactic styrenic (block)•graft copolymer having a graft chain, comprising bringing the halogenated methyl-modified syndiotactic styrenic polymer as described in any one of claims 5 and 6 into contact with a nitrogen-containing aromatic living polymer obtained by bringing an anionic polymerization initiator in advance into contact with a nitrogen-containing aromatic monomer represented by the following Formula (25) at −100 to 100° C.:

(25)

wherein $R^g$ represents at least one nitrogen-containing aromatic residue selected from the group consisting of pyridine, substituted pyridine, pyrimidine, substituted pyrimidine, pyrazine, substituted pyrazine, triazine, substituted triazine, quinoline, substituted quinoline, isoquinoline, substituted isoquinoline, acridine, substituted acridine, phthalazine, substituted phthalazine, quinoxaline, substituted quinoxaline, phenanthroline and substituted phenanthroline.

* * * * *